United States Patent
Sklar et al.

(10) Patent No.: US 7,232,659 B1
(45) Date of Patent: Jun. 19, 2007

(54) MULTIPLEX ANALYSIS FOR HIGH THROUGHPUT DISCRIMINATION OF GPCR AGONISTS AND ANTAGONISTS

(75) Inventors: Larry A. Sklar, Albuquerque, NM (US); Eric R. Prossnitz, Albuquerque, NM (US); Peter Simons, Albuquerque, NM (US); Anna Waller, Albuquerque, NM (US); Daniel Cimino, Tijeras, NM (US); Sean Biggs, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 348 days.

(21) Appl. No.: 10/771,853

(22) Filed: Feb. 4, 2004

Related U.S. Application Data

(60) Provisional application No. 60/444,635, filed on Feb. 4, 2003.

(51) Int. Cl.
*G01N 33/53* (2006.01)
*G01N 33/566* (2006.01)
*G01N 27/00* (2006.01)
*G01N 21/76* (2006.01)
*C07N 1/00* (2006.01)

(52) U.S. Cl. .................. 435/7.1; 436/501; 436/56; 436/172; 530/350; 530/402; 536/23.5; 435/69.1

(58) Field of Classification Search .................. None
See application file for complete search history.

(56) References Cited

U.S. PATENT DOCUMENTS

| | | |
|---|---|---|
| 4,275,149 A | 6/1981 | Litman et al. |
| 4,665,020 A | 5/1987 | Saunders |
| 5,405,784 A | 4/1995 | VanHoegaerden |
| 5,583,010 A | 12/1996 | Baumbach et al. |
| 5,601,992 A | 2/1997 | Lerner et al. |
| 5,639,603 A | 6/1997 | Dower |
| 5,698,685 A | 12/1997 | Summerton et al. |
| 5,747,349 A | 5/1998 | Van den Engh et al. |
| 5,763,585 A | 6/1998 | Nag |
| 7,018,846 B1 | 3/2006 | Sklar et al. |

OTHER PUBLICATIONS

Sklar et al. 2000. Biotechniques. 28:976-985 (pp. 979 and 981 are journal advertisements and are not included).*
Sklar et al. 2002 Ann. Rev Biophys Biomol Struct. 31:97-119.*
Sarvazyan et al. 2002. Biochemistry 41:12858-12867.*
Bednar et al., "Flow cytometric measurement of kinetic and equilibrium binding parameters of arginine-glycine-aspartic acid ligands binding to glycoprotein IIb/IIa on platelets." *Cytometry*, Feb. 1997, vol. 28, pp. 58-65.
David et al. "Expression and purification of the Saccharamyces cerevisiae alpha-factor receptor (Ste2p), a 7-transmembrane-segment G protein-coupled receptor." *J. Biol. Chem.* Jun. 1997, vol. 272, No. 24, pp. 15553-15561.
Eppler et al., *J. Biol Chem.* 267:22(15603-15612)92.
Jayawickreme et al.., *PNAS* 91(1614-1618) 1994.
Jones et al., *J. Chromatography A* 707(3-22)1995.
Lindner et al., "Specific detection of His-tagged proteins with recombinant anti-his tag scFv-phosphatase or scFv phage fusions." *BioTechniques*. Jan. 1997, vol. 22, No. 1, pp. 140-149, especially p. 142.
Robeva et al., "Double tagging recombinant A1 and A2a adenosine receptors with hexahistidine and the FLAG epitope." *Bioch. Pharm.* Jan. 1996, vol. 51, pp. 545-555.
Robeva et al., *Drug Development Research* 39(243-252) 1996.
Sklar et al., "Regulation of Ligand-Receptor Dynamics by Guanine Nucleotides", *Journal of Biological Chemistry*, vol. 262, No. 1, pp. 135-139, Jan. 5, 1987.
Szollosi et al., *Cytometry* 8(120-128) 1987.
Wang et al., "Probing Transmembrane Mechanical Coupling and Cytomechanics Using Magnetic Twisting Cytometry" *Biochem. Cell Bio.* vol. 73, pp. 327-335, 1995.
Hodder et al., "Microfabricated Flow Chamber for Fluorescence-based Chemistries and Stopped-flow Injection Cytometry", *Analyst*, 1997, 122:883-887.
Nolan et al., "A Rapid Mix Flow Cytometer with Subsecond Kinetic Resolution", *Cytometry*, 1995, 21:223-229.
Nolan et al., "The Emergence of Flow Cytometry for Sensitive, Real-Time Measurements of Molecular Interactions", *Nature Biotechnology*, 1998, 16:633-638.
Toei et al., "An Improved Reaction Valve for flow Injection Analysis", *Fresenius Z Anal Chem*, 1989, 223:13-15.
U.S. Appl. No. 10/101,870, filed Mar. 2002, Sklar et al.

* cited by examiner

*Primary Examiner*—Brenda Brumback
*Assistant Examiner*—Shulamith Shafer
(74) *Attorney, Agent, or Firm*—Henry D. Coleman; R. Neil Sudol; William J. Sapone

(57) ABSTRACT

The present invention relates generally to molecular assemblies, more particularly to an assay for the detection of G-protein coupled receptor (GPCR) molecular assemblies and bead-based detection of ligand-GPCR complexes and to methods for identifying compounds as agonists, partial agonists or antagonists of the binding of G-protein coupled receptors to G-protein and for use of these compounds in the treatment of conditions or disease states in a mammalian subject or patient, including humans, where G-protein coupled receptor binding to G-protein is implicated.

8 Claims, 20 Drawing Sheets

A

B

C

Changes from the standard assembly:

1. No αβγ
2. No α
3. (standard)
4. +GTPγS
5. Irrelevant L-fl
6. No R

1. No βγ
2. +GTPγS
3. (standard)
4. 0.1 μM GTP
5. 0.5 μM GTP
6. 1 μM GTP
7. 5 μM GTP
8. 10 μM GTP
9. 25 μM GTP
10. 50 μM GTP
11. 200 μM GTP 1. No αβγ
2. No α
3. (standard)
4. +GTPγS
5. No L

FIGURE 16

| Lig-and | LR: $K_d$ (nM) | ARG: $EC_{50}$ (nM) | ARG Assembly |
|---|---|---|---|
| ALP | 1.8 (0.1*) | NA | NA |
| ISO | 220 (68) | 180 | 100% |
| EPI | 680 (370) | 280 | 90% |
| NE | 19,000 (10,000) | 19,000 | 90% |
| SAL | 2,300 (ND) | 1,200 | 30% |
| DOB | 2,400 (2,300) | 2,600 | 10% |

MULTIPLEX ANALYSIS FOR HIGH THROUGHPUT DISCRIMINATION OF GPCR AGONISTS AND ANTAGONISTS

RELATED APPLICATIONS

This application claims the benefit of priority of provisional application No. 60/444,635, entitled Mutiplex Analysis for High Throuput Discrimination of GPCR Agonists and Antagonists, filed Feb. 4, 2003.

GOVERNMENT SUPPORT

This invention is made with government support under any one or more of Grant Numbers GM60799/EB-00264, awarded by the National Institutes of Health. The government may have certain rights in this invention.

FIELD OF THE INVENTION

The present invention relates generally to molecular assemblies, more particularly to an assay for the detection of G-protein coupled receptor (GPCR) molecular assemblies and bead-based detection of ligand-GPCR complexes and to methods for identifying compounds as agonists, partial agonists or antagonists of the binding of G-protein coupled receptors to G-protein and for use of these compounds in the treatment of conditions or disease states in a mammalian subject or patient, including humans, where G-protein coupled receptor binding to G-protein is implicated.

BACKGROUND OF THE INVENTION

G protein coupled receptors (GPCRs) transmit extracellular signals into cells via intracellular G protein heterotrimers (1). Of currently marketed drugs, more than 30% modulate GPCRs (2). Only 10% of the 367 human endogenous ligand GPCRs are targeted by current drugs, leaving many future targets. Novel modes of defining the activity of ligands that bind to GPCRs could contribute to the treatment of human disease.

The response to epinephrine or adrenaline is a prototypic GPCR action. Equilibrium binding studies in frog erythrocyte membranes demonstrated homogeneous binding for antagonists, while agonists exhibited two states of agonist affinity (3). The ternary complex model of agonist, receptor, and G protein accounts for the ternary complex exhibiting a higher agonist affinity than the binary complex (4). Adenylyl cyclase assays define the intrinsic activity, or efficacy, for each compound. Receptors in the high affinity state range from 50% for agonists of the lowest intrinsic activity to 95% for full agonists, the percent correlated roughly with the intrinsic adenylyl cyclase activity of the agonist. The functional consequences of cellular ternary complex formation include the rapid binding of GTP to the Gα subunit, release of the receptor and the Gβγ dimer, and exposure of new Gα and Gβγ surfaces to interact with effectors such as adenylyl cyclase (5). Ternary complex formation for a series of agonists is expected to correlate with adenylyl cyclase activities. More detailed ternary complex formulations take into account the idea that receptors can exist in different activity states (6).

The present inventors have previously studied the formyl peptide receptor and its numerous fluorescent ligands. The solublilized receptor forms a high agonist affinity complex with G proteins and arresting. See, Bennett, et al., 2001 *J. Biol. Chem.* 276, 22453–22460; Bennett, et al., 2001, *J. Biol. Chem.* 276, 49195–49203; and Key, et al., 2001, *J. Biol. Chem.* 276, 49204–49212. Beads derivatized with chelated nickel bind hexahistidine-tagged G protein heterotrimers, and as shown by flow cytometry, form ternary complex with FPR constructs on G protein beads. The constructs included wild type receptor detected with fluorescent ligand, receptor-Gα fusion protein detected with fluorescent ligand, and receptor-GFP fusion protein detected with nonfluorescent ligand See, Simons, et al., 2003, *Mol. Pharmacol.* 64, 1227–1238. The technology demonstrated also includes one of the receptors for adrenaline, the beta 2 adrenergic receptor (β2AR), which was used in the form of a fusion protein with green fluorescent protein, the β2AR-GFP fusion protein. A well-known β2AR ligand was attached to beads, and the formation of ligand:receptor binary complexes was detected by increasing fluorescence of the beads, in a process analogous to affinity chromatography. As with the FPR-GFP, β2AR-GFP was able to bind cognate agonists to form agonist:receptor-GFP binary complexes, which in turn were able to bind to cognate hexahistidine-tagged G protein on chelated nickel beads to form ternary agonist:receptor-GFP:G protein complexes on chelated nickel beads. These complexes were also detected by increasing fluorescence of the beads.

The interactions of ligands with GPCRs have mainly been studied in membrane preparations with radiolabelled ligands (e.g., see references 3 and 4 for the β2AR), which are not amenable to high throughput screening. Therefore, appropriate tools in these areas have been limited and, in many situations, unsatisfactory. Thus, there is a need for a homogeneous, small volume bead-based approach compatible with high throughput flow cytometry, which would allow evaluation of G protein coupled receptor molecular assemblies. The present approach provides a general solution for addressing that need.

OBJECTS OF THE INVENTION

It is therefore an object of the present invention to provide a homogeneous, small volume bead-based approach compatible with high throughput flow cytometry.

It is a further object to provide a small volume bead-based approach that provides for evaluation of G protein coupled receptor molecular assemblies.

It is a further object to provide a method for coating beads with functional G proteins, hereafter named G protein beads.

It is a further object to provide a method for detection of ligands, which uses a GPCR-GFP fusion protein in combination with G protein beads.

It is still a further object to provide beads useful in flow cytometry which can bind GPCR-GFP fusion proteins.

It is still a further object of the invention to provide high throughtout screens for identifying compounds as inhibitors or agonists of GPCR binding in G-protein complexes.

It is yet an additional object of the invention to provide high throughput screens for identifying potential pharmaceutical compounds useful in the treatment of conditions or disease states wherein GPCR G-protein complex formation or binding is implicated.

These and/or other aspects of the present invention may be readily gleaned from a reading of the description of the invention which follows.

SUMMARY OF THE INVENTION

According to a first broad aspect of the present invention, there is provided a method comprising the steps of: providing a sample suspension containing at least one set of G protein beads, each of the G-protein beads comprising epitope-recognizing beads having a heterotrimeric G protein bound thereto; mixing the sample suspension with at least one type of G protein coupled receptor and a ligand to thereby form a mixed suspension containing a ligand-receptor-G protein complex when the G protein is capable of forming complex with the receptor and the ligand; and mixing the mixed suspension to incubate the mixed suspension and thereby form an incubated suspension; detecting the formation of a stable ligand-receptor-G protein complexes in the incubated suspension by flow cytometry.

According to a second broad aspect of the invention, there is provided a method of forming G protein beads comprising the steps of: providing epitope-recognizing beads; and binding epitope-bearing G protein subunits to the epitope-recognizing beads to form G protein beads.

According to a third broad aspect of the invention, there is provided a method of forming GPCR beads or GPCR-GFP fusion protein beads by providing a bead which has been modified preferably to contain a GPCR or a GPCR-GFP fusion protein ligand to which is bound a GPCR or a GPCR-GFP fusion protein. Measuring the binding of the GPCR or GPCR-GFP fusion protein in the presence of a compound to be identified as an agonist or antagonist is readily performed. A further aspect of this invention relates to comparing/assessing the binding measurements to standard known agonists/antagonists.

According to another aspect of the invention, a method is provided comprising evaluating G-protein receptor agonism (including partial agonism) or antagonism of a compound by bead-based flow cytometric process comprising contacting the compound with beads conjugated to a G-protein coupled receptor detectable moiety to produce an interaction, wherein the extent to which the compound complexes with the receptor detectable moiety complex to form a detectable ternary complex is determined by measuring detectable ternary complex levels wherein said detectable ternary complex levels are indicative of a compound's receptor agonism or antagonism.

According to another aspect of the invention, a method is provided comprising evaluating G-protein receptor agonism or partial agonism of a compound by bead-based flow cytometric process comprising contacting the compound in a solution of solubilized GPRC with beads coated (i.e., conjugated or bound to) with heterotrimeric G-protein, and measuring whether an interaction between GPCR and G protein occurs, wherein the extent to which the compound complexes with GPCR and G protein to form a detectable ternary complex is determined by measuring detectable ternary complex formation wherein said detectable ternary complex formation is indicative of a compound's receptor agonism or partial agonism.

According to yet another aspect of the invention, there is provided a high through-put method of determining whether a compound is an agonist, partial agonist or antagonist of GPCR-GP binding or complex formation or is inactive, preferably in a single sample, by measuring agonist or antagonist activity or inactivity of a compound simultaneously, preferably in the same sample solution, said method comprising conducting each of the two above-described methods simultaneously and determining whether said compound exhibits agonist, partial agonist, antagonist of GPCR-GP binding or is inactive.

Thus, the invention provides a novel and generalizable approach to investigate G protein coupled receptor molecular assemblies, and more particularly, to assess the agonist, antagonist or inactivity of a library of compounds in an efficient high throughput screen, preferably by flow cytometry. More specifically, the invention provides methods for evaluating the relative β2-adrenergic receptor agonism or antagonism of a compound by a flow cytometric process comprising contacting the compound with beads conjugated to a β2-adrenergic receptor-detectable moiety complex, wherein the extent to which the compound complexes with the β2-adrenergic receptor-detectable moiety complex to form a detectable ternary complex is determined by measuring detectable ternary complex levels and detectable ternary complex levels are indicative of the compound's β2-adrenergic receptor agonism or partial agonism.

In another embodiment, the invention provides a generalizable approach to investigating the interaction of a soluble GPCR with a bead modified with a ligand of said GPCR. By measuring the binding of the receptor to the ligand in the presence of an unknown compound, the compound's agonist or antagonist activity with the GPCR can be determined. This approach may also be adapted for use in a method for simultaneously measuring a compound's agonist activity, antagonist activity or inactivity with a GPCR.

In one embodiment of the invention, a solubilized a fusion protein, comprising a GPCR and a fluorescent protein, including a green, red or cyan fluorescent protein, preferably a green fluorescent protein (GFP) is used in the assay system as a detectable GPCR. In one aspect of the invention, a solubilized fusion protein consisting of the β2-adrenergic receptor and green fluorescent protein (β2AR-GFP), was used for bead-based flow cytometric analysis. β2AR-GFP bound to dihydroalprenolol-conjugated beads, provided a $K_d$ for the fusion protein, and in competition with β2AR ligands, $K_d$'s for agonists and antagonists. In another aspect, beads displaying chelated nickel bound purified hexahistidine-tagged G protein heterotrimers, and subsequently, the binary complex of agonist with β2AR-GFP. The dose-response curves of ternary complex formation revealed maximal assembly for ligands previously classified as full agonists, and reduced assembly for ligands previously classified as partial agonists. GTPγS-induced dissociation rates of the ternary complex were the same for full and partial agonists. Soluble G protein, competing with ternary complexes on beads, provided an affinity estimate of agonist-receptor complexes to G protein. When performed simultaneously, the two assemblies described herein discriminated between agonist, antagonist, or inactive molecule in a manner appropriate for high throughput, small volume drug discovery. The method is particularly adaptable for use in flow cytometry although other high throughput screening methods may also be employed. The assemblies can be further generalized to numerous other G protein coupled receptor protein—protein interactions.

These and other aspects of the invention are described in greater detail in the detailed description of the invention.

BRIEF DESCRIPTION OF THE FIGURES

FIG. 3A illustrates specificity of the DHA bead interaction with the β2AR-GFP fusion protein, with 1 mM ALP included in assays represented with striped bars. The first two assays were standard, using 50 nM β2AR-GFP; the second two assays used FPR-GFP instead of β2AR-GFP; and the third pair of assays used underivatized beads in place of DHA beads. FIG. 3B illustrates binding curves were obtained by varying the amount of β2AR-GFP as shown in the absence (filled symbols) or presence (open symbols) of 1 mM ALP, for the times indicated on the side. FIG. 3C illustrates the time course of β2AR-GFP binding to DHA beads; data replotted from Panel B.

FIG. 4A illustrates that the ARG assembly requires cognate agonist, receptor, and G protein. Assemblies on G protein-coated Ni beads were conducted as described in "Experimental Procedures", except as noted, using 40 nM β2AR-GFP or FPR-GFP, 1 mM ISO as the agonist, cognate Gβsβ1γ2 (s) or noncognate Gαi3β1γ2 (i) heterotrimer, and 0.1 mM GTPγS, as indicated. FIG. 4B illustrates how ARG assembly varied as the ligand used and the amount of β2AR-GFP used in the standard assembly were varied as shown, using 1 mM isoproterenol (ISO) or salbutamol (SAL) for agonists, and 0.1 mM GTPγS where indicated. FIG. 4C illustrates how ARG assembly varied as the amount of G protein used to coat the Ni beads was varied before conducting the standard ARG assembly. FIG. 4D illustrates how ARG assembly varied as the time of assembly was varied as shown, using 40 nM β2AR-GFP and 1 mM ISO, SAL, or DOB. FIG. 4E illustrates how ARG assembly varied as the soluble Gαsβ1γ2 heterotrimer was added to standard assays to compete with the bead-borne Gαsβ1γ2; 0.1 mM GTPγS was added as indicated. FIG. 4F illustrates ARG disassembly by kinetic activation of ARG using manual addition of 0.1 mM GTPγS. Open squares show the standard assembly with the fluorescence of the beads followed uninterrupted. The plus symbols show the assembly in which GTPγS was present during the entire assembly. The filled squares show a standard assembly in which the bead fluorescence was followed for 20 seconds, the tube was removed from the cytometer, 0.1 mM GTPγS was added manually and mixed at 25 seconds, the tube was returned to the cytometer, and bead fluorecence was followed for the remaining time.

FIG. 5A illustrates the decrease of fluorescence of DHA beads when DHA beads were used in the standard binding assay, with 9 nM β2AR-GFP, and increasing amounts of various ligands. The ligands were allowed to block the receptor for 5 minutes before the DHA beads were added and mixed for two hours. FIG. 5B illustrates the increase of fluorescence of G protein beads G protein coated beads were used in the standard ARG assembly assay, with 20 nM β2AR-GFP, and agonists at the concentrations shown.

FIG. 8 provides a graphical representation of soluble receptor determination.

FIG. 9 shows the characterization of dextran chelate nickel (DCNi) beads by flow cytometry.

FIG. 11 shows results from a calibrated LRG assembly with three receptor constructs on DCNi beads.

FIG. 12 shows the effects of time and ternary complex partner concentrations on LRG assembly. The standard assembly for $LR^F G$ (see the experimental procedures contained herein; scheme of FIG. 10, complex D) was used for FIGS. 12A, 12B, 12C and 12D.

FIG. 13 shows the determination of interaction constants for nonfluorescent ligands. Triangles represent fMLFF, circles represent fMLF, and squares represent fML.

FIG. 15 shows LRG disassembly with GTPγS.

FIG. 16, Table 1 shows a comparison of the $K_d$ values for LR formation for selected ligands using DHA beads in column 2, to their $EC_{50}$ values for ARG assembly using G protein beads in column 3 (potency), and to their relative values for maximal ARG assembly using G protein beads in column 4. The data were obtained from three experiments as shown in FIG. 5. The data in parentheses are from earlier work (15). ND, not determined; *, value is 5–20 fold lower than most other reported values for mammalian β2AR (28–31).

DETAILED DESCRIPTION OF THE INVENTION

Figure 1:
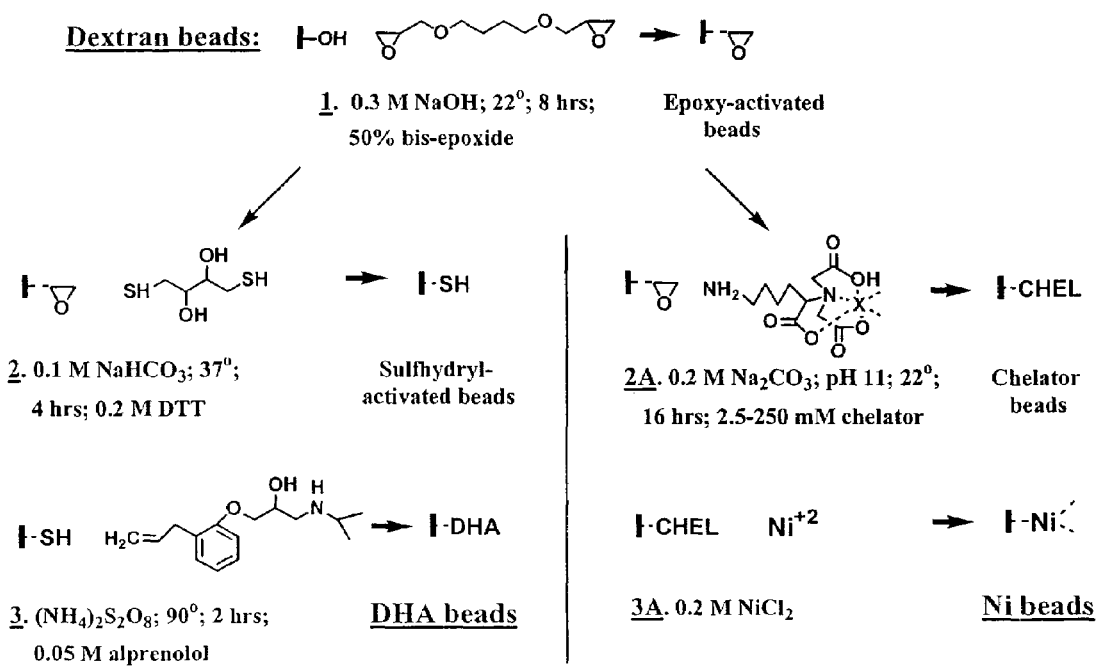
FIG. 1 illustrates an outline of the syntheses of DHA beads and Ni beads. Both syntheses begin with the epoxidation of agarose/dextran beads as shown at the top. The synthetic details are given in "Experimental Procedures".

Numbers in parentheses in context generally refer to the references which are set forth and listed in the section after the experimental in the present specification. Terms not specifically defined herein are to be given their common meaning as understood by those of ordinary skill in the art. Relevant portions of all references which are cited herein within context whether published papers, website information or related information, are incorporated by reference herein.

As used herein, the following terms have the following respective meanings.

The term "agonist", as used herein, is meant to refer to an agent that mimics or upregulates (e.g., potentiates or supplements) an activity of a compound, e.g., a protein. An agonist can be a wild-type protein or derivative thereof having at least one bioactivity of the wild-type protein. An agonist can also be a compound that upregulates expression of a gene or which increases at least one bioactivity of a protein. An agonist can also be a compound which increases the interaction of a polypeptide with another molecule, e.g., a target peptide or nucleic acid.

"Antagonist" as used herein is meant to refer to an agent that downregulates (e.g., suppresses or inhibits) at least one activity of a compound, e.g., a protein. An antagonist can be a compound which inhibits or decreases the interaction between a protein and another molecule, e.g., a target peptide or enzyme substrate. An antagonist can also be a compound that downregulates expression of a gene or which reduces the amount of expressed protein present.

The term "DNA sequence encoding a polypeptide" refers to any nucleic acid that encodes a polypeptide, including, e.g., a cDNA, a cDNA fragment, a genomic DNA, a genomic DNA fragment, and a synthetic DNA. Moreover, certain differences in nucleotide sequences may exist between individual organisms, of the same or different species, which are called alleles. Such allelic differences may or may not result in differences in amino acid sequence of the encoded polypeptide yet still encode a polypeptide with the same biological activity.

The term "equivalent", with respect to a nucleotide sequence, is understood to include nucleotide sequences encoding functionally equivalent polypeptides. Equivalent nucleotide sequences will include sequences that differ by one or more nucleotide substitutions, additions or deletions, such as allelic variants and therefore include sequences that differ due to the degeneracy of the genetic code. "Equivalent" also is used to refer to amino acid sequences that are functionally equivalent to the amino acid sequence of a mammalian homolog of a SIRT2 protein, but have different amino acid sequences, e.g., at least one, but fewer than 30, 20, 10, 7, 5, or 3 differences, e.g., substitutions, additions, or deletions.

"Homology", "homologs of", "homologous", or "identity" or "similarity" refers to sequence similarity between two polypeptides or between two nucleic acid molecules, with identity being a more strict comparison. Homology and identity can each be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. An "unrelated" or "non-homologous" sequence shares less than 40% identity, though preferably less than 25% identity, with one of the sequences of the present invention.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for determining sequence identity are well-known and described in the art.

The term "interact" as used herein is meant to include detectable interactions (e.g., biochemical interactions) between molecules, such as interaction between protein—protein, protein-nucleic acid, nucleic acid-nucleic acid, and protein-small molecule or nucleic acid-small molecule in nature.

As used herein, the term "nucleic acid" refers to polynucleotides such as deoxyribonucleic acid (DNA), and, where appropriate, ribonucleic acid (RNA). The term also includes, as equivalents, analogs of RNA or DNA made from nucleotide analogs, and single (sense or antisense) and double-stranded polynucleotides. ESTs, chromosomes, cDNAs, mRNAs, and rRNAs. The term "nucleotide sequence complementary to the nucleotide sequence of SEQ ID NO. "x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a noncoding strand.

As used herein, the term "promoter" means a DNA sequence that regulates expression of a particular DNA sequence operably linked to the promoter, and which effects expression of the particular DNA sequence in cells. The term encompasses "tissue specific" promoters, i.e., promoters which regulate expression of the selected DNA sequence as a function of cellular state, e.g., differentiation state. Typically tissue specific promoters are active only in specific cells (e.g., cells of a specific tissue). The term also covers so-called "leaky" promoters, which regulate expression of a selected DNA primarily in one tissue, but cause expression in other tissues as well. Other promoters that can be used include non-tissue specific promoters and promoters that are constitutively expressed or that are inducible (i.e., expression levels can be controlled).

The terms "protein", "polypeptide", and "peptide" are used interchangeably herein to refer to a polymer of amino acids. However, a protein may include more than one polypeptide chain. A polypeptide can be a gene product, although some polypeptides can be produced synthetically.

The term "recombinant protein" refers to a polypeptide of the present invention which is produced by recombinant DNA techniques. In an exemplary method, DNA encoding a polypeptide is inserted into a suitable expression vector which is in turn used to transform a host cell to produce the heterologous protein. In another exemplary method, homologous recombination is used to insert a heterologous regulatory sequence into an endogenous gene. Moreover, the phrase "derived from", with respect to a recombinant gene, is meant to include within the meaning of "recombinant protein" those proteins having an amino acid sequence of a native polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

A "compound" or "test compound" can be any chemical compound, for example, a macromolecule (e.g., a polypeptide, a protein complex, or a nucleic acid) or a small molecule (e.g., an amino acid, a nucleotide, an organic or inorganic compound). The test compound can have a formula weight of less than about 10,000 grams per mole, less than 5,000 grams per mole, less than 1,000 grams per mole, or less than about 500 grams per mole. The test compound can be naturally occurring (e.g., a herb or a nature product), synthetic, or both. Examples of macromolecules are proteins, protein complexes, and glycoproteins, nucleic acids, e.g., DNA, RNA (e.g., double stranded RNA or RNAi) and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds. One exemplary type of protein compound is an antibody or a modified scaffold domain protein. A test compound can be the only substance assayed by the method described herein. Alternatively, a collection of test compounds can be assayed either consecutively or concurrently by the methods described herein.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science,* 274: 1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like). Additional examples of methods for the synthesis of molecular libraries can be found in the art, for example in: DeWitt et al. (1993) *Proc. Natl. Acad. Sci. U.S.A.* 90:6909;

Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Some exemplary libraries are used to generate variants from a particular lead compound. One method includes generating a combinatorial library in which one or more functional groups of the lead compound are varied, e.g., by derivatization. Thus, the combinatorial library can include a class of compounds which have a common structural feature (e.g., framework).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

The test compounds of the present invention can also be obtained from: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological libraries include libraries of nucleic acids and libraries of proteins. Some nucleic acid libraries encode a diverse set of proteins (e.g., natural and artificial proteins; others provide, for example, functional RNA and DNA molecules such as nucleic acid aptamers or ribozymes. A peptoid library can be made to include structures similar to a peptide library. (See also Lam (1997) *Anticancer Drug Des.* 12:145). A library of proteins may be produced by an expression library or a display library (e.g., a phage display library).

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223,409), spores (Ladner U.S. Pat. No. 5,223,409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310).

"G protein-coupled receptors" are the single largest class of cell surface receptors, mediate a wide variety of essential physiological functions. For example, G protein-coupled receptors mediate the chemotactic movement of cells that ensures an adequate immune response, transmit the signals carried by hormones, and capture external stimuli such as the photons that strike the retina and the odorant molecules that strike the nasal epithelium (Probst et al., *DNA Cell Biol.* 11: 1–20, 1992). Those that are relevant for use in the present invention are generally divided into three types of receptors rhodopsin receptors, including hormone, neurotranmitter and light receptors; secretin receptors, including calcitonin, parathyroid hormone and vasoactive intestinal peptide receptors; and metabotropic glutamate receptors, including calcium sensing and GABA receptors.

All G protein-coupled receptors contain seven domains that traverse back and forth across the cell membrane; the proteinaceous loops that form between these transmembrane domains extend into the extracellular and intracellular spaces. The loops that extend extracellularly specifically interact with ligands, particularly peptide and protein ligands, and the intracellular loops interact with G proteins on the inner surface of the cell membrane, thereby beginning the biochemical cascade that transmits the extracellular signal to the interior of the cell. The third intracellular loop of many G protein-coupled receptors, particularly those that function as adrenergic and cholinergic receptors, is the largest intracellular structure, and is thought to be especially important for the interaction between the receptor and a G protein (Lefkowitz et al., Cold Spring Harbor Symposia Quant. Biol. 53:507–514, 1988).

G protein coupled receptors (GPCRs) interact with extracellular stimuli, such as photons, hormones, neurotransmitters, and odorants, see Gilman A G (1995), Nobel Lecture, G Proteins and Regulation of Adenylyl Cyclase, Biosci Rep, 15, pp 65–97, the entire contents and disclosure of which is hereby incorporated by reference. These stimuli cause coformational changes in the receptor leading to binding of intracellular G protein heterotrimers, each with one copy of a guanyl nucleotide binding α subunit, and a β γ. dimer, see Neer E J (1995), Heterotrimeric G Proteins: Organizers of Transmembrane Signals, Cell, 80, pp 249–257, the entire contents and disclosure of which is hereby incorporated by reference. After stimulation, the α subunit binds GTP, which promotes dissociation of the α subunit from the β γ dimer, exposing new surfaces to cytoplasmic effectors, such as adenylyl cyclase and phospholipase C. The assembly of a high agonist-affinity complex is a good criterion of productive partners, see Gilman A G (1987), G Proteins: Transducers of Receptor-Generated Signals, Ann Rev Biochem, 56, pp 615–649, the entire contents and disclosure of which is hereby incorporated by reference.

The human genome contains about 600 GPCR genes, 27α, 5β, and 13γ, see Venter et al. (2001), The Sequence of the Human Genome, Science, 291, pp 1304–1351, the entire contents and disclosure of which is hereby incorporated by reference, with smaller numbers of these G proteins (References 17, 5 and 12, respectively) found to date. The human genome contains 27α, 5β, and 13γ G protein subunits, see Venter et al., (2001), The Sequence of the Human Genome, Science, 291, pp 1304–1351, although it is possible that other sequences will be found. The present invention uses a number of these: for example, the NCBI protein databank accession number for β1 is NP_002065; the NCBI nucleic acid database accession number for as short form is AF493898, and for γ2 is BC060856. Other human sequences for all the G protein subunits are available in both of these databases. Since these proteins must interact with their partners, their sequences are constrained, and it is expected that the homologs from other species will work, e.g., that as from monkey or dog will substitute for human αs. The present invention in fact provides a test for such interactions, which are the subject of ongoing research in biology. It is also expected that various fusion proteins will work, such as an αs-β1-γ2 fusion protein from human or mixed species, with appropriate linking peptides between them.

The formyl peptide receptor (FPR) responds to the presence of N-formyl methionine-containing peptides resulting from bacterial and mitochondrial protein synthesis, as well as other hydrophobic peptides, see Gao et al. (1994), A High Potency Nonformylated Peptide Agonist for the Phagocyte N-Formylpeptide Chemotactic Receptor, J Exp Med, 180, pp 2191–2197, the entire contents and disclosure of which is hereby incorporated by reference. This receptor has served as a model for signal transduction in phagocytic cells and for inflammatory and autoimmune diseases, see Prossnitz E R and Ye R D (1997), The N-Formyl Peptide Receptor: a Model for the Study of Chemoattractant Receptor Structure and Function, Pharacol Ther, 74, pp 73–102, the entire contents and disclosure of which is hereby incorporated by reference. The receptor has been cloned and overexpressed in tissue culture cells, solubilized, and assembled with a formyl peptide ligand and G protein to form a high agonist-affinity ternary complex in solution, see Bennett et al. (2001), Real-Time Analysis of G Protein-Coupled Receptor Reconstitution in a Solubilized System, J Biol Chem, 276, pp 22453–22460, the entire contents and disclosure of which is hereby incorporated by reference.

The soluble receptor reconstitutes with ligand, G proteins, and arrestin in a manner that is sensitive to receptor phosphorylation and mutations in both the receptor and G proteins. The assembly may be measured in real-time with fluorescent ligands, and the assemblies are consistent with cellular co-localizations observed by fluorescence confocal microscopy, see Bennett et al. (2001), Real-Time Analysis of G Protein-Coupled Receptor Reconstitution in a Soubilized System, J Biol Chem, 276, pp 22453–22460; Bennett et al. (2001), Partial Phosphorylation of the N-Formyl Peptide Receptor Inhibits G Protein Association Independent of Arrestin Binding, J Biol Chem, 276, pp 49195–49203; and Key et al. (2001), Regulation of Formyl Peptide Receptor Agonist Affinity by Reconstitution with Arrestins and Heterotrimeric G Proteins, J Biol Chem, 276, pp 49204–49212, the entire contents and disclosures of which are hereby incorporated by reference.

While ternary complex assemblies have been the subject of experimental investigation and mathematical modeling over several decades, see Kent et al. (1980), A Quantitative Analysis of β-Adrenergic Receptor Interactions: Resolution of High and Low Affinity States of the Receptor by Computer Modeling of Ligand Binding Data, Mol Pharmacol, 17, pp 14–23, the entire contents and disclosure of which is hereby incorporated by reference, the tools to examine the affinities and kinetics of individual steps in complex formation, disassembly, activation, and termination have only been accessible in a limited way, see Christopoulos A and Kenakin T (2002), G Protein-Coupled Receptor Allosterism and Complexing, Pharmacol Rev, 54, pp 323–374, the entire contents and disclosure of which is hereby incorporated by reference. For rhodopsin, it has been possible to measure complex assembly and disassembly through the spectroscopic signature of the metarhodopsin II-transducin complex, see Mitchell et al. (2001), Optimization of Receptor-G Protein Coupling by Bilayer Lipid Composition I: Kinetics of Rhodopsin-Transducin Binding, J Biol Chem, 276, pp 42801–42806, the entire contents and disclosure of which is hereby incorporated by reference. GPCRs also activate transmembrane channels in the subsecond time frame, see Mark et al. (2000), G Protein Modulation of Recombinant P/Q-Type Calcium Channels by Regulators of G Protein Signaling Proteins, J Physiol, 528, Pt. 1, pp 65–77, the entire contents and disclosure of which is hereby incorporated by reference, where ternary complex dynamics can be inferred from measurements of ion currents. Such measurements have given a $G_t$ (transducin) activation rate of about 120 $s^{-1}$, see Leskov et al. (2000), The Gain of Rod Phototransduction: Reconciliation of Biochemical and Electrophysiological Measurements, Neuron, 27, pp 525–537, the entire contents and disclosure of which is hereby incorporated by reference, probably unique to the visual transduction system, and a $G_q$ (a heterotrimeric G protein in which the α subunit is the q subtype, $α_{-q}$) activation rate of 2 $s^{-1}$, Muldiopadhyay S and Ross E M (1999), Rapid GTP Binding and Hydrolysis by G(q) Promoted by Receptor and GTPase-Activating Proteins, Proc Natl Acad Sci USA, 96, pp 9539–9544, the entire contents and disclosure of which is hereby incorporated by reference. Both surface plasmon resonance, see Rebois (2002), Elucidating Kinetic and Thermodynamic Constants for Interaction of G Protein Subunits and Receptors by Surface Plasmon Resonance Spectoscopy, Methods in Enzymology (Iyengar Ra and Hildebrandt J D, eds), Academic Press, New York, pp 15–42, the entire contents and disclosure of which is hereby incorporated by reference, and flow cytometry, see Nolan J P and Sklar L A (1998), The Emergence of Flow Cytometry for Sensitive, Real-Time Measurements of Molecular Interactions, Nat Biotechnol, 16, pp 633–638, the entire contents and disclosure of which is hereby incorporated by reference, could be general tools for measuring individual rate constants.

G protein coupled receptors (GPCRs) transmit extracellular signals into cells via intracellular G protein heterotrimers (See, Bockaert, J. and Pin, J. P. 1999 *EMBO J.* 18, 1723–1729). Of currently marketed drugs, >30% modulate GPCRs (Wise, et al., 2002, *Drug Discov. Today* 7, 235–246). Only 10% of the 367 human endogenous ligand GPCRs are targeted by current drugs, leaving many future targets. Novel modes of defining the activity of ligands that bind to GPCRs could contribute to the treatment of human disease.

The response to epinephrine or adrenaline is a prototypic GPCR action. Equilibrium binding studies in frog erythrocyte membranes demonstrated homogeneous binding for antagonists, while agonists exhibited two states of agonist affinity (Kent, et al., 1980, *Mol. Pharmacol.* 17, 14–23). The ternary complex model of agonist, receptor, and G protein accounts for the ternary complex exhibiting a higher agonist affinity than the binary complex (DeLean, et al. 1980, *Journal of Biological Chemistry* 255, 7108–7117). Adenylyl cyclase assays define the intrinsic activity, or efficacy, for each compound. Receptors in the high affinity state range from 50% for agonists of the lowest intrinsic activity to 95% for full agonists, the percent correlated roughly with the intrinsic adenylyl cyclase activity of the agonist. The functional consequences of cellular ternary complex formation include the rapid binding of GTP to the Gα subunit, release of the receptor and the Gβγ dimer, and exposure of new Gα and Gβγ surfaces to interact with effectors such as adenylyl cyclase. See, Neer, 1995, *Cell* 80, 249–257. Ternary complex formation for a series of agonists is expected to correlate with adenylyl cyclase activities. More detailed ternary complex formulations take into account the idea that receptors can exist in different activity states. See, Christopoulos Kenakin, 2002, *Pharmacol. Rev.* 54, 323–374).

G protein-coupled receptors used in the instant invention include, but are not limited to, amino acids sequences that encode, or are equivalent or homologous to, GenBank Accession No: NM 002029 (human FPR) and NM000024 (human β2AR) or macaque, cow, cat and dog amino acid sequences corresponding to GenBank Accession Nos. L38905, Z86037, AF192345 and X94608. Numerous other G protein-coupled receptors may be used in the present invention, including for example:

Class A rhodopsin-like receptors such as amine receptors (acetylcholine receptors I–V, adrenoreceptor including alpha I–II and beta receptors I–IV, dopamine receptors I–IV, histamine receptors I–IV, serotonin receptors I–VII, octopamine receptor, trace amine receptor), peptide receptors (angiotensin I and II receptors, bombesin receptor, bradykinin receptors, C5a anaphylatoxin receptors, Fmet-leu-phe receptors, APJ-like receptors, interleukin 8 receptors A and B, chemokine receptors including 1–11, C-X-C 3–5, Bonzo, C-X3-C and XC, CCK receptors A and B, Endothelin, melanocortin receptors, including melanocyte stimulating hormone receptor, adrenocorticotropic hormone receptor, melanocortin hormone receptor, neuropeptide Y 1–6, neurotensin receptor, opioid receptors D, K, M and X, somatostatin receptor 1–5, tachykinin receptors, including substance P (NK1) receptor, substance K (NK2) receptor, neuromedin K (NK3) receptor, vasopressin-like receptors, including vasopressin receptors, oxytoxin receptors, galanin-like receptors, including galanin receptors, allatostatin receptors, GPCR 54 receptors, proteinase-activated like receptors including thrombin receptors, proteinase-activated receptors, orexin & neuropeptide FF receptors, urotensin II receptors, adrenomedullin (G10D) receptors, GPR37/Endothelin B-like receptors, chemokine receptor-like receptors, neuromedin U Like receptors, including neuromedin U receptors and PRXamide receptors, Somatostatin and angiogenin-like peptide including allatostatin C receptors), hormone protein receptors (follicle stimulating hormone receptors, lutropin-choriogonadotropic hormone receptors, thyrotropin receptors, gonadotropin I and II receptors, (rhod) opsin receptors 1–5), olfactory receptors (olfactory II, families 1–12), prostanoid receptor (prostaglandin E2 subtype EP1, E2/D2 subtype EP2, E2 subtype EP3, E2 subtype EP4, F2-alpha, prostacyclin, thromboxane), nucleotide-like receptor (adenosine types 1–3), purinoceptors type Y (adenine, adenine/uridine, uridine), platelet activating factor receptor, gonadotropin-releasing hormone receptor, thyrotropin-releasing hormone and secretagogue receptor, growth hormine secretagogue, melatonin receptor, lysosphingolipid receptor & LPA (EDG) receptor and leukotriene B4 receptor, among others;

Class B Secretin like receptors such as calcitonin receptor, corticotropin releasing factor receptor, gastric inhibitory peptide receptor, glucagon receptors, growth hormone-releasing hormone receptor, parathyroid hormone receptor, PACAP receptors, secretin receptor, vasoactive intestinal polypeptide receptor, diuretic hormone receptor, EMR1 receptor, latrophilin receptor 1–3, ETL receptors, brain-specific angiogenesis inhibitor (BAI) receptor, Methuselah-like proteins (MTH) receptor, cadherin EGF LAG (CELSR); and Class C Metabotropic glutamate/pheromone receptors such as metabotropic glutamate receptor I–III, calcium sensing-like receptor, GABA-B 1–2, and taste receptors (TIR), among others.

The G protein-coupled receptors which are set forth above are described in the GPCR database at the GPCR website (addressed on the world wide web at gpcr.org) are useful in the present invention. Those GPCR proteins have been sequenced and the sequences have been presented on the website, relevant portions of which are incorporated by reference herein. One of ordinary skill in the art may readily adapt the disclosed receptors for use in the present invention using techniques which are well-known in the art.

Many of the above-referenced receptors may be readily solubilized for use in the present invention. Literature references to solubilization of specific GPCRs in active form are known to those well versed in the art. For other GPCRs, solubilization can be performed as outlined in, "Solubilization of Native Membrane Proteins", Hjelmeland, L. M., pp. 253–264, in "Guide to Protein Purification", Ed. Deutscher, M. P., Academic Press, New York, USA (1990), relevant portions of which are incorporated by reference. This chapter gives brief considerations of the essential criteria for solubilization, including a list of seven detergents to be used. In general, membrane preparations are treated with detergent at about 0.1% to about 1% of one or more of the detergents in a physiological salt solution with a mixture of protease inhibitors with mixing for 30 to 60 minutes at 4° C., then centrifuged at 12,000×g to remove insoluble material. The preferred detergents for solubilizing GPRC for use in the present invention include digitonin, sodium cholate, CHAPS, Zwittergent 3–14, octyl glucoside, Triton X-100, Lubrol PX, dodecyl maltoside and mixtures thereof, in many instances with dodecyl maltoside being preferred.

Full length human cDNA clones for the above-referenced GPCR are available in non-proprietary expression vectors directly downstream of a CMV promoter. 318 are listed at the website of Origene (origene.com) and can be purchased from Origene Technologies, Inc. of Rockville, Md. under the GPCR CloneSet™. Other GPCR in expression vectors are also available from other commercial sources.

"GTPγS". A non-hydrolyzable analog of GTP, used in the present invention as an analog of GTP.

Flow cytometry is a tool frequently utilized for cellular analysis. In flow cytometry, a sample containing cells (or equivalent particles) is passed through a line with a sheath fluid, and focused through an orifice, with the objective of cells entering the detector one at a time. These individual cells are irradiated with a light beam, and the intensity of scattered light or fluorescent light from the cells is measured. The ability of flow cytometry to make quantitative measurements on microspheres or cells with continuous kinetic resolution offers an attractive platform for more detailed characterization of compounds of interest.

Traditionally, samples are injected into and suspended within a sheath flow. This type of delivery is disclosed in the following patents: U.S. Pat. No. 5,824,269, to Kosaka et al., entitled Flow Cytometer European Patent No. 46,345, to Connell, entitled Controlled Hydrodynamic Flow in Flow Cytometry Systems; U.S. Pat. No. 5,374,398, to Isami et al., entitled Apparatus for Analyzing Particles; U.S. Pat. No. 5,369,137, to Hansen, entitled Simultaneous Multiple Assays; and U.S. Pat. No. 5,286,452, to Hansen entitled Simultaneous Multiple Assays. The articles Hodder, P. et al., Microfabricated Flow Chamber for Fluorescence-based Chemistries and Stopped-flow Injection Cytometry, Analyst, 122:883–887 (1997); and Nolan, J. et al., A Rapid Mix Flow Cytometer with Subsecond Kinetic Resolution, Cytometry, 21(3):223–229 (1995), disclose the use of syringe pumps for a stopped-flow injection analysis. The sample stream is bounded by the reagent stream. A stopping of the sheath flow causes the core to expand the sheath, thus mixing the sample with the reagent. These inventions do not "compartmentalize" the sample, or prevent mixing. Lack of mixing is especially desirable when screening a multitude of samples, in order to prevent the possibility of cross-contamination.

It is desirable to immobilize the β2-adrenergic receptor-detectable moiety complexes to facilitate separation of complexed from uncomplexed forms of one or both of the proteins, as well as to accommodate automation of the assay. In a purely illustrative example, β2-adrenergic receptor-detectable moiety complexes can be adsorbed onto glutathione sepharose beads (Sigma Chemical, St. Louis, Mo.).

One rapidly expanding field for which such cellular information is useful is that of drug discovery. Large combinatorial libraries that potentially alter or mimic receptor-ligand interactions are screened. To efficiently perform such tasks, rapidity and automation of sample handling are required.

More specifically, the detection of cell-bound fluorescence may be typically performed using a flow cytometer, such as a FACSVantage, FACSVantage® SE, or FACSCalibur flow cytometer (Becton Dickinson Immunocytometry Systems, San Jose, Calif., USA). The lasers chosen for excitation will be determined by the absorption spectrum of the multimeric complex and of any additional fluorophores desired to be detected concurrently in the sample. For example, if the multimeric complex has the spectral characteristics of native GFP or DsRed—e.g., a homotetramer in which the fusion protein subunits all have the native DsRed GFP-like chromophore—a standard argon ion laser with 488 nm line can be used for excitation. For detection, the filter sets and detector types will be chosen according to the emission spectrum of the multimeric complex and of any additional fluorophores desired to be detected in the sample. For example, if the multimeric complex has the spectral characteristics of native DsRed, with emission maximum at about 583 nm, fluorescence emission from the complex can be detected in the FL2 channel using a PE setup.

Bead-based flow cytometric techniques used in the instant invention are descried in more detail hereinafter.

"GFP" or green fluorescent protein means any of the *Aequorea Victoria* fluorescent proteins or polynucleotides, including all mutants of such proteins or polynucleotides. Examples of GFP's include but are not limited to those GFP's disclosed in U.S. Pat. Nos. 5,625,048 and 5,777,048.

"β2-adrenergic receptor-detectable moiety complexes" include fusion proteins comprising a β2-adrenergic receptor and a detectable moiety, preferably a green fluorescent protein (β2AR-GFP). β2-adrenergic receptor-detectable moiety complexes used in the instant invention include, but are not limited to, amino acids sequences that encode, or are equivalent or homologous to, GenBank Accession No: NM-000024, fused to the GFPs referred to above.

"Detectable moiety" means any fluorophore label on a first, 'donor' molecule that is selected such that its emitted fluorescent energy can be detected by fluorimetry, including by flow cytometry. In another form, the fluorescent energy will be absorbed by a fluorescent label on a second, 'acceptor' molecule, which in turn is able to fluoresce due to the absorbed energy. Detectable moieties include but are not limited to GFP's and red fluorescent proteins (RFP's) such as DsRed and DsRed2 available from BD Biosciences. More specifically, the subject fluorescent proteins of the present invention (as well as other components of the subject invention described above) find use in a variety of different applications, where such applications include, but are not limited to, the following. The first application of interest is direct detection of particle-associated fluorescence by flow cytometry. A second is the use of the subject proteins in fluorescence resonance energy transfer (FRET) applications. In these applications, the subject proteins serve as donor and/or acceptors in combination with a second fluorescent protein or dye, e.g., a fluorescent protein as described in Matz et al., Nature Biotechnology (October 1999) 17:969–973, a green fluorescent protein from *Aequoria victoria* or fluorescent mutant thereof, e.g., as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference, other fluorescent dyes, e.g., coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc., chemilumescent dyes, e.g., luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference.

Fluorescence brightness of a particular fluorescent protein is determined by its quantum yield multiplied by maximal extinction coefficient. Brightness of a chromoprotein may be expressed by its maximal extinction coefficient. In some embodiments, the subject nucleic acids encoded polypeptides show substantially the same or greater brightness in an assay than a reference protein, e.g., compared to the corresponding wild type protein, e.g., a mutant may be at least about 10%, at least about 20%, at least about 30%, at least about 40%, at least about 50%, at least about 60%, at least about 70%, at least about 80%, at least about 90%, at least about 100% (or two-fold), at least about 150%, at least about three-fold, or at least about four-fold, or more, brighter in the assay than the reference protein. Brightness can be measured using any known method, including, but not limited to, visual screening, spectrophotometry, spectrofluorometry, fluorescent microscopy, by fluorescence activated cell sorting (FACS) machines, etc. In some instances, brightness of a subject mutant protein in an assay can be visually compared to the brightness of a reference protein in an assay of the same type.

Changes in the interaction between the partner portions of fusion proteins used in the invention can be modulated, e.g., by ligands or test compounds, and can be monitored by a change in the ratio of light emitted by the bioluminescent and fluorescent portions of the fusion proteins. In this application, the subject proteins serve as donor and/or acceptor proteins.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

Nucleic acids may encode fusion proteins in which subject proteins, or fragments thereof, which are fused to a second protein, e.g., a degradation sequence, a signal peptide, a protein of interest (i.e., a protein being studied), etc. Fusion proteins may comprise a subject polypeptide, or fragment thereof, and a non-non-aggregating polypeptide ("the fusion partner") fused in-frame at the N-terminus and/or C-terminus of the subject polypeptide. Fusion partners include, but are not limited to, polypeptides that can bind antibody specific to the fusion partner (e.g., epitope tags); antibodies or binding fragments thereof; polypeptides that provide a catalytic function or induce a cellular response; ligands or receptors or mimetics thereof; and the like. In such fusion proteins, the fusion partner is generally not naturally associated with the subject non-aggregating protein portion of the fusion protein "Expression cassettes" or systems are used to synthesize proteins used in the invention. For expression, the gene product encoded by a polynucleotide used in the invention is expressed in any convenient expression system, including, for example, bacterial, yeast, insect, amphibian and mammalian systems. Suitable vectors and host cells are described in U.S. Pat. No. 5,654,173. In the expression vector, a subject polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked. under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as described above.

β2AR-GFP fusion protein was used in one embodiment of the invention. We derivatized beads to discriminate GPCR assemblies sensitive to full and partial agonists, and antagonists. Beads displayed dihydroalprenolol (DHA beads), following earlier work (11). DHA beads bound detergent-solubilized β2AR-GFP with $K_d$~3.4 nM. Competition with agonists gave $K_d$ values for these ligands similar to published values. Beads displaying Gαsβ1γ2 hexahistidine-tagged proteins bound agonist: β2AR-GFP binary complexes in a ternary complex. For full and partial agonists, the maximal amount of ternary complex correlated with agonist efficacy. Interestingly, ternary complexes formed by both full and partial agonists were disassembled by GTPγS at the same rate, suggesting that partial agonism depends upon ternary complex assembly rather than disassembly. The affinity of β2AR-GFP for G protein was measured by competition of soluble G protein, creating a fairly complete description of the assemblies. Moreover, these well-characterized assemblies can be assayed simultaneously, in a manner consistent with small volume, real-time, high throughput discrimination of agonists and antagonists in a primary screen and resolution of partial agonists in a secondary dose-response screen.

For the purposes of the present invention, the term "ligand" refers broadly to the conventional meaning of the term ligand i.e. a molecule, ion or atom that is capable of forming a complex with another molecule, ion or atom.

In certain aspects of the present invention, a ligand of a GPCR is bonded to a bead ("ligand beads") which may be used in bead based flow cytometry or other high throughput bead based screening system. Ligand beads may be generalized from the DHA (dihydroalprenolol) beads used by example in this application, to include all ligands known for GPCRs, in the form of a ligand attached to the beads by methods including and similar to those developed for affinity chromatography. The application of a GPCR to a bead for use in flow cytometry is well known in the art. This field includes, but is not limited to, conjugation of small molecules, carbohydrates, nucleic acids, or proteins to activated beads as described in the present application, or to activated beads supplied by various manufacturers by methods described by those manufacturers, or to beads activated by chemistry including and similar to those described in, "Bioconjugate Techniques," Hermanson, G. T., Academic Press, New York, USA (1996).

For the purposes of the present invention, the term "epitope-recognizing bead" refers to a bead bearing a chemical structure that binds to an epitope, or to any structure bearing that epitope.

For the purposes of the present invention, the term "epitope-bearing G protein subunit" refers to any Gα, Gβ, or Gγ that has any additional structure (the epitope) attached to it.

For the purposes of the present invention, the term "G protein heterotrimer" refers to any combination of (Gα+Gβ+Gγ).

For the purposes of the present invention, the term "receptor" refers to a molecule on a cell that can bind another molecule (ligand) outside the cell.

For the purposes of the present invention, the term "G protein coupled receptor" can include a seven transmembrane protein on a cell that can bind another molecule (ligand) outside the cell and a G protein inside the cell.

For the purposes of the present invention, the term "G protein coupled receptor molecular assemblies" include the binary ligand and receptor assembly, the ternary ligand-receptor-G protein assembly, or the ternary ligand-phosphorylated receptor-arrestin assembly.

G protein coupled receptors form a ternary complex of ligand, receptor, and G protein heterotrimer (LRG) during signal transduction from the outside to the inside of a cell. The present invention provides a homogeneous, small volume bead-based approach compatible with high throughput flow cytometry, which allows evaluation of G protein coupled receptor molecular assemblies. Dextran beads were derivatized to carry chelated nickel to bind hexahistidine-tagged green fluorescent protein (GFP) and hexahistidine-tagged G proteins. Ternary complexes were assembled on these beads using fluorescent ligand with wild type receptor or a receptor-Giα2 fusion protein, and with a nonfluorescent ligand and receptor-GFP fusion protein. Streptavidin coated polystyrene beads used biotinylated anti-FLAG antibodies to bind FLAG-tagged G proteins for ternary complex assembly. Validation was achieved by showing time and concentration dependence of ternary complex formation. Affinity measurements of ligand for receptor on particles, of the ligand-receptor complex for G protein on the particles, and receptor-Giα2 fusion protein for Gβγ, were consistent with comparable assemblies in detergent suspension. Performance was assessed in applications representing the potential of these assemblies for ternary complex mechanisms. First, the relationship was shown for a family of ligands between LR affinity and LRG affinity. Second, RGS4 and RGS8 were shown to alter the assembly characteristics of the receptor-Giα2 with Gβγ on the beads in a manner consistent with GTP turnover. Third, the potential of kinetic measurements to allow observation of individual steps of ternary complex disassembly was shown.

The present invention provides for preparing epitope-recognizing beads, which bind to epitope-bearing G protein subunits to form a bead-borne heterotrimeric G protein, solubilizing a GPCR, allowing the GPCR to bind to the bead-borne G protein in the presence of a ligand, and detecting the formation of a stable ligand-receptor-G protein (LRG) complex by flow cytometry. Beads may be used that recognize both the FLAG and six-histidine (H6) epitopes. G protein βγ subunits tagged with both epitopes may be used, and supplemented with α subunits to form a heterotrimeric G protein (αβγ) on the beads. Several methods may be used to detect LRG formation by flow cytometry: in a first method, soluble formyl peptide receptor (FPR) plus a fluorescent ligand are added to the beads, and in a second method, a chimeric soluble formyl peptide receptor-green fluorescent protein (FPR-GFP) plus a nonfluorescent ligand are added to the beads. FPR-G protein α subunit fusion proteins have also been detected using the methods of the present invention.

The epitope-tagged βγ subunits assemble with α subunits to form heterotrimeric G protein on beads, and bind receptor in a dose dependent way. In one form of the assay, the binding of the receptor is visualized with fluorescent ligand. The complex dissociates with addition of GTPγS, which shows that the complex involves a G protein. In a second form of the assay, the beads are incubated with a chimeric or fusion protein consisting of a GPCR and green fluorescent protein (GFP), and inclusion of ligand allows the chimeric GPCR-GFP to bind to the bead. This complex also dissociates in the presence of GTPγS. In the third form of the assay, the beads are incubated with a chimeric protein consisting of a GPCR and G protein α subunit, and inclusion of a fluorescent ligand allows the chimeric receptor to bind to the bead. This complex also dissociates in the presence of GTPγS.

The H6 and FLAG epitopes do not interfere with the assembly of the complex. Epitope-tagged α and β subunits may be used according to the methods of the present invention and these approaches may be generalized to all epitopes.

Nickel chelate beads (latex, silica, and dextran) bind other proteins non-specifically, leading to high nonspecific, or background, signals when fluorescent G proteins are added; the smaller fluorescent ligand used in particular embodiments of the present invention has lower nonspecific binding. The FLAG epitopes were captured using a more complex bead, which was commercially coated with streptavidin, to which biotinylated anti-FLAG antibodies were bound. This second bead type generalizes the bead type and the epitope type, and may give improved (lower) background binding, in particular, when fluorescent proteins are used for detection.

Using chimeric GPCR-GFPs means that receptors that do not already have a fluorescent ligand available may also be used. This concept is generalizable to other GPCRs following the teachings of the present invention.

Using chimeric GPCR-GFPs for a receptor with no known ligand (an orphan receptor), one could screen for a ligand that would make the bead fluorescent, thereby defined as an agonist. Once this agonist is found, antagonists may be found by screening for agents that block the agonist-induced bead fluorescence. The human genome project produced many seven-transmembrane open reading frames, which presumably encode GPCR for which no ligand is yet known. Obtaining a ligand using this general methodology is well within the routine practitioner's skill in the art.

G proteins are expressed in bacteria in high concentration, with purification helped by the epitope tag, and are used at low concentration (nM), thus minimizing costs. The receptors may be prepared in bulk, by solubilizing crude membrane preparations from transfected cells, and are also used in low concentration.

Assays of the present invention may be multiplexed in several useful ways. For instance, it is possible to use colored beads, each bearing a different combination of G protein subunits (αβγ), to determine the specificity of αβγ for a given LRG assembly. For example, chimeric FPR-αi2 interacts well with β1γ2-bearing beads, but less well with β4γ2-bearing beads.

Applying other proteins to beads, such as a truncated arrestin, may provide for detection of receptors that were activated but not able to couple to G protein. Applying full length arrestin to beads could allow for the detection of phosphorylated receptors.

A goal of the present invention was to develop a general approach toward GPCR assays that would provide useful mechanisms in the broad field of high throughput screening for drug discovery.

Because GPCRs are prominent targets in drug discovery, the present invention provides generic assembly capabilities for GPCRs, using a homogeneous approach in which a flow cytometer may distinguish fluorescent molecules associated with a particle from those free in solution around the particle, see Sklar et al. (2002), Flow Cytometric Analysis of Ligand-Receptor Interactions and Molecular Assemblies, Ann Rev Biophys Biomol Struct, 31, pp 97–119, the entire contents and disclosure of which is hereby incorporated by reference. Based on solubilization in dodecyl maltoside, it has been shown that an epitope-tagged receptor could be associated with particles and analyzed by flow cytometry, using a fluorescent ligand to detect the assembled complex, see Sklar et al. (2000), Solubilization and Display of G Protein-Coupled Receptors on Beads for Real-Time Fluorescence and Flow Cytometric Analysis, Biotechniques, 28, pp 975–976, the entire contents and disclosure of which is hereby incorporated by reference. Such assemblies may further be adapted for analysis of ternary complex formation involving both signal transduction and termination partners, and these approaches would be compatible with high throughput flow cytometry, Kuckuck et al. (2001), High Throughput Flow Cytometry, Cytometry, 44, pp 83–90, the entire contents and disclosure of which is hereby incorporated by reference. This approach suffers from two important limitations. First, detecting signaling assemblies when the receptor is anchored to the particles is difficult. Second, in certain situations, detection of the assembly may require a fluorescent ligand to detect receptor affinity changes induced by subsequent receptor assemblies.

Both of the above-identified limitations have been addressed by the present invention. The present invention provides for the formation of high affinity complexes of the FPR with ligands on beads that have been coated with epitope-tagged G protein subunits. Ternary complexes have been assembled using three different receptor constructs (wild type, FPR-$G_i\alpha$ fusion, and FPR-GFP fusion), two types of epitope-tagged G proteins, two α and β subunits, and two types of beads. Estimates of the affinities of ligand for receptor, ligand-receptor complex for G protein, and α for βγ are appropriate for the detergent-solublilized receptor. LR and LRG formation for a family of ligands have been evaluated, the rate at which different receptor forms dissociate was measured, and the impact of RGS on an assembly involving the Giα2-receptor fusion protein was evaluated.

EXAMPLE 1

Experimental Procedures

Reagents and Cell Culture. The cloning of the FPR, see Boulay et al. (1990), The Human N-Formylpeptide Receptor: Characterization of Two CDNA Isolates and Evidence for a New Subfamily of G-Protein-Coupled Receptors, Biochemistry, 29, pp 11123–11133, the entire contents and disclosure of which is hereby incorporated by reference, and its expression in U937 cells have been described, see Kew et al. (1997), Undifferentiated U937 Cells Transfected with Chemoattractant Receptors: a Model System to Investigate Chemotactic Mechanisms and Receptor Structure/Function Relationships, J Leukoc Biol, 61, pp 329–337, the entire contents and disclosure of which is hereby incorporated by reference. Plasticware was from VWR, and chemicals and reagents were from Sigma unless otherwise noted. The cells were grown in tissue culture treated flasks (Corning Inc.; Corning, N.Y.) in RPMI 1640 (Hyclone; Logan, Utah) with 10% fetal bovine serum (Hyclone), 2 mM glutamine, 10 mM HEPES, 10 units/ml penicillin and 2 µg/ml streptomycin. The cultures were grown at 37° C. with 5% $CO_2$ and passaged from subconfluent cultures every 3–4 days by reseeding at $2\times10^5$ cells/ml. The cells were expanded for membrane preparations in 1 liter baffled Pyrex spinner flasks by seeding at $2\times10^5$ cells/ml, equilibrated with 5% $CO_2$, then sealed and incubated at 37° C., with stirring. The cells were harvested when the density reached $10^6$ cells/ml. Receptor expression level decreased with passage, so freshly thawed cells were incubated with 10 nM fMLFK-FITC and sorted for the highest 5% expression to maintain 200,000–500,000 receptors/cell as needed, then frozen in aliquots for future use.

Generation of FPR-Giα2 and FPR-GFP Fusion Constructs. The human FPR (containing an EcoRI site and a NotI site embedded within the 5' and 3' primers, respectively) and rat Giα2 (containing a NotI site and an EcoRI site embedded within the 5' and 3' primers, respectively) were amplified by standard PCR protocols using Platinum™ Taq DNA polymerase (Perkin-Elmer; Norwalk, Conn.). The digested PCR products were ligated into EcoRI-digested and phosphatase-treated pSFFV.Neo and screened for orientation of the insert. Appropriate clones were confirmed by dideoxy sequence analysis. The final fusion protein contained three alanine residues between the last amino acid of the FPR and the first amino acid of the Giα2 protein-reading frame. A similar strategy was used to construct a plasmid to produce the FPR-GFP fusion protein using HindIII, NotI, and Xba, which again had three alanine residues between the last amino acid of the FPR and the first amino acid of the GFP (Clontech's EGFP, optimized for fluorescence using standard fluorescein filter sets; now part of BD Biosciences, Palo Alto, Calif.).

Membrane Preparation by Nitrogen Cavitation. The procedure was performed at 4° C. Cells were harvested by centrifugation at 450×g for 5 minutes and resuspended in cavitation buffer (10 mM HEPES, pH 7.3, 100 mM KCl, 3 mM $NaCl_2$, 3.5 mM $MgCl_2$, and 1× protease inhibitor cocktail 1 (Calbiochem; San Diego, Calif.)) at a density of $10^7$ cells/ml. This cell suspension was placed in a nitrogen bomb and pressurized to 450 p.s.i. for 20 minutes, after which the suspension was slowly released into a sample tube. Unbroken cells and nuclei were removed by centrifugation at 1000×g for 5 min. The membranes in the supernatant were pelleted by centrifugation twice at 135,000×g for 30 min, resuspended in buffer (25 mM HEPES, pH 7.5, 200 mM sucrose), and then aliquotted at $10^8$ cell equivalents in 0.5 ml, and stored at –80° C.

Solubilization of the FPR. An aliquot of membrane was thawed, 700 µl of buffer A (30 mM HEPES, pH 7.5, 100 mM KCl, 20 mM NaCl, 1 mM $MgCl_2$) was added, and the membranes were removed from the sucrose by centrifugation in a microfuge for 15 minutes. The supernatant was removed, the pellet was resuspended in 220 µl of buffer A by 10 passes back and forth through a 25 G needle, 25 µl of 10% dodecyl maltoside and 2.5 µl of 100× protease inhibitor cocktail were added, and the suspension was gently mixed for 2 hours at 7° C. The unsolubilized material was removed by centrifugation as above for 15 minutes, giving a supernatant of solubilized FPR at $4\times10^8$ cell equivalents/ml (about 5 mg/ml protein), and used within 6 hours. Solubilization was essentially 100%, so that 150,000 receptors/cell resulted in about 100 nM soluble FPR using this procedure. For FPR-GFP(RF) preparations, 2 µl of $10^{-4}$ M ligand (fMLFFGGK) was added to 200 µl of the preparation when desired to give quantitative conversion of $R^F$ to $LR^F$ or FPR, $L^F$ (fMLFF-FITC) was added when desired at greater than the concentration of receptor to ensure nearly quantitative conversion of R to $L^F R$, while keeping the concentration of free ligand low, to minimize nonspecific binding to the beads. The solublilized receptor preparation retained >90% activity after freezing at –80° C.

Use of Formyl Peptides. $L^F$ (fMLFK-FITC) was obtained from Bachem (King of Prussia, Pa.). Typically, 1 mg was dissolved in 10 ml of methanol, and 30 µl of the solution at about 0.1 mM was diluted in 3 ml of buffer A with 0.1 mg/ml BSA to obtain the absorbance at 495 nm. The concentration of $L^F$ was calculated using an extinction coefficient of 76,000 $M^{-1}$ $cm^{-1}$. The methanol solution was aliquotted into microfuge tubes to give $10^{-8}$ mol of $L^F$, and dried in a Speedvac. These aliquots were stored at –20° C., dissolved in 10 µl of DMSO to give $10^{-3}$ M $L^F$, then diluted at least 100-fold in buffer A with 1 mg/ml BSA to give $10^{-5}$ M $L^F$.

(fMLFFGGK) was synthesized by Commonwealth Biotechnologies, Inc. (Richmond, Va.). Dry peptide (8.2 mg) was dissolved in a final volume of 1 ml of acetic acid/water: 100 µl of acetic acid dissolved the powder, then 900 µl of 50% acetic acid was added. This was diluted 100-fold into buffer A, which was brought back to pH 7.5 with NaOH, giving $10^{-4}$ M L. It was aliquotted into 1 ml and 10 µl aliquots, stored at –20° C., and thawed fresh each day.

Synthesis of Dextran Chelate Nickel (DCNi) Beads. Superdex Peptide beads, a crosslinked agarose/dextran matrix with an exclusion limit of 7,000 Daltons and an average size of 13 µm, were removed from a packed column purchased from Amersham Pharmnacia Biotech. (Superdex 30 Prep Grade beads, average size 34 µm, are also compatible with flow cytometric analysis.) The beads were activated with a water-soluble bis-epoxide, and then coupled to a chelator that contained an amino group, see Sundberg L and Porath J (1974), Preparation of Adsorbents for Biospecific Affinity Chromatography: Attachment of Group-Containing Ligands to Insoluble Polymers by Means of Bifunctional Oxiranes, J Chromatogr, 90, pp 87–98, the entire contents and disclosure of which is hereby incorporated by reference. 12 ml of a 50% slurry of beads was reduced to a wet cake by vacuum filtration using a 60 ml coarse sintered glass funnel, and then washed three times with 50 ml of water to remove the ethanol in which the beads were supplied. The wet cake was transferred to a 25 ml Erlenmeyer flask, the funnel was rinsed with 5 ml of water, and this rinse was added to the flask. One ml of 5 M NaOH, 10 mg of NaBH$_4$, and 5 ml of 1,4-butanediol diglycidyl ether (Sigma) were then added, and the flask was rotated to keep the beads in suspension for 8 hrs at 37° C.; some bubbling occurred in the first hour. The beads were washed by vacuum filtration twice with water, twice with phosphate buffered saline (PBS), twice with water again, then stored for up to one week at 4° C., or for two months dried at 4° C. One settled volume of these epoxy-activated beads was coupled with one volume of the chelator N$_\alpha$,N$_\alpha$-bis(carboxymethyl)-L-lysine (Fluka) in 0.2 M Na$_2$CO$_3$, pH 11, adjusting the pH again after addition to the beads. 2.5 mM, 25 mM, and 250 mM chelator was used in three different reactions to obtain different substitution levels on the beads. The coupling proceeded at 22° C. overnight with gentle mixing to keep the beads in suspension. The beads were washed as above and then treated with ten volumes of 0.1 M NiCl$_2$ for 1 minute in column or batch mode; the two highest-substituted batches became visibly blue/green, while the lightly-substituted batch remained white. The beads were rinsed with water and PBS. Atomic absorption analysis of the three samples showed the content of Ni to be 1.5 mM, 16 mM, and 30 mM for the settled beads: substitution appeared proportional to the concentration of amino compound up to 25 mM in the reaction, then began to saturate.

Coating DCNi beads With H6-Tagged G Proteins. N-terminal hexahistidine-tagged β2 subunit (H6γ2) CDNA was created by standard recombinant DNA techniques. A β1H6γ2 dimer was produced by coexpression of a β1 subunit and a H6γ2 subunit in Sf9 insect cells, and the dimer was purified essentially as previously described, see Kozasa T and Gilman A G (1995), Purification of Recombinant G Proteins from Sf9 Cells by Hexahistidine Tagging of Associated Subunits, Characterization of α 12 and Inhibition of Adenylyl Cyclase by α z, J Biol Chem, 270, pp 1734–1741, the entire contents and disclosure of which is hereby incorporated by reference, using a Ni chelate column followed by a Mono S column (Amersham Biosciences). The β1H6γ2 preparation was 46 μM, and 14 μl was incubated with 15 μl of 42 μM αi3 subunit (Calbiochem) and 44 μl of G buffer (0.1% dodecyl maltoside, 30 mM HEPES, pH 7.5, 100 mM KCl, 20 mM NaCl, 1 mM MgCl$_2$, and 1 mM DTT) for 5 minutes on ice to allow the G protein heterotrimer to form, then frozen in 2 μl (17 pmol) aliquots. After thawing, 2.5 μl of a 50% slurry of DCNi beads (2.5×10$^8$ beads/ml) was added, and the volume was brought to 100 μl with G buffer. The beads were kept suspended with rotation at 7° C. for one hour, then pelleted by centrifugation and brought to 50 μl with G buffer. This gave 1.2×10$^7$ beads/ml, nominally coated with 18 million G protein αβH6γ per bead, with an unknown amount left on the beads in an active orientation (for comparison, assuming that random fall results in about 50% coverage, one expects about 7 million BSA molecules per 13 μm sphere); 2 μl of bead suspension was used per 10 μl assay, consuming about 0.7 pmol Gαβγ per assay on 24,000 beads. The beads retained more than 90% of their binding activity after freezing at −80° C. When the FPR-αi2 fusion protein was used for an assembly, only the β1H6γ2 dimer was used to coat the DCNi beads as above.

Standard LRG Assembly Assay. The standard 10 μl assay consisted of 2 μl of water or 10$^{-4}$ M GTPγS, 6 μl of soluble receptor preparation with or without ligand, and 2 μl of beads prepared as above, with 0.7 pmol G protein used per assay, and an unknown fraction left on the beads in the proper orientation. For FPR and R-αi2 assemblies, L$^F$ (fMLFK-FITC) was added in excess of receptor to ensure that essentially all the receptor was bound. For FPR-GFP assembly, 10$^{-6}$ M L (fMLFFGGK) was added to the receptor preparation to ensure that essentially all the receptor was bound. Each mixture was mixed by pipetting to ensure a uniform starting suspension of the beads in 96 V-well plates (Costar), and then mixed at low speed on a vortex mixer at 7° for two hours. The 10 μl assays were individually brought to 200 μl with 0.1% dodecyl maltoside in buffer A in 12×75 mm tubes for flow cytometric measurement of fluorescence of the beads. LRG assembly was defined as the difference between fluorescence without GTPγS and that with GTPγS. All determinations were done in duplicate. For assays with the FPR-αi2 chimera, a low amount of GTP was present (vide infra), and for the demonstration of RGS activity, both GTP and RGS proteins were added at the concentrations shown in FIGS. 6A and 6B, see also Lan et al. (2000), Rapid Kinetics of Regulator of G-Protein Signaling (RGS)-Mediated Gαi and Gαo Deactivation: Gα Specificity of RGS4 and RGS7, J Biol Chem, 275, pp 33497–33503, the entire contents and disclosure of which is hereby incorporated by reference.

Flow Cytometry Analysis and Calibration. Flow cytometry was carried out using FACScan cytometers (Becton-Dickinson), obtaining 3,000 gated events (see FIG. 2A for a typical gate of the DCNi beads) for a sample to obtain a mean channel fluorescence (MCF). These numbers were converted to the mean equivalent of soluble fluorophores on a bead using calibrated beads (Bangs Labs). The number of receptors on a bead was determined by multiplying this by 1.22 to reflect the smaller fluorescence of conjugated fluorescein compared to free fluorescein, see Buranda et al. (2001), Detection of Epitope-Tagged Proteins in Flow Cytometry: Fluorescence Resonance Energy Transfer-Based Assays on Beads with Femtomole Resolution, Anal Biochem, 298, pp 151–162, the entire contents and disclosure of which is hereby incorporated by reference. Since GFP gave a lower molar fluorescence (quantum yield) than normal L$^F$, the mean equivalent of soluble GFP fluorophores was multiplied by 2.1 to calculate the number of GFP molecules on a bead. Note that in the β2AR-GFP work, new GFP calibration beads became available, and that work used the GFP calibration beads for determination of GFP/bead.

Coating Streptavidin-Coated Beads With Biotinylated Anti-FLAG Antibody and FLAG-Tagged G Proteins. Twenty microliters of 6.2 μm diameter streptavidin-coated polystyrene beads at 4×10$^7$ beads/ml (Spherotech Inc., Libertyville, Ill.) were mixed with 20 μl of 1 mg/ml biotinylated anti-FLAG antibody (Sigma) for 2 hours at 4° C., and then washed three times in buffer to give about 9×10$^6$ FLAG-FITC binding sites per bead at 4,000 beads/μl, see Buranda et al. (2001), Detection of Epitope-Tagged Proteins in Flow Cytometry: Fluorescence Resonance Energy Transfer-Based Assays on Beads with Femtomole Resolution, Anal Biochem, 298, pp 151–162, the entire contents and disclosure of which is hereby incorporated by reference. G protein γ2-H6-FLAG subunits were co-expressed with β4 subunits in Sf9 cells, which were extracted as described, see McIntire et al. (2001), The G Protein β Subunit is a Determinant in the Coupling of Gs to the β 1-Adrenergic and A2a Adenosine Receptors, J Biol Chem, 276, pp 15801–15809, the entire contents and disclosure of which is hereby incorporated by reference. The extract was loaded on a 3 ml FLAG column (Sigma) and eluted with FLAG peptide according to the manufacturer's instructions. The eluate was immobilized on a 4 ml nickel column, washed with increasing concentrations of salt and detergent, then eluted with imidazole. The eluate was immobilized on a 15Q column (Amersham Biosciences), eluted with salt, concentrated with a Centricon 30, aliquotted, and stored at −80° C. This βγ preparation was combined with equimolar αi3 (Calbiochem) as above. Fifty microliters of the beads were mixed with 1 µl of 3.4 µM αi3β4γ2-FLAG-H6 for 1 hour, spun, and resuspended in 40 µl buffer, to give beads nominally coated with nine million G protein αβγ per bead; 2 µl of this suspension was used per assay, about 0.17 pmol per assay, on 10,000 beads. These beads are smaller than the DCNi beads, and easier to keep in suspension.

Kinetic LRG Disassembly. LRG was assembled according to one of the three methods above, depending on the receptor type. The 10 µl assay was brought to 200 µl as usual at the flow cytometer and an initial fluorescence was recorded for 20 seconds, then the tube was removed, 2 µl of 0.01 M GTPγS or 6 µM anti-FITC antibody was added at 25 seconds, and the tube was put back on the flow cytometer for dynamic measurement of fluorescence. A 2 mm×5 mm stir bar (Bel-Art; Pequaimock, N.J.) was driven by a magnetic stirrer brought near the tube to keep the beads in suspension. The time course data were converted to ASCII format using the Facsquery program (developed by Bruce Edwards), which puts the raw data into bins of the desired time period with an MCF for each bin in an Excel file. Dissociation curves of this series of MCF values were analyzed using Prism (Graphpad Software; San Diego, Calif.).

Figure 8A:
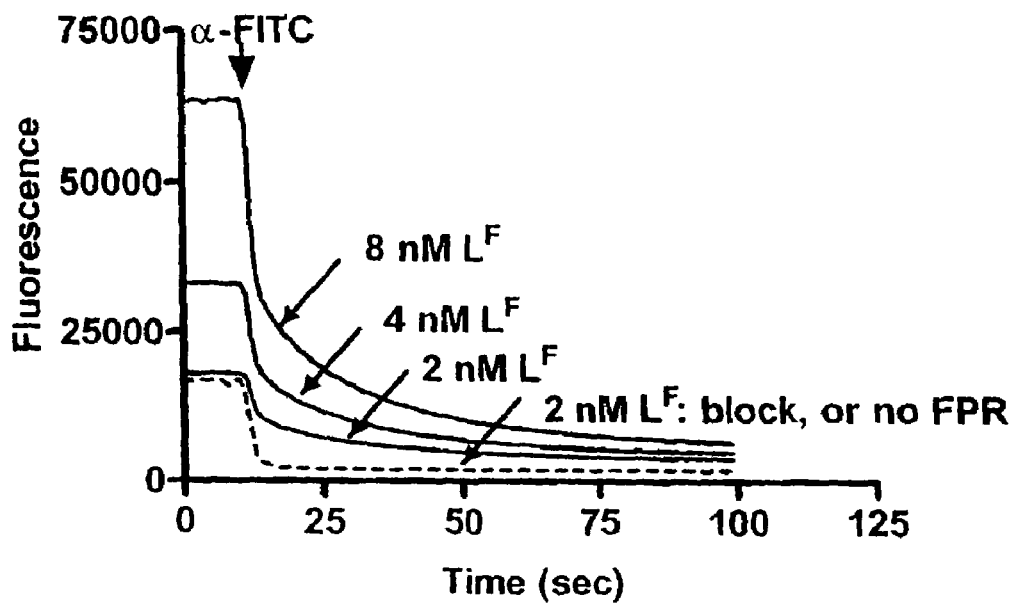
In FIG. 8A, fluorescent ligand ($L^F$) was incubated in the presence of an unknown amount of solubilized formyl peptide receptor in 200 μl aliquots in a spectrofluorimeter with stirring as described in the experimental procedures discussed herein. After obtaining an initial fluorescence, an antibody that quenched the fluorescence of free $L^F$ was added, and the resulting fluorescence was monitored over time. The dotted line, representing 2 nM $L^F$ added to a cuvet without receptor, has been shifted down for clarity. Two traces are shown for the addition of 2 nM $L^F$: the solid line shows the fluorescence for a solution containing receptor, while the dotted line shows the fluorescence for a solution without receptor (or with blocked receptor). The point at which the receptor-containing line with 2 nM $L^F$ departed from the receptor-free (or blocked receptor) dotted line measured the proportion of free ligand (above the point) and receptor-bound ligand (below the point). This pair of values defined the first square in FIG. 1B, at 0.7 nM $L^F$ bound, 1.3 nM $L^F$ free.

Spectrofluorimetric Analysis of Soluble Complexes. Fluorescence was measured with an SLM 8000 spectrofluorimeter (SLM Instruments, Inc.) using the photon counting mode. The sample holder was fitted with a cylindrical cuvette adapter, which allowed the use of 200 µl samples in 7 mm×45 mm cylindrical cuvettes (Sienco; Wheat Ridge, Colo.), stirred with 2×5 mm stir bars (Bel-Art). Excitation was at 490 nm, and stray light was reduced with a 490+/−10 nm filter (Corion; now part of Spectra-Physics, Franklin, Mass.). Emission was monitored using a 520+/−10 nm filter (Corion) and a 500 nm long-pass filter (Kopp; Pittsburg, Pa.). Additions to samples during kinetic measurements were made through an injection port on the top of the sample holder with 10 µl glass syringes (Hamilton; Reno, Nev.). For each concentration of fluorescent ligand used, a sample of solubilized proteins from membranes containing receptor and membranes without receptor were measured, typically 5 µl of a 60 nM R preparation to give 3 nM R, as shown in FIG. 8A for 2 nM $L^F$. Although these lines have been shifted in this figure for clarity, inspection showed the point at which the receptor-containing curve deviated from the control curve, below which represented the amount of the 2 nM ligand which was bound to the receptor (in this case, 0.7 nM), and above which represented the ligand which was free (in this case, 1.3 nM): these two numbers gave the first point in FIG. 8B. For accurate analysis, and for kinetic dissociation analysis, the percent of the control curve corresponding to the percent free ligand was subtracted from the receptor-containing curve.

Results

Figure 8B:
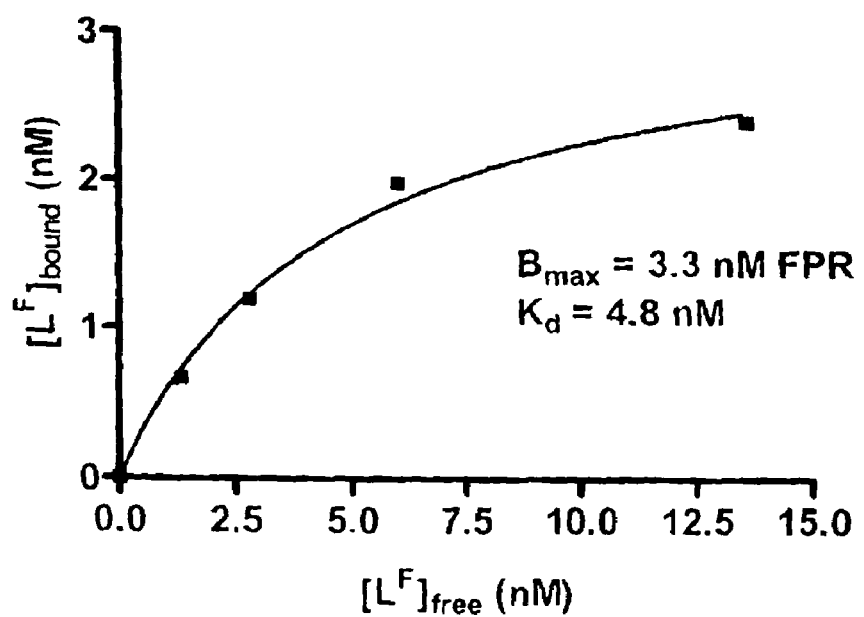
In FIG. 8B, concentrations of free $L^F$ and receptor-bound $L^F$ were obtained for each beginning concentration of $L^F$. These paired values were plotted to obtain the dissociation constant of the $L^F$ for the receptor and the concentration of the receptor.

Soluble FPR Assay. The presence of LR and LRG complexes in solution has been shown using a fluorimetric assay in which FPR are quantitatively solubilized, see Bennett et al. (2001), Real-Time Analysis of G Protein-Coupled Receptor Reconstitution in a Soubilized System, J Biol Chem, 276, pp 22453–22460; Bennett et al. (2001), Partial Plosphorylation of the N-Formyl Peptide Receptor Inhibits G Protein Association Independent of Arrestin Binding, J Biol Chem, 276, pp 49195–49203; Key et al. (2001), Regulation of Formyl Peptide Receptor Agonist Affinity by Reconstitution with Arrestins and Heterotrimeric G Proteins, J Biol Chem, 276, pp 49204–49212; and Sklar et al. (2000), Solubilization and Display of G Protein-Coupled Receptors on Beads for Real-Time Fluorescence and Flow Cytometric Analysis, Biotechniques, 28, pp 975–976, the entire contents and disclosures of which are hereby incorporated by reference. The detection of LR in a spectrofluorimeter was accomplished with a fluoresceinated ligand, formyl-MLFK-FITC ($L^F$), and an anti-FITC antibody, which quenched the fluorescence of the FITC on the ligand about 91% when it was bound. Since the FPR quenched the fluorescence of the ligand minimally, addition of ligand to a detergent-solubilized receptor preparation gave a high initial fluorescence, some of which was due to bound $L^F$, and some of which was due to free $L^F$ (FIG. 8A). The free ligand and bound ligand were discriminated using an antibody to fluorescein that rapidly quenched only the free ligand. The dissociation halftime for $L^F$ was 14 seconds at room temperature. FIG. 8B shows a plot of the data from FIG. 8A in the form of a ligand-binding curve, from which one can obtain a $K_d$ of 4.8 nM, and a $B_{max}$ of 3.3 nM FPR. The dissociation rate, its insensitivity to guanine nucleotide (not shown), and $K_d$ were consistent with the LR but not the LRG form of the receptor.

Soluble Receptor Display on Beads. In previous studies, for example in Sklar et al. (2000), Solubilization and Display of G Protein-Coupled Receptors on Beads for Real-Time Fluorescence and Flow Cytometric Analysis, Biotechniques, 28, pp 975–976, the entire contents and disclosure of which is hereby incorporated by reference, commercial porous silica particles intended for protein purification were used (Qiagen; Valencia, Calif.). Although they could bind several million receptors on an average size particle, the particles were heterogeneous in size, appeared to break under gentle stirring as monitored by flow cytometry light scatter patterns, and settled rapidly in aqueous media. Therefore, a hydrophilic particle, DCNi, was prepared as described in the experimental procedures discussed herein. Hexahistidine-tagged enhanced green fluorescent protein (H6-GFP; generously supplied by Dr. John Nolan), see Lauer S A and Nolan J P (2002), Development and Characterization of Ni-NTA-Bearing Microspheres, Cytometry, 48, pp 136–145, the entire contents and disclosure of which is hereby incorporated by reference, was used initially to help determine the suitability of the DCNi beads for display of proteins in a flow cytometer. This H6-GFP was found to have a molar fluorescence, or quantum yield, in solution of 60% compared with our standard fluoresceinated formyl peptide ligand, formyl-MLFK-FITC.

Figure 9A:
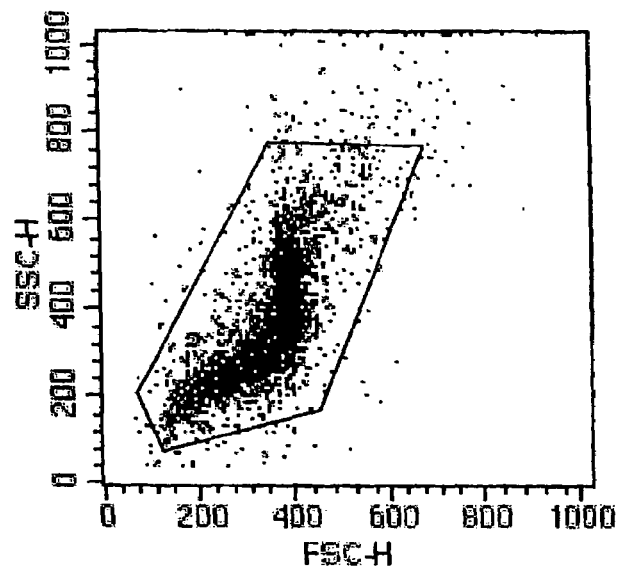
FIG. 9A is a dot plot of forward scatter vs. side scatter.
Figure 9B:
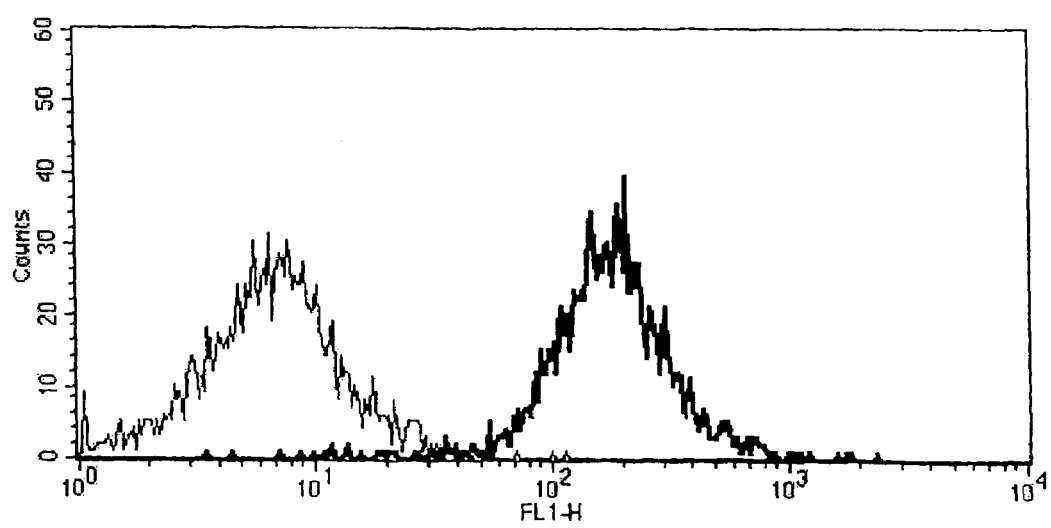
FIG. 9B is a histogram of DCNi with 0 or 10 nM hexahistidine-tagged green fluorescent protein (H6-GFP)
Figure 9C:
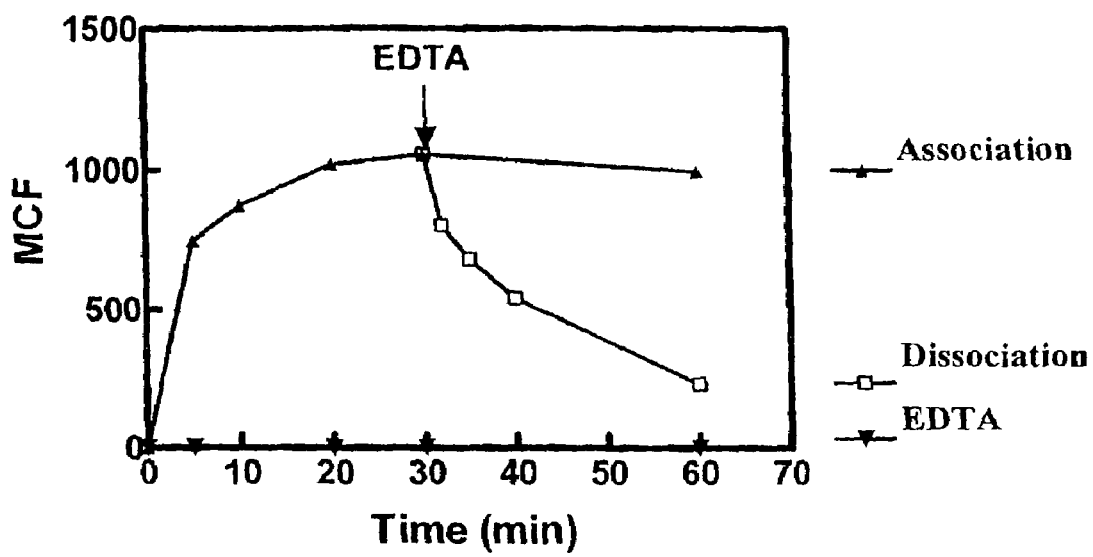
FIG. 9C is a time course of DCNi binding to 10 nM H6-GFP in the presence of 10 mM EDTA (inverted triangles), absence of EDTA (triangles), and with 10 mM EDTA added after 30 min (open squares)
Figure 9D:
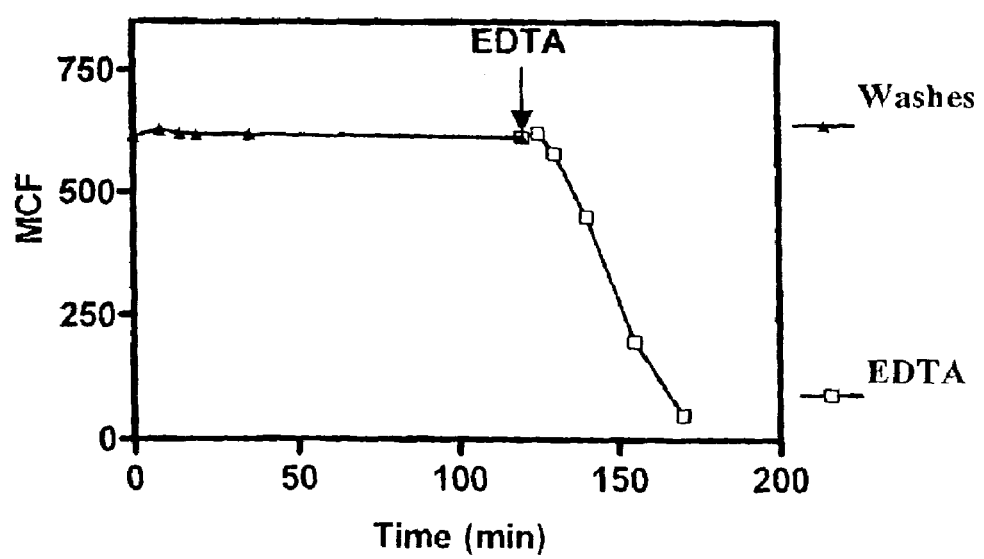
FIG. 9D shows DCNi binding to H6-GFP through five washes over two hours (triangles) and with 10 mM EDTA added after two hours (open squares), where beads were kept in suspension with moderate mixing at 0–4° C., and 200 μl aliquots were removed for flow cytometric measurement of bead fluorescence.

DCNi beads of the lowest level of substitution were suspended in phosphate-buffered saline at 50,000 beads/ml at 4° C., with or without 10 mM EDTA. FIG. 9A is a dot plot of these beads' forward scatter vs. side scatter, which vary slightly more than those of a cell population. FIG. 9B displays a histogram of unstained and stained beads. The kinetic data of FIG. 9C show that in the absence of EDTA, addition of 10 nM H6-GFP resulted in maximal bead fluorescence after about 20 minutes, and displayed about 5 million fluors per bead by comparison with standardized fluorescent microspheres. A portion of these beads was brought to 10 mM EDTA at 30 minutes, and the H6-GFP on the beads was reduced by 80% after 30 minutes. The stable binding of this platform is demonstrated in FIG. 9D, in which the H6-GFP remained on the beads for five washes over two hours, following which the H6-GFP was displaced by 10 mM EDTA as before. Nickel chelate beads have high nonspecific binding in general, and the presence of other protein or detergent (1 mg/ml BSA or 0.1% Tween-20, respectively) reduced the binding of H6-GFP by 80% (data not shown).

Figure 9E:
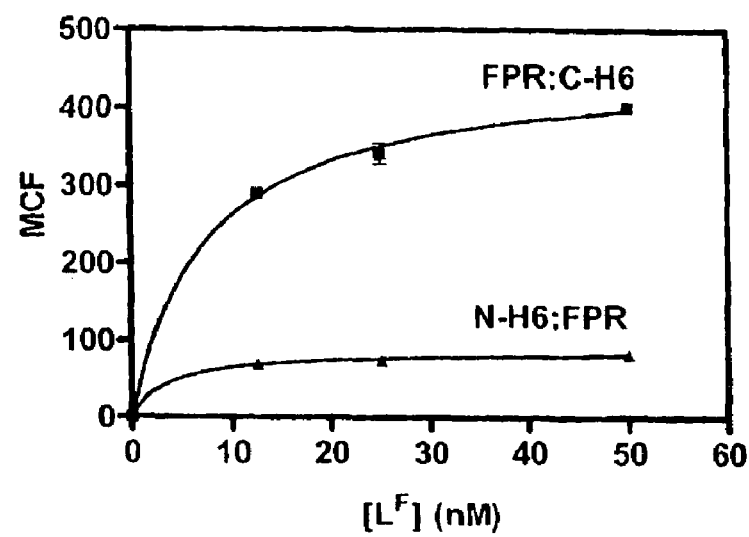
FIG. 9E represents membranes from cells expressing N-terminal hexahistidine-tagged FPR(N-H6:FPR) or C-terminal hexahistidine-tagged FPR (FPR:C-H6) which were solubilized as described in the experimental procedures discussed herein, with 18.5 nM FPR:C-H6 or 10 nM N-H6: FPR, and incubated with 50,000 DCNi beads in 200 μl of 0.1% dodecyl maltoside in buffer A with moderate mixing for seven hours in duplicate, where the beads were washed by centrifugation and resuspensed in fresh buffer, incubated with various concentrations of $L^F$ as shown in the graph for 30 min, and then the bead fluorescence was measured by flow cytometry.
Figure 9F:
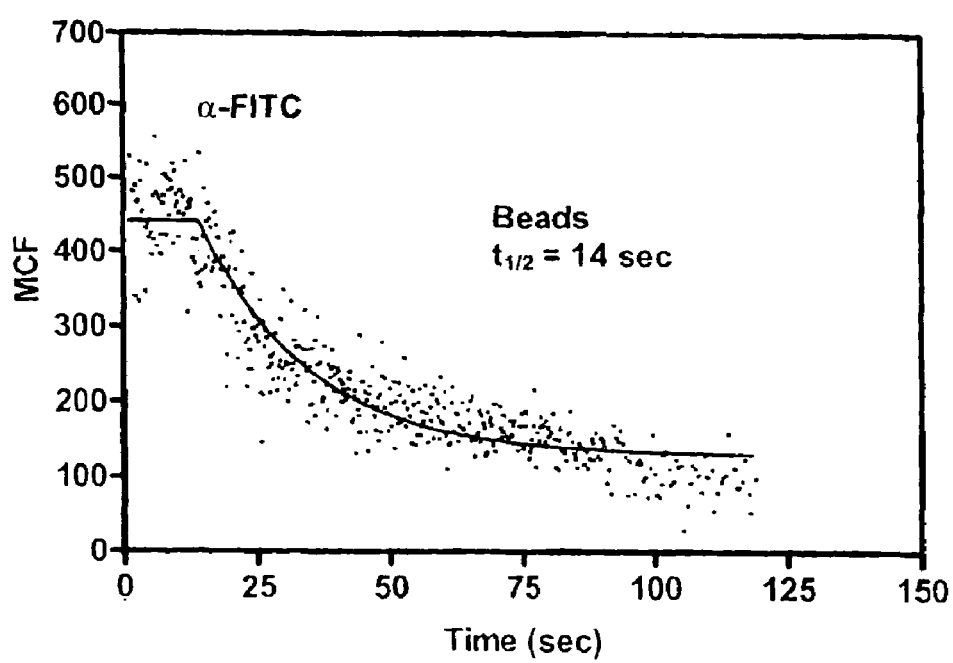
FIG. 9F shows the dissociation of $L^F$ from beads, which were coated with FPR:C-H6 in FIG. 9E, which was monitored using a custom built rapid mixer, as described in the experimental procedures discussed herein. The initial bead fluorescence was measured for twenty seconds, then an anti-FITC antibody was mixed with the beads, and the decrease in bead fluorescence was measured for another 100 seconds. The line shown is a best fit to a plateau, followed by an exponential decrease to the bottom.

As described previously in Sklar et al. (2000), Solubilization and Display of G Protein-Coupled Receptors on Beads for Real-Time Fluorescence and Flow Cytometric Analysis, Biotechniques, 28, pp 975–976, the entire contents and disclosures of which are hereby incorporated by reference, several million six histidine-tagged receptors could bind to a porous silica nickel chelate bead, in an LR form with a $K_d$ similar to the soluble receptor in detergent. DCNi beads were able to bind about 400,000 formyl peptide receptors with a C-terminal hexahistidine tag (FPR:C-H6), as detected by $L^F$ (FIG. 9E). The amount of receptor bound was a function of the position of the tag, with the FPR:C-H6 consistently binding more than the FPR with an N-terminal hexahistidine tag (N-H6:FPR). Although there was 1.9 times the concentration of FPR:C-H6 compared to N-H6:FPR in this experiment, the FPR:C-H6 displayed 5 times the binding of N-H6:FPR. The binding of receptor in this complex mixture of solublilized proteins was very slow, and continued to increase even after the seven hour data obtained in FIG. 9E (data not shown). The $K_d$ for ligand binding was estimated to be 8 nM and the ligand dissociation rate was similar on beads to the rate in detergent solution, with a 14 second halftime of dissociation (FIG. 9F). While the receptor appeared to behave normally, addition of heterotrimeric G did not alter the ligand $K_d$ or dissociation rate using the N-H6:FPR, which was expected to have a free binding site for G protein while bound to the beads. Therefore, the route to ternary complex assembly was followed as described below.

Figure 10:
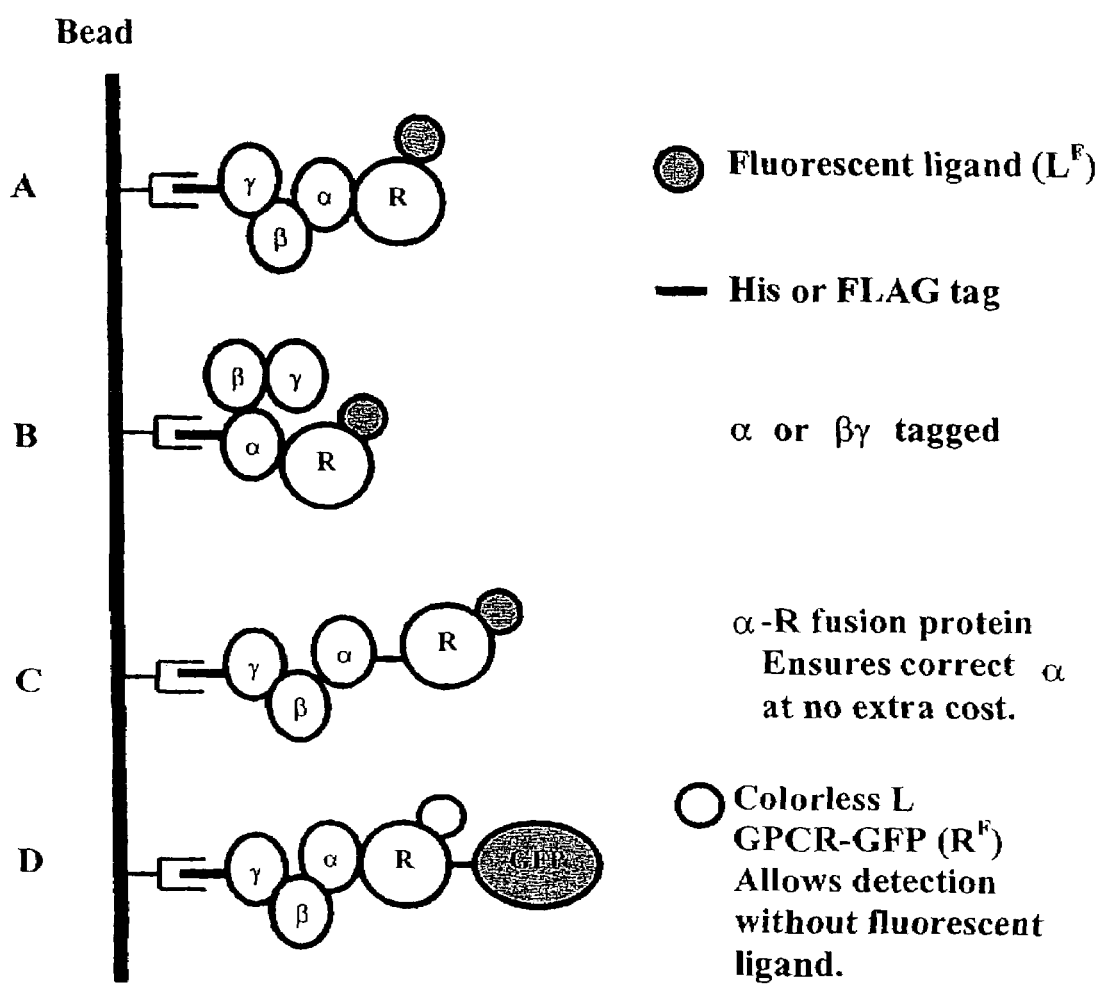
FIG. 10 shows ligand-receptor-G-protein complex (LRG) assembly schematics. Complex A shows fluorescent ligand, wild type receptor, epitope tagged Gβγ, and Gα bound to a derivatized bead; complex B is the similar to complex A, except with the epitope on the Gα subunit; complex C shows fluorescent ligand, receptor-Gα fusion protein, and epitope tagged Gβγ bound to the bead; complex D shows a colorless ligand, receptor-GFP fusion protein, epitope tagged Gβγ, and Gα bound to the bead. In each case, a receptor without ligand would not bind the bead significantly.

Detection of $L^F$RG Complexes on Beads. As structural analysis and functional studies suggested that the amino terminus of the γ subunit could be modified without interfering with ternary complex assembly, see McIntire et al. (2001), The G Protein Beta Subunit is a Determinant in the Coupling of Gs to the β 1-Adrenergic and A2a Adenosine Receptors, J Biol Chem, 276, pp 15801–15809, the entire contents and disclosure of which is hereby incorporated by reference, purified, epitope-tagged G-proteins were used to coat the particles. FIG. 10 shows several complementary attachment schemes: wild type receptors binding to bead-associated subunits with fluorescent ligand detection (complexes A and B); Giα2-receptor fusion protein detected with fluorescent ligand (complex C); and receptor-GFP fusion protein detected directly (complex D).

Figure 11A:
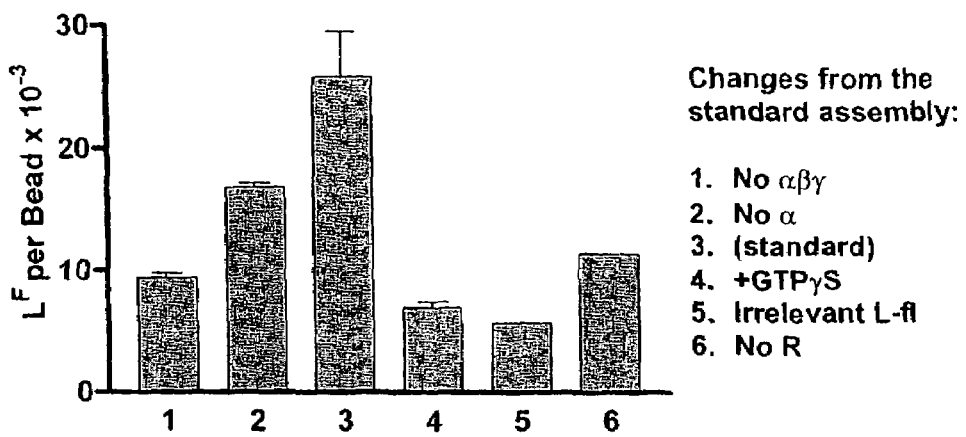
In FIG. 11A, a fluorescent ligand ($L^F$) was used with wild type formyl peptide receptor (R) to detect the assembly of $L^F RG$ on DCNi beads. Previous work with LRG complexes in solution had shown that ternary complex formation was complete in two hours at 4° C. in a 10 μl LRG assembly assay starting with concentrations of $L^F$=20 nM, and of R and G of about 100 nM. The 10 μl assay was then diluted to 200 μl for spectrofluorimetric measurement. For the bead assay, 24,000 of the G beads were incubated with 60 nM FPR and 75 nM $L^F$ in 10 μl assays in a 96 V-well plate on a vortex mixer for two hours, then the assays were diluted to 200 μl for flow cytometric measurement. Uncoated beads were used in an assembly assay, bar 1, or were coated with G protein βγ only and used in an assembly assay, bar 2. In bar 3, the standard assembly with Gαβγ was used; in bar 4, 0.1 mM GTPγS was added to the assembly assay; in bar 5, a fluoresceinated peptide, specific for the α4 integrin, see Chigaev et al. (2001), Real Time Analysis of the Affinity Regulation of α 4-Integrin: The Physiologically Activated Receptor is Intermediate in Affinity Between Resting and Mn(2+) or Antibody Activation, J Biol Chem, 276, pp 48670–48678, the entire contents and disclosure of which is hereby incorporated by reference, was used in place of fluoresceinated formyl peptide; and in bar 6, membranes from cells containing no receptor were used instead of receptor-containing membranes.

To prove the concept of assembly on beads, fluorescent ligand, $L^F$, was used to form $L^F$RG on the beads (FIG. 10, complex A). G protein coated beads (G beads) were prepared and washed as described in the experimental procedures discussed herein, giving beads coated with αi3β1H6γ2 (18 million αβγ were provided per bead, and based on the solubilized receptor, perhaps 400,000 were in proper orientation). Evidence that fluorescence on the beads was due to $L^F$RG included the requirement that $L^F$, R, and G were all necessary for fluorescence over nonspecific, background fluorescence. As shown in FIG. 11A, uncoated beads gave a background binding equivalent to about 9,000 fluorophores. The binding doubled when βγ was on the beads, and tripled when αβγ was on the beads. These data may be interpreted to indicate that the αβγ beads, having the highest fluorescence, had everything necessary for $L^F$RG formation, while the βγ beads, probably with endogenous αi supplied in the crude solubilized membrane FPR preparation, gave an intermediate, weaker signal. The addition of GTPγS, which should dissociate α from βγ and R, resulted in only background fluorescence (similar to unlabeled beads) both with βγ and αβγ beads, as expected. This observation rules out binding of $L^F$R to βγ alone and indicates that an α subunit, either exogenous or in the receptor preparation, may be required. Use of an irrelevant fluorescent peptide, specific for the α4 integrin, see Chigaev et al. (2001), Real Time Analysis of the Affinity Regulation of α 4-Integrin: The Physiologically Activated Receptor is Intermediate in Affinity Between Resting and Mn(2+) or Antibody Activation, J Biol Chem, 276, pp 48670–48678, the entire contents and disclosure of which is hereby incorporated by reference, instead of a fluorescent formyl peptide, also showed only nonspecific binding. Substitution of parental cell extracts that contained no receptor showed increased binding, attributed to the fact that free ligand was higher in the absence of FPR, which binds the majority of the total ligand; a high concentration of the free ligand alone gives a nonspecific signal of this magnitude (data not shown). Thus, $L^F$, R, and G were all necessary for the specific fluorescent signal, defined as bar 3 minus bar 4. Under more nearly optimal conditions, signal to background levels have been observed as high as 4/1 in this assembly with 30,000 ternary complexes per particle.

Figure 11B:
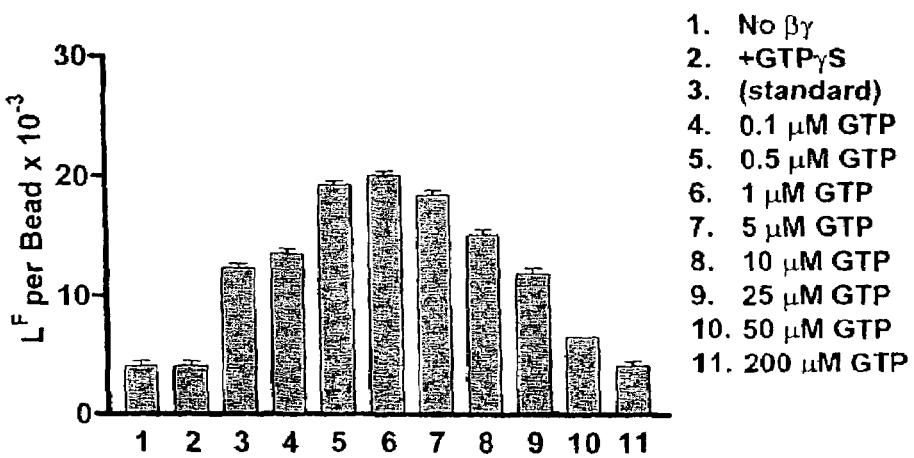
In FIG. 11B, fluorescent ligand ($L^F$, 40 nM) was used with an FPR-Gαi2 fusion protein (24 nM) to detect $L^F R$-αGβγ assembly on beads coated with Gβγ (1.4 pmol/assay). In bar 1, the beads were not coated with βγ; bar 2, with 0.1 mM GTPγS; bar 3, the standard assembly with Gβγ; bars 4–11, the indicated amounts of GTP were added to the standard assembly.
Figure 14:
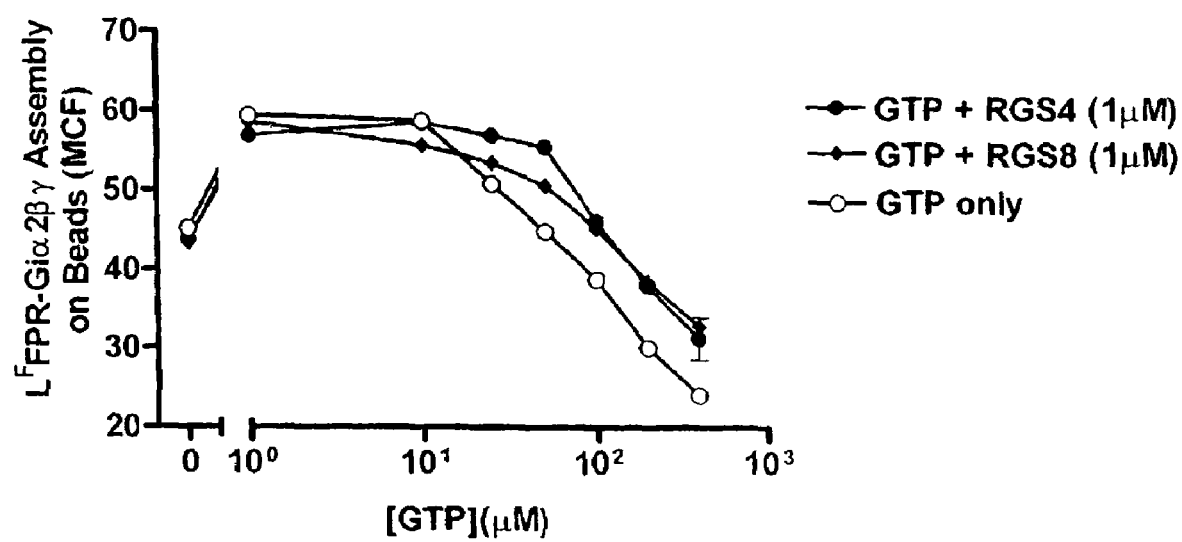
FIG. 14 shows the results of a regulator of G protein signaling (RGS) activity assay on beads. FPR-αi2 (R-α) was used in the standard assembly assay with fluorescent ligand (see FIG. 3, complex C), and with the amounts of GTP and RGS shown in FIG. 14, using beads coated with Gβγ. Bead fluorescence was measured as previously described.

Detection of $L^F$R-αGβγ Complexes on Beads. An FPR-αi2 fusion protein was generated as described in the experimental procedures discussed herein, and solubilized. With this construct (FIG. 10, complex C), it was anticipated that endogenous βγ in the solubilized fusion protein preparation might bind to FPR-αi2 to form LRG complex in solution (Shi et al., submitted), and prevent the FPR-αi2 from binding the βγ on the beads. Therefore, the ability of GTP to promote the dissociation of FPR-αi2 from endogenous βγ was examined, and as the GTP was hydrolyzed, the ability of more FPR-αi2 to bind the βγ beads was examined. βγ beads (24,000) were mixed with 24 nM FPR-αi2 and 40 nM $L^F$ as in the standard protocol, with GTP as indicated, in FIG. 11B. Uncoated beads, and beads coated with βγ but incubated in the presence of GTPγS, gave background binding equivalent to about 5,000 fluors. Assembly in the absence of GTP showed about 12,000 fluors, while assemblies in the presence of 0.1 μM to 10 μM GTP all showed up to 20,000 fluors. Assemblies conducted in the presence of yet higher amounts of GTP showed less bead fluorescence than assembly with no GTP, consistent with excess GTP remaining after the incubation. 1 μM GTP was optimal for the highest binding on the beads and the highest specific signal, defined as bar 6 minus bar 2. Additional experiments with RGS suggested that GTP consumption played a role in ternary complex assembly (see FIG. 14). The best total fluorescence to background ratio (bar 6 compared to bar 2) was 2.7/1, similar to that observed for the wild type receptor above.

Figure 11C:
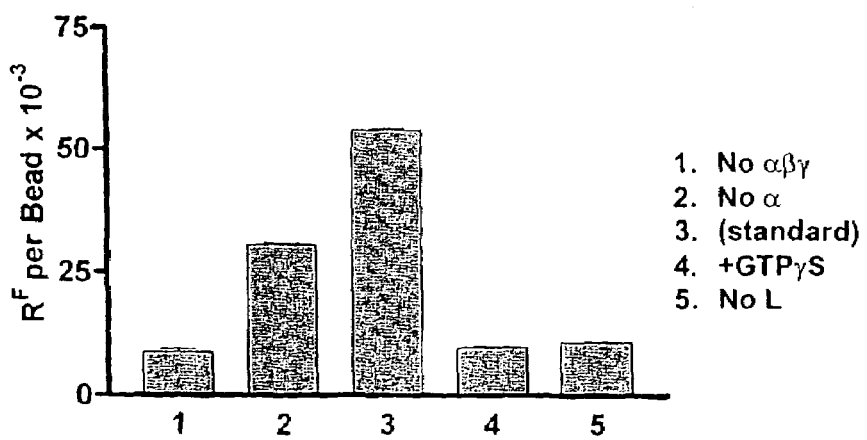
In FIG. 11C, a fluorescent formyl peptide receptor $R^F$ (FPR-GFP, 200 nM) was used to detect the assembly of $LR^F G$ on DCNi beads in the presence of 300 nM L. Beads alone are shown in bar 1, or coated with βγ only in bar 2; the standard assembly, bar 3; bar 4, GTPγS was included in the assembly assay; and bar 5, no ligand was used in the assembly assay.

Detection of $LR^F$G Complexes on Beads. The third assembly used a fusion protein of FPR with enhanced green fluorescent protein (FIG. 10, complex D: FPR-GFP, or $R^F$). The fusion protein was expressed and solubilized as described in the experimental procedures discussed herein. This receptor bound to the beads in a manner consistent with $LR^F$G formation. In FIG. 11C, background binding of this receptor, with saturating amounts of the non-fluorescent ligand fMLFFGGK, to uncoated beads gave a background binding equivalent to about 5,000 fluors, binding to βγ-coated beads to about 30,000 fluors, and binding to αβγ-coated beads to about 60,000. The assembly on the βγ beads was likely due to the endogenous $α_i$ subunit from the solubilized receptor preparation, since in the presence of GTPγS the signal was virtually the same as background. The control experiment with no receptor in the assembly reaction was not carried out, as the GFP (without receptor) had a hexahistidine tag on it. The control experiment without ligand gave nearly the same signal as the nonspecific binding. The best total binding to background ratio (bar 3 compared to bar 4) was 4.9/1, slightly better than above. Thus, three FPR variants were used to demonstrate the formation of an LRG complex on beads. At least tens of thousands of each of the ternary complexes could be formed on the beads.

Figure 12A:
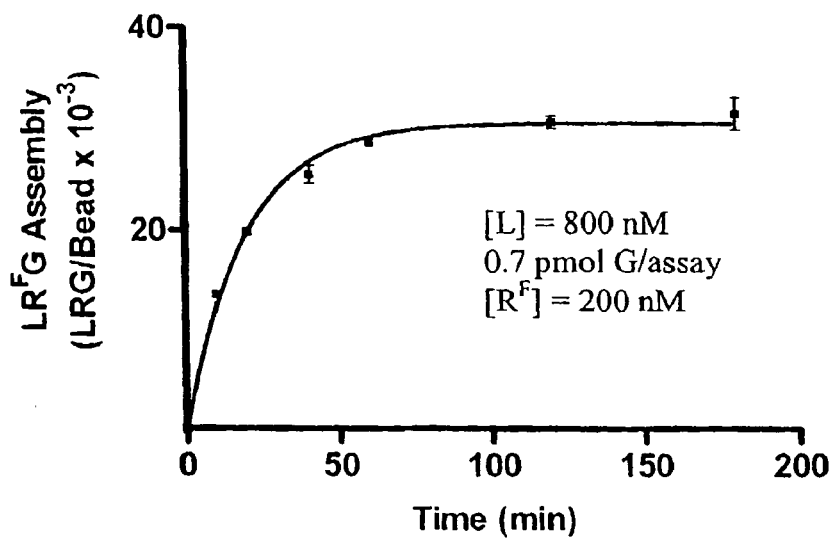
In FIG. 12A, the time of assembly $LR^F G$ was varied.

Kinetics and Concentration Dependences of the Standard LRG Assembly. The availability of three receptor forms provided a unique opportunity to evaluate the affinity of individual steps of the ternary complex model (L to R, LR to G, and α to βγ). To accomplish this task, the assembly time course for $LR^FG$ assembly was determined (schematic of FIG. 10, complex D), which revealed a halftime of 13 minutes and a calculated association of about 30,000 $LR^FG$ complexes/bead (FIG. 12A). Other experiments showing that maximum assembly was achieved in one to three hours led to the selection of two hours as the standard time of assembly, which is therefore near equilibrium.

Figure 12B:
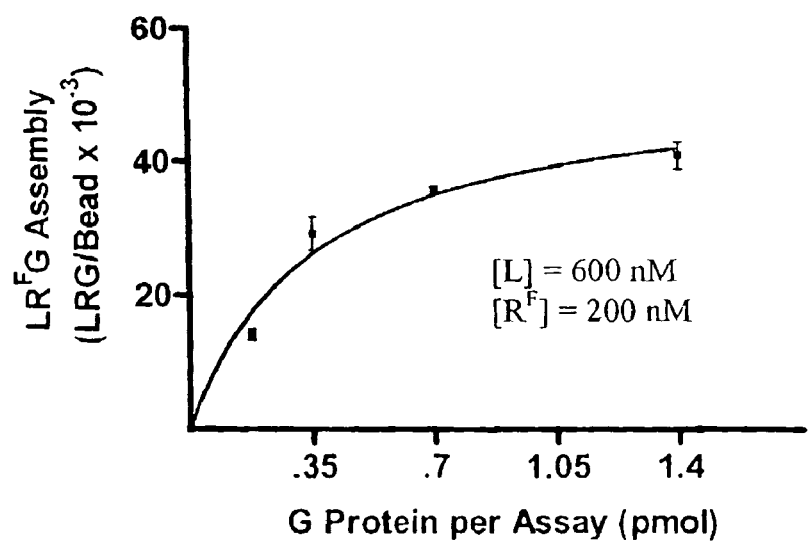
In FIG. 12B, the amount of Gαβγ used to coat the beads was varied for $LR^F G$ assembly.

In FIG. 12B, the amount of G protein incubated with the beads in the standard coating procedure was varied; the line shown is a fit to a simple binding curve, giving half saturation of the beads at 0.35 pmol G applied per assembly assay, corresponding to about 9 million αβγ provided per bead, and a $B_{max}$ of 50,000 $LR^FG$ per bead. This curve reflects bead saturation, rather than an $EC_{50}$ for LRG assembly, which is described in FIG. 12B. The standard protocol thus resulted in 67% saturation of beads with respect to G protein.

Figure 12C:
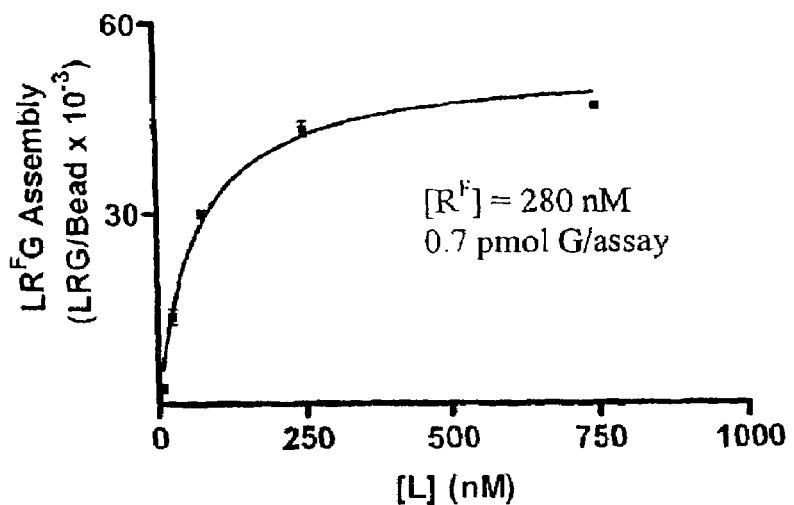
In FIG. 12C, the concentration of ligand used was varied for $LR^F G$ assembly.

In FIG. 12C, the concentration of L was varied, and the results again followed a simple binding curve, with half-maximal $LR^FG$ assembly at 115 nM L or half of the $R^F$ concentration. Since depletion of RF was required for the assay, the affinity of L for $R^F$ was not revealed. The standard assembly, with ligand concentration at least 20% higher than the receptor concentration, gave near saturation with respect to LRG assembly.

Figure 12D:
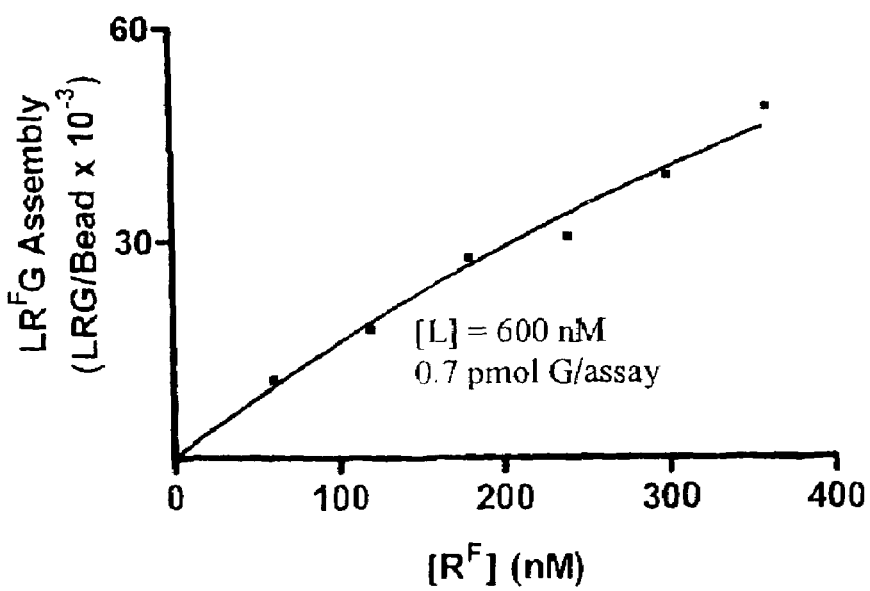
In FIG. 12D, the concentration of FPR-GFP used was varied for $LR^F G$ assembly.
Figure 12E:
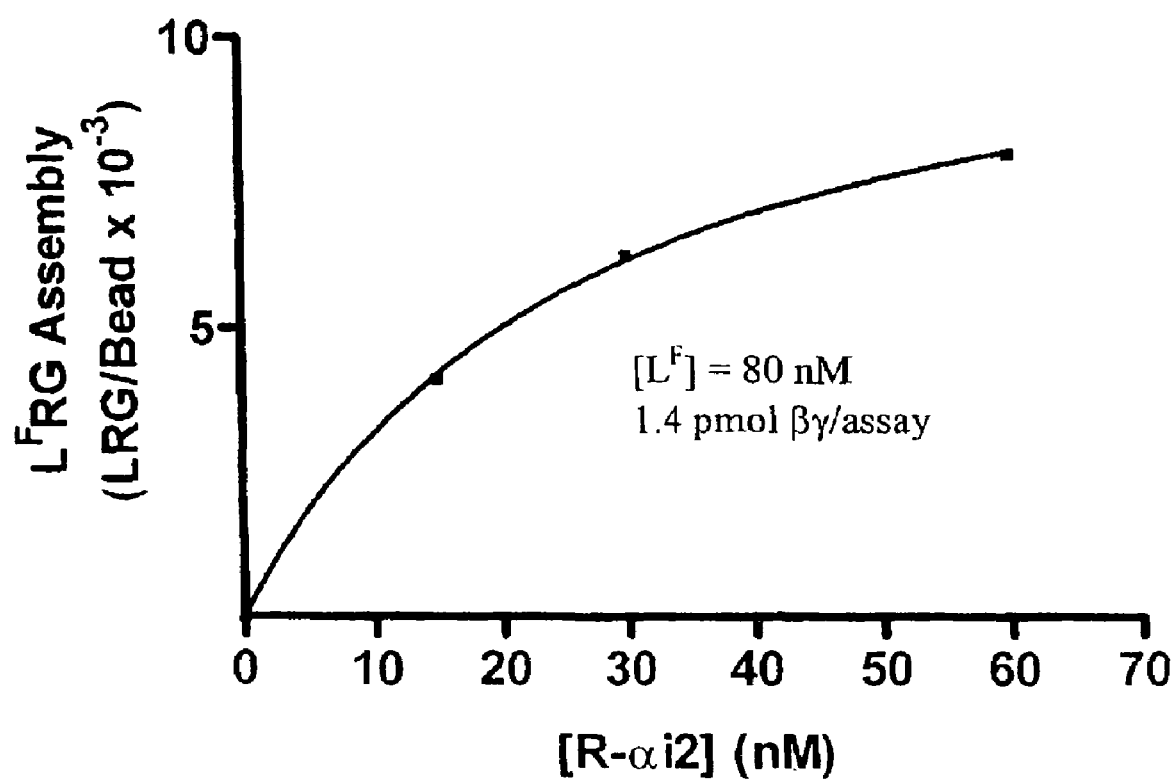
In FIG. 12E, the concentration of FPR-αi2 used in the standard assembly (scheme of FIG. 10, complex C) was varied, using beads coated with Gβγ, for $L^F R$-αGβγ assembly.

In FIG. 12D, the concentration of $R^F$ was varied with saturating L. The binding was nearly linear over the accessible concentration range of receptor. The fit to the data is for a $K_d$ of 1 μM, consistent with that obtained by solution measurement for LR to G, see Bennett et al. (2001), Real-Time Analysis of G Protein-Coupled Receptor Reconstitution in a Soubilized System, J Biol Chem, 276, pp 22453–22460, the entire contents and disclosure of which is hereby incorporated by reference. The calculated $B_{max}$ was unreliable because the data were obtained at such a low concentration of receptor compared to the dissociation constant. The standard assembly at 200 nM R was thus saturating for time and ligand, 67% saturating for G protein, and gave about 30,000 $LR^FG$ ternary complexes per bead.

Figure 5:
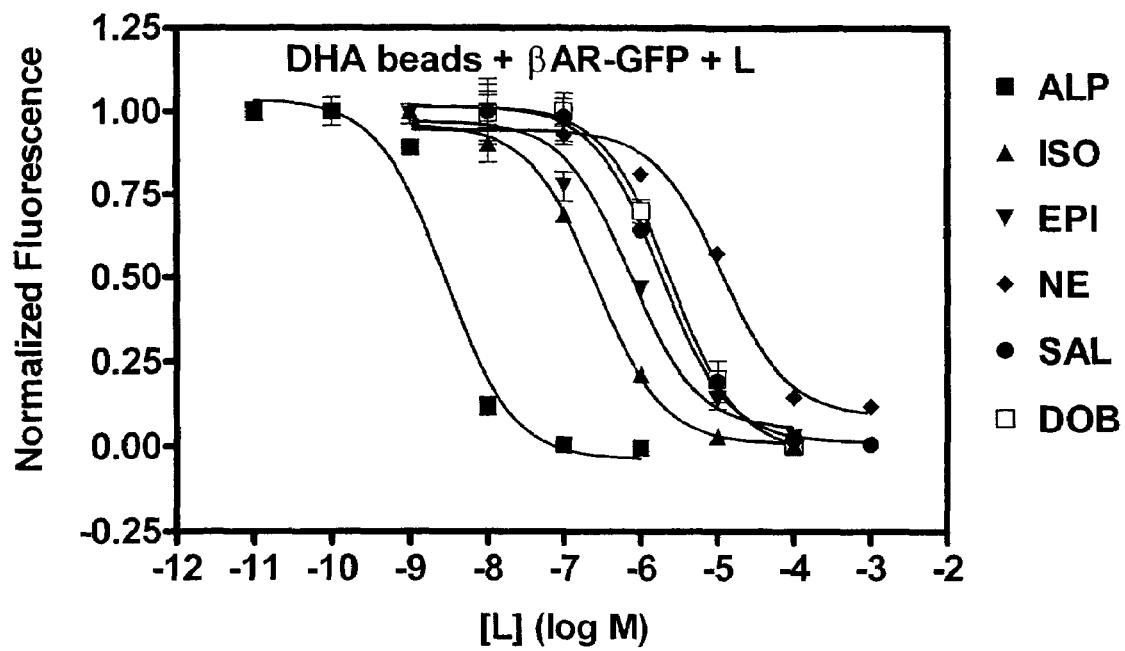
FIG. 5 illustrates the determination of $K_d$ values for LR formation, and $EC_{50}$ values for ARG assembly (potency), for selected ligands.
Figure 5:
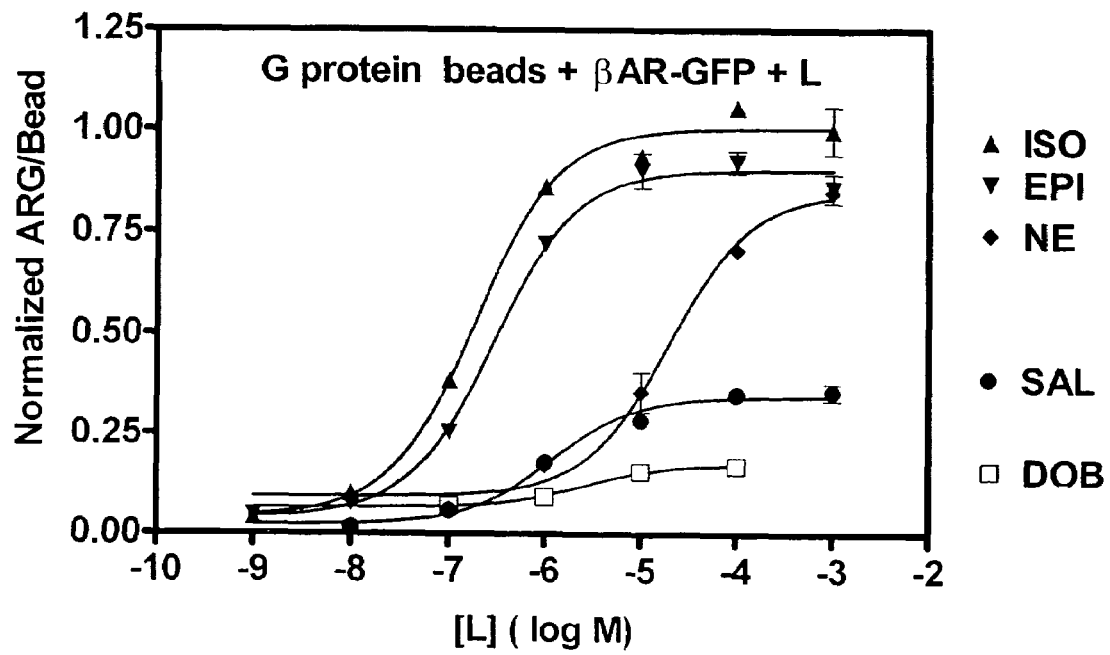

An analogous experiment was performed for the $L^F$R-αGβγ assembly (schematic of FIG. 10, complex C). This examined the affinity of the α to βγ interaction using βγ on the beads, the FPR-Gαi2 fusion protein, and excess fluorescent ligand (FIG. 5E). The apparent $K_d$ of the R-α to βγ assembly was 26 nM, similar to but higher than that observed previously in detergent solutions with fluorescent subunits alone on beads, 3–9 nM, see Sarvazyan et al. (1998), Determinants of Giα and βγ Binding: Measuring High Affinity Interactions in a Lipid Environment Using Flow Cytometry, J Biol Chem, 273, pp 7934–7940, the entire contents and disclosure of which is hereby incorporated by reference. The lower amount of assembly compared to FIG. 11B, bar 6, is a reflection of assembly in the absence of GTP.

Figure 13A:
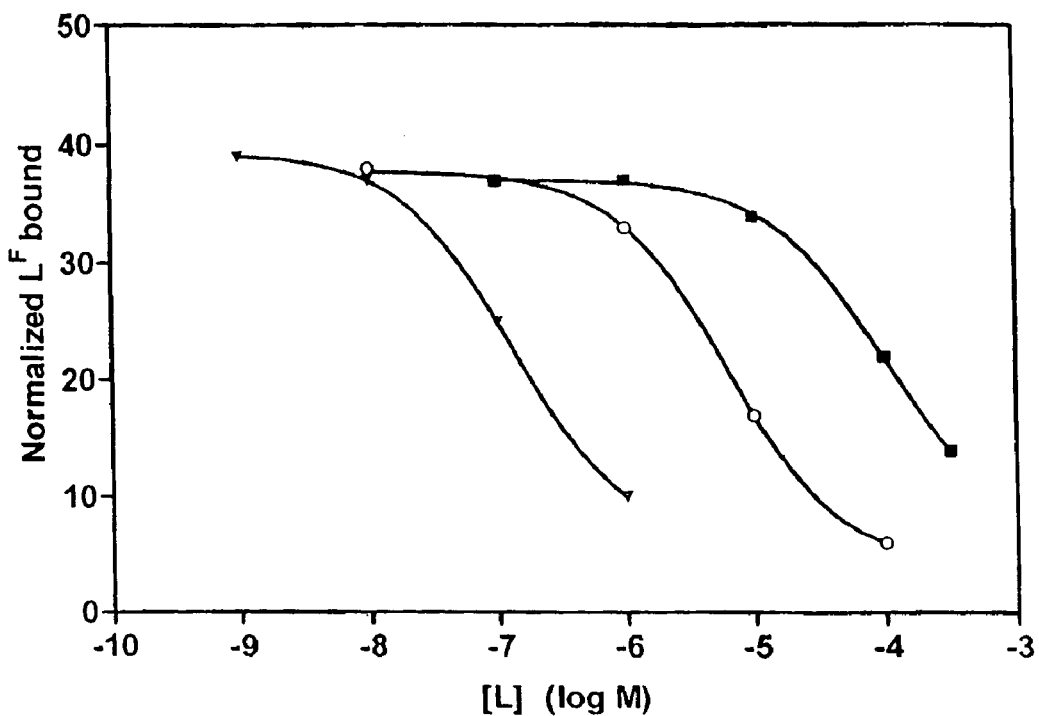
FIG. 13A shows the determination of the dissociation constants of nonfluorescent ligands for receptor (R) by competition with $L^F$ in the spectrofluorimeter. Receptor (3 nM) and $L^F$ (5 nM) were incubated at 22° C. for two minutes, then an anti-FITC antibody was added as in FIG. 1A and analyzed to give an initial amount of $L^F$ bound, shown as the dotted line in FIG. 13A. Increasing amounts of nonfluorescent ligand were added to the R for two minutes, then $L^F$ was added for another two minutes to compete for the R, after which an anti-FITC antibody was added to determine the $L^F$ bound. $IC_{50}$ values were calculated from these curves, then $K_i$ values were calculated for each ligand, using the known $[L^F]$, $[R]$, and the $K_d$ of $L^F$ for R, from three experiments.
Figure 13B:
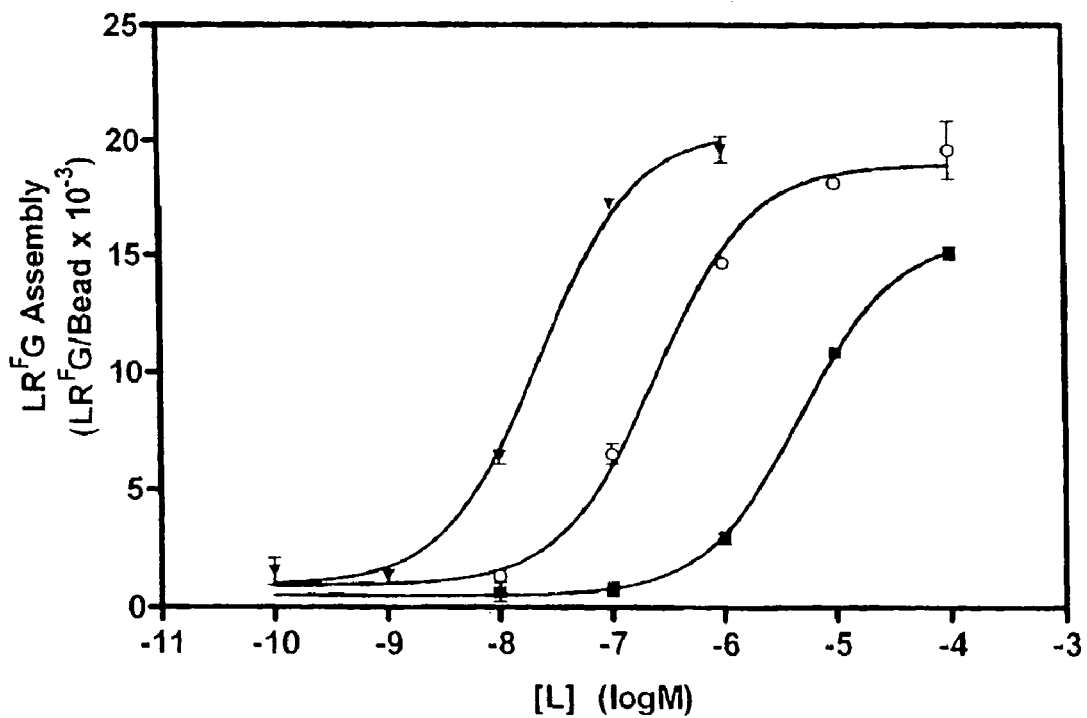
FIG. 13B shows the determination of the $EC_{50}$ for nonfluorescent ligands for LRG formation. The standard LRG assembly assay was conducted with 30 nM $R^F$ and increasing amounts of each ligand as shown. $EC_{50}$ values were obtained from analysis of the curves, using three experiments for each.

Comparison of LR and LRG Affinities for a Family of Non-fluorescent Ligands. The complexes on particles offered the ability to examine mechanistic features of ternary complex assembly. First, the $K_d$s of a series of unlabelled ligands for the FPR were determined by spectrofluorimetry (FIG. 13A) and compared to LRG assembly (FIG. 13B). Competitive binding experiments were conducted in which increasing amounts of $L^F$ were allowed to compete with a fixed amount of fluorescent ligand and soluble receptor. $IC_{50}$ values were converted to $K_d$ values, using the known concentrations of $L^F$, R, and the $K_d$ of $L^F$ for R. The $K_d$ for fMLFF was $7.5+/-0.8\times10^{-8}$ M; for fMLF was $2.3+/-1.6\times10^{-6}$ M; and for fML was $1.5+/-0.9\times10^{-5}$ M.

The $EC_{50}$ values of the ligands for LRG formation were determined using the standard LRG assembly, as shown in FIG. 13B. Assemblies were conducted in which increasing amounts of each non-fluorescent ligand were added to the standard assembly with 30 nM $R^F$. The $EC_{50}$ value for fMLFF was $2.7+/-0.4\times10^{-8}$ M; for fMLF was $5.5+/-3\times10^{-7}$ M; and for fML was $5.3+/-0.4\times10^6$ M. The ratios of $K_d$ (for LR) to $EC_{50}$ (for LRG formation) for fMLFF was 2.8; for fMLF was 4.2; and for fML was 2.8. These data suggest that LRG assembly is a function of occupancy. The calculated maximal assembly of fML was 78+/-3% of the LRG assembly of the longer peptides. Although obtained near the limit of solubility of fML, the data suggest the possibility of partial agonism at the LRG assembly step in signal transduction, consistent with partial agonism for the dipeptide fMF for oxidant production in cells, see Sklar et al. (1985), Competitive Binding Kinetics in Ligand-Receptor-Competitor Systems: Rate Parameters for Unlabeled Ligands for the Formyl Peptide Receptor, Mol Pharmacol, 28, pp 323–330, the entire contents and disclosure of which is hereby incorporated by reference.

RGS Activity Affects LR-αG Assemblies on Beads. As a second mechanistic problem, the role of GTP and RGS activity in regulating the assembly of βγ subunits with the receptor-Giα fusion protein was examined (FIG. 14; see also FIG. 10, complex C and FIG. 11B). Because the assembly depended upon the high affinity α to βγ interaction (about $10^{-8}$ M), rather than the lower affinity interaction between R and G in detergent (about $10^6$ M), complexes were formed at near stoichiometric ratios of the components. The data were consistent with the idea that RGS, by enhancing the cleavage of GTP, affected the GTP dose-response for the formation of the bead-based complex. The shift in the dose-response was consistent with the consumption of 10 μM or more GTP in 10 μl over 2 hours in the presence of R-α, RGS, and L. Calculating that 24 nM R-α (the total added) consumed 10 μM GTP equally in the first half hour, leaving 60 minutes for assembly on the bead, the turnover number was about 14 min.$^{-1}$ for the receptor-Giα fusion protein at 7° C.; if rates double for every 10° C. increase, this would imply about 110 min$^{-1}$ at 37° C. Calculating consumption over the entire time yields about 5 and 40 min$^{-1}$, respectively.

Real Time Dissociation Kinetics by Flow Cytometry. To assess a third mechanistic potential, ternary complex disassembly with wild type receptor and $L^F$ was examined. LRG complexes generally display a higher affinity for L than do LR complexes alone, see Gilman A G (1987), G Proteins: Transducers of Receptor-Generated Signals, Annu Rev Biochem, 56, pp 615–649, the entire contents and disclosure of which is hereby incorporated by reference, and a slower dissociation rate of ligand from LRG complexes than from LR complexes of FPR in detergent was observed, see Bennett et al. (2001), Real-Time Analysis of G Protein- Coupled Receptor Reconstitution in a Soubilized System, J Biol Chem, 276, pp 22453–22460; Bennett et al. (2001), Partial Phosphorylation of the N-Formyl Peptide Receptor Inhibits G Protein Association Independent of Arrestin Binding, J Biol Chem, 276, pp 49195–49203; and Key et al. (2001), Regulation of Formyl Peptide Receptor Agonist Affinity by Reconstitution with Arrestins and Heterotrimeric G Proteins, J Biol Chem, 276, pp 49204–49212, the entire contents and disclosures of which are hereby incorporated by reference. Ternary complex disassembly was anticipated after GTPγS addition with a halftime <<14 seconds, the halftime associated with LR dissociation in solution (FIG. 8A) and on beads (FIG. 9F).

Figure 15A:
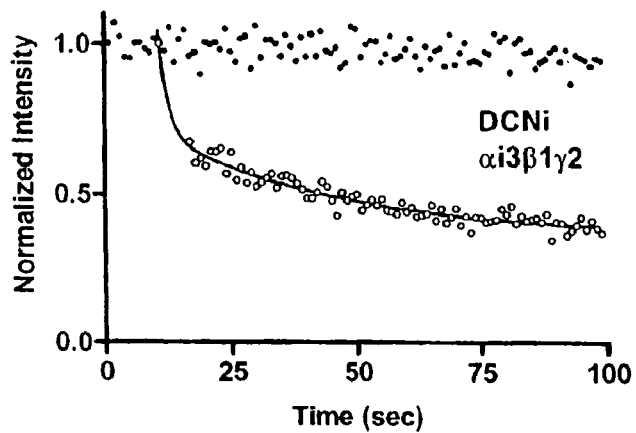
In FIG. 15A, wild type FPR was used in the standard assembly to form $L^F RG$, and then the samples were diluted to 200 μl for kinetic flow cytometric measurement of bead fluorescence. Samples were applied to the cytometer for determination of initial bead fluorescence, then removed for addition of the GTPγS, after which the samples were returned to the cytometer for measurement of bead fluorescence (note five second gap). The filled circles represent no GTPγS addition. The initial open circles have been averaged over 10 sec, normalized to 1.0 and are shown as a single point for clarity at the point of GTPγS addition with the best fit to a two exponential decay shown as a line.
Figure 15B:
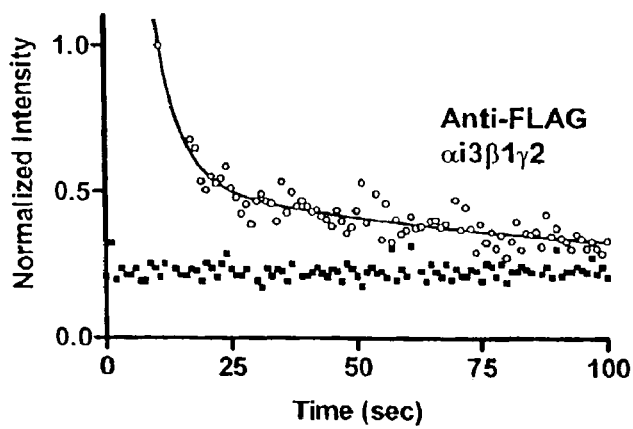
In FIGS. 15B and 15C, six micron streptavidin-coated polystyrene beads were coated with biotinylated anti-FLAG antibodies as described in the experimental procedures discussed herein. The beads were then incubated with Gαi3β1γ2H6-FLAG (FIG. 15B) or Gαi3β4γ2H6—FLAG (FIG. 15C) in which the γ2 subunit was tagged with H6 and FLAG epitopes, as described in the experimental procedures discussed herein. Standard $L^F RG$ assembly assays were conducted with (filled squares) or without (open circles) 0.1 mM GTPγS as indicated on the graphs, after which the 10 μl assays were diluted to 200 μl, and the bead fluorescence was measured by flow cytometry, as above. FIG. B required two exponential decays to obtain a good fit, whereas FIG. C shows a line fit to a single exponential decay.
Figure 15C:
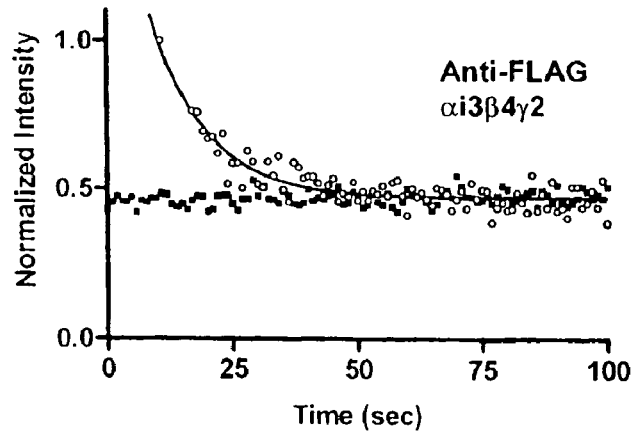

The dissociation of LRG complexes was followed by flow cytometry using manual addition of GTPγS to the bead suspensions (FIG. 15). FIG. 15A shows results using $L^FRG$ on DCNi beads. The halftime for loss of fluorescence ($L^F$) from the particles in the absence of nucleotide was much greater than 100 seconds, corresponding to $L^FRG$. At saturating GTPγS a fast component was observed, with a halftime of <5 seconds, or faster than LR dissociation. To evaluate the possibility that non-specific interactions were contributing to the stability on the DCNi beads, complexes using streptavidin beads were assembled, coated with a biotin labeled anti-FLAG antibody, then coated with αi3+ βγ-FLAG complexes as described in the experimental procedures discussed herein. Studies were performed with two different βsubunits, β1 and β4, which have both been shown to complex efficiently with receptors in αi1 complexes, see Lim et al. (2001), Receptor-G Protein Gamma Specificity: γ 11 Shows Unique Potency for A(1) Adenosine and 5-HT (1A) Receptors, Biochemistry, 40, pp 10532–10541, the entire contents and disclosure of which is hereby incorporated by reference. In assemblies here with αi3 and $L^F$, guanine nucleotide was able to induce dissociation when using β1γ2, in which a fast component was observed, again with a halftime of <5 seconds, and a second, slower component with a halftime of 10–40 seconds (FIG. 15B). Using β4γ2, a single exponential decay was observed, with a halftime of <10 seconds (FIG. 15C). As in earlier studies using different α subunits, see Bennett et al. (2001), Real-Time Analysis of G Protein-Coupled Receptor Reconstitution in a Solubilized System, J Biol Chem, 276, pp 22453–22460, the entire contents and disclosure of which is hereby incorporated by reference, the reconstitution of the formyl peptide receptor into a ternary complex was more efficient with αi3 than αi2 (not shown).

The present invention demonstrates the formation of LRG complexes on beads with three FPR variants. It extends work in which reconstitution of soluble receptors with signal transduction partners has been a valuable adjunct to cell physiology and confocal microscopy, see Bennett et al. (2001), Partial Phosphorylation of the N-Formyl Peptide Receptor Inhibits G Protein Association Independent of Arrestin Binding, J Biol Chem, 276, pp 49195–49203, the entire contents and disclosure of which is hereby incorporated by reference. Achieving ternary complex formation in detergent on particles involved evaluating several types of beads, attachment schemes with several epitope tags, and several approaches to tether ternary complexes, some of which did not prove useful. These included using hexahistidine-tagged receptors on DCNi beads (FIG. 9E) and biotinylated ligand on streptavidin beads (not shown). With hexahistidine-tagged receptors, the problem was nonspecific binding of G proteins to the particles. The biotinylated ligands that recognized soluble receptors in suspension did not capture those receptors on beads.

Assembly and Detection of Ternary Complexes on Beads. The wild type receptor (R) used in the $L^FRG$ assembly provides a direct comparison to the assembly of $L^FRG$ in solution, see Bennett et al. (2001), Real-Time Analysis of G Protein-Coupled Receptor Reconstitution in a Soubilized System, J Biol Chem, 276, pp 22453–22460; Bennett et al. (2001), Partial Phosphorylation of the N-Formyl Peptide Receptor Inhibits G Protein Association Independent of Arrestin Binding, J Biol Chem, 276, pp 49195–49203; and Key et al. (2001), Regulation of Formyl Peptide Receptor Agonist Affinity by Reconstitution with Arrestins and Heterotrimeric G Proteins, J Biol Chem, 276, pp 49204–49212, the entire contents and disclosures of which are hereby incorporated by reference. The conditions (60 nM R, 75 nM $L^F$, $K_d=5$ nM) ensured nearly quantitative conversion of R to $L^FR$, with 15 nM $L^F$ free to interact with the beads nonspecifically. The unavailability of fluorescent ligands for other GPCRs is a barrier to transferring this technology. While the receptor-Gαi2 (R-αi2) construct allows high affinity complex assembly with the α subunit available at no additional cost, it still uses a fluorescent ligand for detection and is not applicable to other receptors. The receptor-GFP fusion protein ($R^F$) allows quantification of the receptor, and obviates the development of a fluoresceinated ligand for every GPCR. It is a valuable construct for high throughput drug discovery applications. A triple fusion protein incorporating receptor, Gα subunit, and GFP, see Bevan et al. (1999), Functional Analysis of a Human A(1) Adenosine Receptor/Green Fluorescent Protein/G(11) α Fusion Protein Following Stable Expression in CHO Cells, FEBS Lett, 462, pp 61–65, the entire contents and disclosure of which is hereby incorporated by reference, would allow high affinity assemblies to be generalized to other receptors.

Affinities of the Components of the Complexes. Previous work with the solubilized FPR, see Bennett et al. (2001), Real-Time Analysis of G Protein-Coupled Receptor Reconstitution in a Soubilized System, J Biol Chem, 276, pp 22453–22460; Bennett et al. (2001), Partial Phosphorylation of the N-Formyl Peptide Receptor Inhibits G Protein Association Independent of Arrestin Binding, J Biol Chem, 276, pp 49195–49203; Key et al. (2001), Regulation of Formyl Peptide Receptor Agonist Affinity by Reconstitution with Arrestins and Heterotrimeric G Proteins, J Biol Chem, 276, pp 49204–49212; and Sklar et al. (2000), Solubilization and Display of G Protein-Coupled Receptors on Beads for Real-Time Fluorescence and Flow Cytometric Analysis, Biotechniques, 28, pp 975–976, the entire contents and disclosures of which are hereby incorporated by reference, enabled an analysis of the affinities of LR and LRG. The assembly of LRG in detergent solution took place in a 10 μl volume, with high concentrations of all components, as did assembly onto G protein coated beads. The two-hour time for assembly in solution was similar to assembly on the bead. Because of the high receptor concentration, ligand depletion at concentrations of ligand similar to that of receptor prevented direct analysis of L affinity with the $LR^FG$ complex. Because the receptor concentration was <500 nM, it was difficult to unequivocally determine the affinity of $LR^F$ for G, but the data were consistent with $K_d$ about 1 μM, similar to the solution value, see Bennett et al. (2001), Real-Time Analysis of G Protein-Coupled Receptor Reconstitution in a Soubilized System, J Biol Chem, 276, pp 22453–22460; Bennett et al. (2001), Partial Phosphorylation of the N-Formyl Peptide Receptor Inhibits G Protein Association Independent of Arrestin Binding, J Biol Chem, 276, pp 49195–49203; and Key et al. (2001), Regulation of Formyl Peptide Receptor Agonist Affinity by Reconstitution with Arrestins and Heterotrimeric G Proteins, J Biol Chem, 276, pp 49204–49212, the entire contents and disclosures of which are hereby incorporated by reference. The α to βγ affinity in the presence of LR, 26 nM, was based on the binding of R-αi2 to βγ. This is similar to the affinity observed in detergent with fluorescent subunits alone on beads, 3–9 nM, see Sarvazyan et al. (1998), Determinants of Giα and β γ Binding: Measuring High Affinity Interactions in a Lipid Environment Using Flow Cytometry, J Biol Chem, 273, pp 7934–7940, the entire contents and disclosure of which is hereby incorporated by reference.

Figure 6:
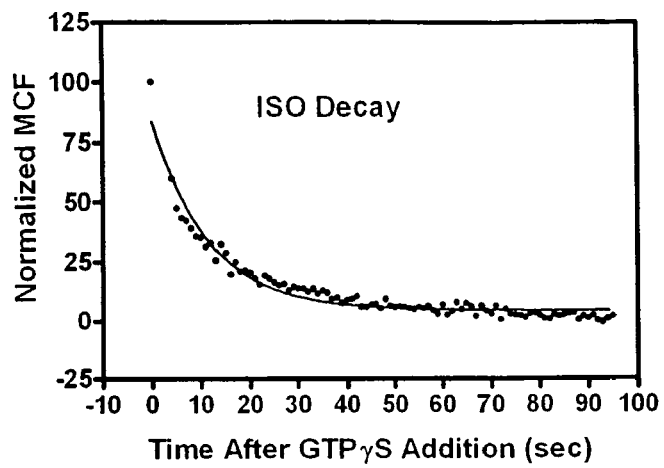
FIG. 6 illustrates that full and partial agonist ARG complexes are activated by GTPγS at the same rate. ARG assemblies were made as described in "Experimental Procedures", then diluted and applied to a flow cytometer for measurement of bead fluorescence. At 20 seconds, each tube was removed from the cytometer, 0.1 mM GTPγS was added and mixed, and the tube was returned to the cytometer again. The first dot in each panel is the average of the first 20 seconds' data, and is positioned in the figure where the GTPγS was mixed with the sample. The lines are fits to a single exponential decay.
Figure 6:
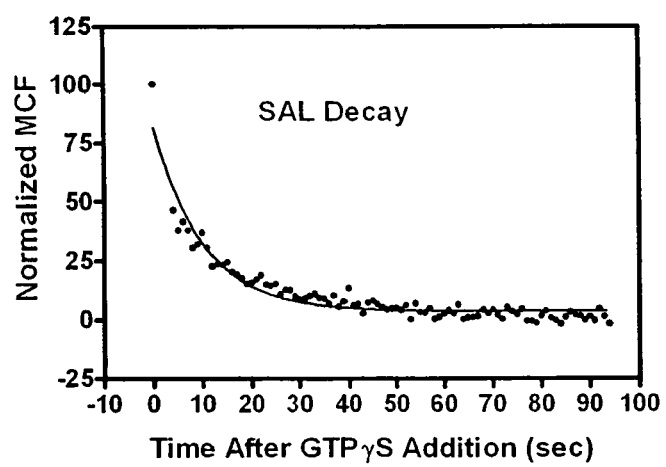
Figure 6:
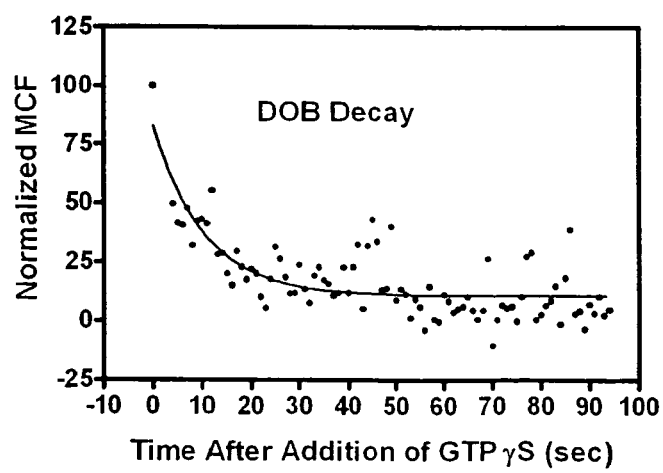

Applications. The three forms of receptor discussed in the present application allowed assemblies to be probed in novel ways. FPR-GFP was used to study ternary complexes for a family of ligands, the FPR-αi2 for RGS activity, and the wild type receptor for ternary complex disassembly kinetics. For a set of agonists, the affinities of LR and LRG varied essentially in parallel over three orders of magnitude with a hint that a partial agonist might be reflected in suboptimal assembly (FIG. 6). Similar results have been observed for the β2-adrenergic receptor (data not shown) with the efficacy of partial agonists reflected in suboptimal LRG assembly. Antagonists, and full and partial agonists have been simultaneously discriminated among in a format compatible with high throughput (see Marcus Evans Conference 'High Throughput Screening for Drug Discovery', Boston, Mass.; www.melifesciences.com; Simons P C, et al.).

The nucleotide sensitivity of the assembly of R-αi2 with βγ allowed the activity and specificity of RGS to be examined. While RGS4, RGS7 (not shown) and RGS8 appeared to consume GTP in the presence of LR-α, RGS2 did not, as expected, see Lan et al. (2000), Rapid Kinetics of Regulator of G-Protein Signaling (RGS)-Mediated Gαi and Gαo Deactivation: Gα Specificity of RGS4 and RGS7, J Biol Chem, 275, pp 33497–33503, the entire contents and disclosure of which is hereby incorporated by reference. This assembly format therefore has the potential for discriminating RGS antagonists. Elsewhere it is described how GTP increases access of soluble assemblies of R-αi2 to anti-αi2 antibody, consistent with the idea of βγ binding and release (Shi M, et al., submitted).

The assembly and disassembly kinetics of complexes on particles may provide insight into the ternary complex activation. FIGS. 8A and 9F show dissociation of $L^F R$ and $L^F C$-H6:FPR on DCNi beads (halftime about 14 sec in solution and on beads). The dissociation of $L^F R\alpha\beta\gamma$ on beads was far slower, but enhanced by the binding of GTPγS to a halftime faster than that observed for LR (FIG. 9F and FIG. 15). The combination of sensitivity of LRG and insensitivity of LR to nucleotide, the $K_d$s, and the kinetics, indicates that both binary and ternary complexes on beads as well as in solution may be observed.

The wild type ternary complex ($L^F R\alpha\beta\gamma$) dissociation was characterized in FIG. 8 and FIG. 15. During cell activation, the dissociation of R from α, or of α from βγ, could occur on a time frame much faster than LR dissociation. Either of these mechanisms would account for loss of fluorescence from the bead at a rate greater than dissociation of $L^F$ from R. Because non-specific interactions between proteins and DCNi beads could stabilize assembly and slow disassembly, the measurements were repeated with streptavidin beads, biotinylated anti-FLAG antibody, and FLAG-tagged βγ dimer. In all cases (two types of beads, two β, subunits), there was a fast component of dissociation that appeared, as expected, to be faster than dissociation of $L^F$ from R. These results are consistent with activation faster than ligand release, and indicate the potential of bead assemblies for mechanistic analysis. We previously showed that nucleotide binding induced a shift in affinity consistent with a millisecond conversion from LRG to LR in membranes, Neubig R R and Sklar L A (1993), Subsecond Modulation of Formyl Peptide-Linked Guanine Nucleotide-Binding Proteins by Guanosine 5'-O-(3-Thio)Triphosphate in Permeabilized Neutrophils, Mol Pharmacol, 43, pp 734–740, the entire contents and disclosure of which is hereby incorporated by reference, and observed a fast conversion in detergent, see Bennett et al. (2001), Real-Time Analysis of G Protein-Coupled Receptor Reconstitution in a Solubilized System, J Biol Chem, 276, pp 22453–22460, the entire contents and disclosure of which is hereby incorporated by reference. These analyses did not allow us to identify the species responsible for LR-like behavior (i.e., LR, LRG-GTP, LRα-GTP, etc.). With the appropriate time resolution, the three different types of receptor assemblies should reveal the precise species present. A stopped-flow flow cytometer with resolution to about 40 msecs, see Graves et al. (2002), Nozzle Design Parameters and Their Effects on Rapid Sample Delivery in Flow Cytometry, Cytometry, 47, pp 127–137, the entire contents and disclosure of which is hereby incorporated by reference, and stopped-flow injection without sheath flow control, see Seamer et al. (1999), Sheath Fluid Control to Permit Stable Flow in Rapid Mix Flow Cytometry, Cytometry, 35, pp 75–79, the entire contents and disclosure of which is hereby incorporated by reference, provide the potential for 200 millisecond resolution (FIG. 2D). A triple fusion protein (R-α-GFP) should distinguish ligand disassembly from αβγ disassembly and activation, see Bevan et al. (1999), Functional Analysis of a Human A(1) Adenosine Receptor/Green Fluorescent Protein/G(I1)α Fusion Protein Following Stable Expression in CHO Cells, FEBS Lett, 462, pp 61–65, the entire contents and disclosure of which is hereby incorporated by reference.

Figure 4:
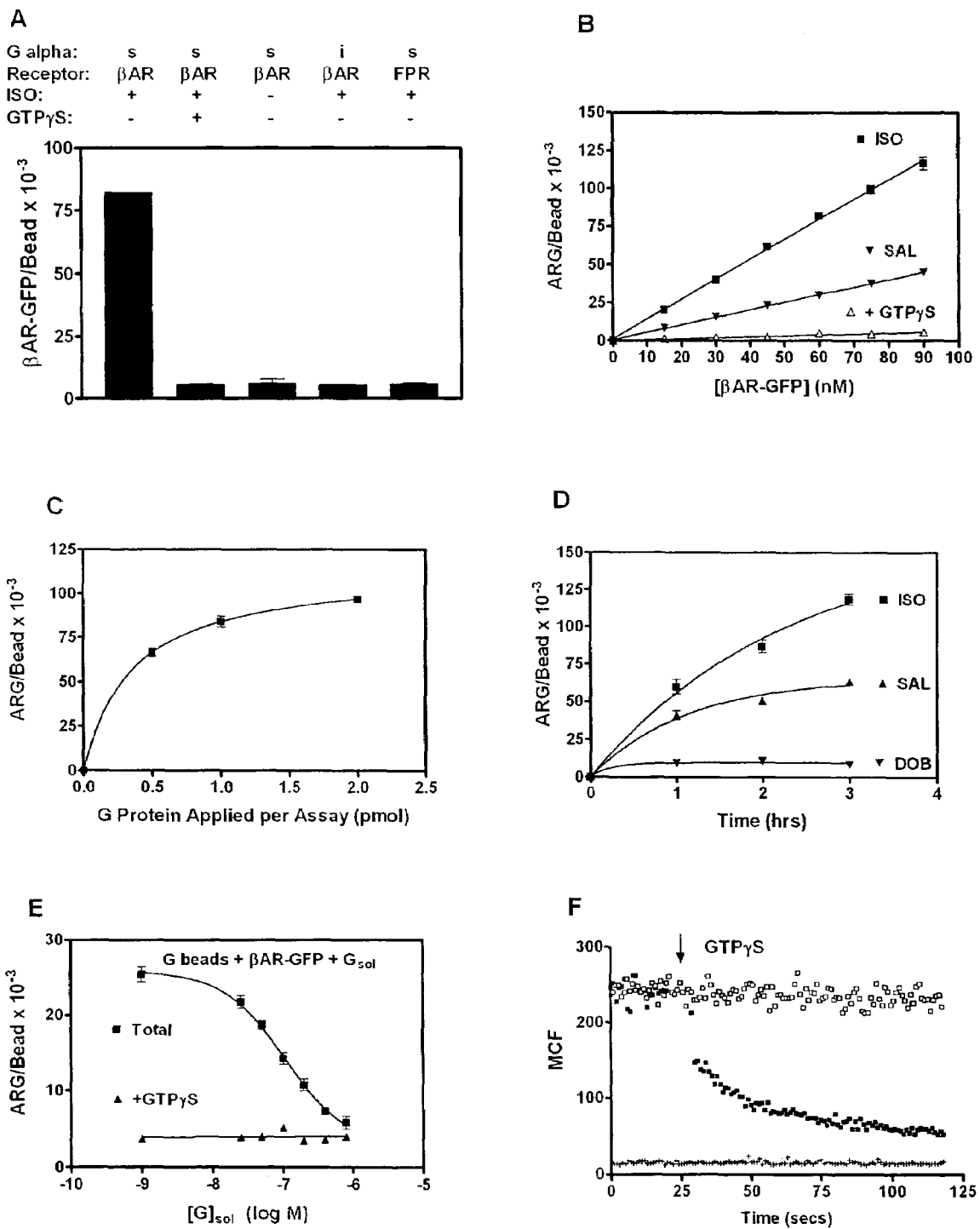
FIG. 4 illustrates the characterization of the ARG assembly on G beads.

Beads. The bead display of LRG complexes appears to be general. LRG formation occurs for three forms of FPR (wild type, receptor-Gα, and receptor-GFP), two epitope tags (hexahistidine and FLAG), two Gα subunits (αi2, (αi3) and two Gβ subunits (β1 and β4). Ternary complex formation has also been demonstrated with a β 2-adrenergic receptor-GFP fusion protein (see FIG. 4, and the following sections of this Patent Application). Other types of molecular assemblies are amenable to this technology.

Non-specific binding with nickel-chelate beads is a potential problem. For purified hexahistidine-tagged GFP, total binding was several million sites per bead. about 80% could be blocked by bovine serum albumin. about 400,000 epitope-tagged receptors from a crude mixture of solublilized proteins bound particle. For optimal ternary complex formation, about 100,000 G protein sites per particle were accessible. It may be that the purified H6-GFP binding (FIG. 9E) reflects all possible modes of binding (hexahistidine-tag dependent and independent), and is within an order of magnitude or less of covering the surface. On the other hand, specific binding of the non-his-tagged receptor plus ligand to G beads represent G proteins that are displayed in correct orientation on the surface, about 100,000. Most of the G protein, between the 100,000 displayed correctly and the total number of binding sites (>3 million), should be bound non-specifically and with improper orientation. The use of anti-FLAG beads avoids this problem, see Buranda et al. (2001), Detection of Epitope-Tagged Proteins in Flow Cytometry: Fluorescence Resonance Energy Transfer-Based Assays on Beads with Femtomole Resolution, Anal Biochem, 298, pp 151–162, the entire contents and disclosure of which is hereby incorporated by reference.

Screening and proteomics. The receptor-GFP fusion protein should adapt to high throughput screening, especially when coupled to HyperCyt™, which delivers beads to a flow cytometer from multiwell plates, see Kuckuck et al. (2001), High Throughput Flow Cytometry, Cytometry, 44, pp 83–90 and Jackson et al. (2002), Mixing Small Volumes for Continuous High-Throughput Flow Cytometry: Performance of a Mixing Y and Peristaltic Sample Delivery, Cytometry, 47, pp 183–191, the entire contents and disclosures of which are hereby incorporated by reference. Particle based screening is compatible with a search for ligands for both known and orphan receptors, see Stadel et al. (1997), Orphan G Protein-Coupled Receptors: a Neglected Opportunity for Pioneer Drug Discovery, Trends Pharmacol Sci, 18, pp 430–437, the entire contents and disclosure of which is hereby incorporated by reference, agonists promoting assembly on particles, and antagonists inhibiting them. Proteomics applications could be based on bead arrays, see Nolan J P and Sklar L A (1998), The Emergence of Flow Cytometry for Sensitive, Real-Time Measurements of Molecular Interactions, Nat Biotechnol, 16, pp 633–638, the entire contents and disclosure of which is hereby incorporated by reference, in this situation, color-coded particles would display individual $\alpha\beta\gamma$ combinations, one combination per color code. Specific subunit interactions could be assessed as a GFP-receptor binds to a subset of the combinations. Commercial hardware and software are already available for decoding the results of soluble, multiplex cytometric arrays, see Lund-Johansen et al. (2000), Flow Cytometric Analysis of Immunoprecipitates: High-Throughput Analysis of Protein Phosphorylation an Protein—Protein Interactions, Cytometry, 39, pp 250–259, the entire contents and disclosure of which is hereby incorporated by reference. Our standard coating of the nickel beads uses 0.7 pmol of G$\alpha\beta\gamma$ per assay to obtain a 3 to 1 ratio of total signal to nonspecific signal, while the anti-FLAG beads use 0.17 pmol of G$\alpha\beta\gamma$ per assay to obtain the same 3 to 1 ratio, using tens of thousands of beads. Smaller volumes and fewer beads would produce a more efficient screening process.

The present invention employs a flow cytometry device to perform measurements of the formation of complexes in a moving liquid stream. In the flow cytometry device a liquid stream forming a sheath fluid into which a sample is introduced is focused through an orifice. As the objects pass through the orifice, particular characteristics of the objects are determined based upon the analyzing or counting capabilities of the flow cytometry device. Typically, the flow cytometry device of the present invention is capable of sorting or counting at high speeds, collecting tens of thousands of objects.

Although many conventional flow cytometry devices may be used in the method of the present invention, one preferred commercially available flow cytometer is the FACScan™ instrument sold by Becton Dickinson Immunocytometry Systems, San Jose, Calif., which relies on a hydrodynamically focused fluid system. The FACScan™ instrument rapidly analyzes cells on the basis of fluorescence and light scatter properties. Analysis is accomplished by introducing cells in a suspension to the center of a focused liquid stream thus causing them to pass, one at a time, through a focused light from a high powered laser. Each cell is individually characterized by its light scatter signals and by the intensity and color of fluorescence emitted while it is illuminated. This system is described in U.S. Pat. No. 4,844,610 issued Jul. 4, 1989 to North, U.S. Pat. No. 5,030,022 issued Jul. 9, 1991 to North and U.S. Pat. No. 5,040,890 issued Aug. 20, 1991 to North, the entire contents and disclosures of which are hereby incorporated by reference.

The invention is described further in the following example, which is illustrative only and in no way limiting.

EXAMPLE 2

Experimental Procedures

Reagents and Cell Culture—All reagents were from Sigma and were of analytical quality unless otherwise noted; plasticware was from VWR. The $\beta$2-adrenergic receptor-GFP construct in pSFFV.Neo was obtained using the polymerase chain reaction, resulting in a fusion protein containing an extra AGANGAAA sequence between the final amino acid of the $\beta$-adrenergic receptor and the first amino acid of the GFP. The U937 cells were maintained, selected for high expression, expanded in spinner flasks, and frozen in aliquots as previously described (10).

Membrane Preparation and Solubilization—Preparation of crude, post-nuclear membrane aliquots, and solubilization of the membrane aliquots, have been described (10). A typical solublilized membrane aliquot contained the membrane proteins from $10^8$ cells, 100–200 nM $\beta$2AR-GFP, about 1 $\mu$M Gas and 5 mg/ml total protein, in 0.25 ml of 30 mM HEPES hemisodium salt, pH 7.5, 100 mM KCl, 20 mM NaCl, 1 mM $MgCl_2$ (HPSM) with 1% dodecyl maltoside. The quantification of $\beta$2AR-GFP by fluorescence is not absolute, for each harvest of cells may have a different percent of the protein enzymatically converted to the fully fluorescent form; a sample of hexahistidine-tagged GFP (kindly supplied by John Nolan, Los Alamos) gave a molar fluorescence (quantum yield) equal to 0.7 of the molar fluorescence of carboxyfluorescein in our fluorimeter (10). Two determinations of the active formyl peptide receptor in a preparation gave a value of 50% active receptor compared to the amount given by GFP fluorescence, and we have assumed 50% active PAR to GFP fluorescence in all calculations herein.

Synthesis of DHA Beads—We have previously described the synthesis of the Ni beads used herein (10). The synthesis of the DHA beads was based on the successful affinity chromatography material developed earlier (11). Both start with the epoxy-activation of Superdex Peptide beads, a crosslinked agarose/dextran matrix with an exclusion limit of 7,000 Daltons, which were extruded from a packed column purchased from Amersham Biosciences. One settled volume of the epoxy-activated beads was mixed with one volume of 0.2 M dithiothreitol in 0.2 M $NaHCO_3$ for 4 hrs at 37° C., then rinsed on a coarse sintered glass filter five times with water. One settled milliliter of these sulfhydryl-activated beads was stirred with 1 ml of water and 40 mg of (−)-alprenolol, and 10 $\mu$l of 10% ammonium persulfate was added every 10 minutes at 90° C. for 2 hrs (we note that this can be done at 25° C. (11), but we obtained lower substitution), with added water to keep the volume constant. The derivatized beads were washed twice with water, once with 50% ethanol, five times with ethanol, once with 50% ethanol, once with water, and twice with HPSM. The beads were stored as a 50% slurry in HPSM with 0.02% $NaN_3$ and 0.01% dodecyl maltoside at 4° C.

Binding Assay of $\beta$2AR-GFP to DHA Beads—Typically, 2 $\mu$l of the 50% suspension of DHA beads ($\sim 3.5 \times 10^5$ beads/$\mu$l) was treated with 200 $\mu$l of HPSM containing 0.1% dodecyl maltoside and 0.1% bovine serum albumin at 4° C. for 30–60 minutes to reduce nonspecific binding. The beads were centrifuged at 1,400×$g_{max}$ for 20 seconds, the buffer was removed, and the beads were resuspended in 50 µl of HPSM containing 0.1% dodecyl maltoside. This provided 25 aliquots of 24,000 beads, for 25 binding assays. A ten microliter binding assay generally consisted of two microliters of solublilized receptor preparation, two microliters of a ligand at some concentration, and four microliters of HPSM containing 0.1% dodecyl maltoside, which was mixed in a 96 well plate with a V bottom (Costar) by pipetting and allowed to equilibrate for 5 minutes. Then two microliters of the treated DHA bead suspension was added and mixed by pipetting, followed by orbital mixing for two hours at 4–7° C. Nonspecific binding was determined by the inclusion of 1 mM alprenolol. The wells were brought to 200 µl with HPSM containing 0.1% dodecyl maltoside, and their contents transferred to 12×75 mm tubes, immediately before flow cytometric analysis of the fluorescence on the beads. Conversion of the fluorescence measured to bound β2AR-GFP was made with calibration beads (Clontech).

Kinetic binding data of β2AR-GFP binding to DHA beads were analyzed via Scientist (MicroMath™, Salt Lake City, Utah). A single site binding model was utilized to fit the data and the forward binding rate constant, $k_f$, was evaluated with the reverse binding rate constant, $k_r$, constrained by the equilibrium dissociation constant, $K_d = k_r/k_f$ at 3.4 nM (from experimental data). The concentration of DHA was assumed to be 0.4 nM in each 10 µl binding assay based on 100,000 binding sites per bead and 24,000 beads per assay.

ARG Assembly Assay on G Protein Coated Beads—Coating of the Ni beads with heterotrimeric G proteins has been described before in detail (10). Briefly, 25 pmol of the desired α subunit and 25 pmol of hexahistidine-tagged β1γ2 were mixed with 2.5 µl of a 50% slurry of DCNi beads (2.5×10$^5$ beads/µl) and 190 µl of HPSM containing 0.1% dodecyl maltoside and 1 mM dithiothreitol, then kept in suspension by rocking at 4–7° C. for one hour. The beads were then centrifuged for 30 seconds at 1,500×$g_{max}$, the supernatant was removed, and the beads were resuspended in 50 µl of the buffer. This provided 25 aliquots of 24,000 G protein coated beads, for 25 ARG assembly assays (some beads were lost to surfaces). A ten microliter ARG assembly assay generally consisted of two microliters of solubilized receptor preparation, two microliters of desired ligand, four microliters of HPSM containing 0.1% dodecyl maltoside, and two microliters of G protein coated beads. Nonspecific fluorescence was defined in the presence of 0.1 mM GTPγS. These suspensions were mixed on an orbital mixer for 2 hours, brought to 200 µl with HPSM containing 0.1% dodecyl maltoside, transferred to a 12×75 mm tube, and immediately analyzed by flow cytometry for bead fluorescence. For kinetic data, tubes were removed from the cytometer after twenty seconds, 2 µl of 10$^{-2}$ M GTPγS was added and mixed, and the tubes were returned to the cytometer for measurement of the bead fluorescence. The cytometer data were converted to alphanumeric form and binned into one second intervals using the FACSQuery program (available free from Bruce Edwards), which provides a series of mean channel fluorescence (MCF) values in an Excel file. These data were then analyzed using Prism (Graphpad Software).

For multiplex analysis, the Ni beads were given a red 'address label' for dual bead experiments (Ni and DHA bead in one well) by reacting 10 µl of a 50% slurry of DCNi beads with 10 µl of 10$^{-4}$ M NHS-Texas Red™ in DMSO (Molecular Probes) in 80 µl of phosphate buffered saline for 10 minutes at 22° C., then washing with 900 µl of 50% ethanol, twice with 100% ethanol, once with 50% ethanol, and three times with HPSM. Both types of beads were stored at 4° C. in HPSM with 0.01% dodecyl maltoside and 0.02% sodium azide for at least six months, and were stable to at least one snap-freeze at −80° C. One settled milliliter of beads (~5× 10$^8$ beads) could be used for ~20,000 assays of 24,000 beads each.

Results

Binding of β2AR-GFP to DHA Beads—Based upon earlier work demonstrating affinity chromatography of β2AR (11), we derivatized Superdex Peptide beads to display dihydroalprenolol on the end of an 18 atom linker (FIG. 1). These DHA beads are built on a matrix of crosslinked agarose/dextran 13 µm in diameter with a 7,000 Dalton exclusion pore size, which restricts proteins to the surface. We also produced a β2AR-GFP fusion protein, and expected that after solubilization it would bind to the DHA on the surface of the beads as shown schematically in FIG. 2A, making the beads fluorescent.

Figure 2:
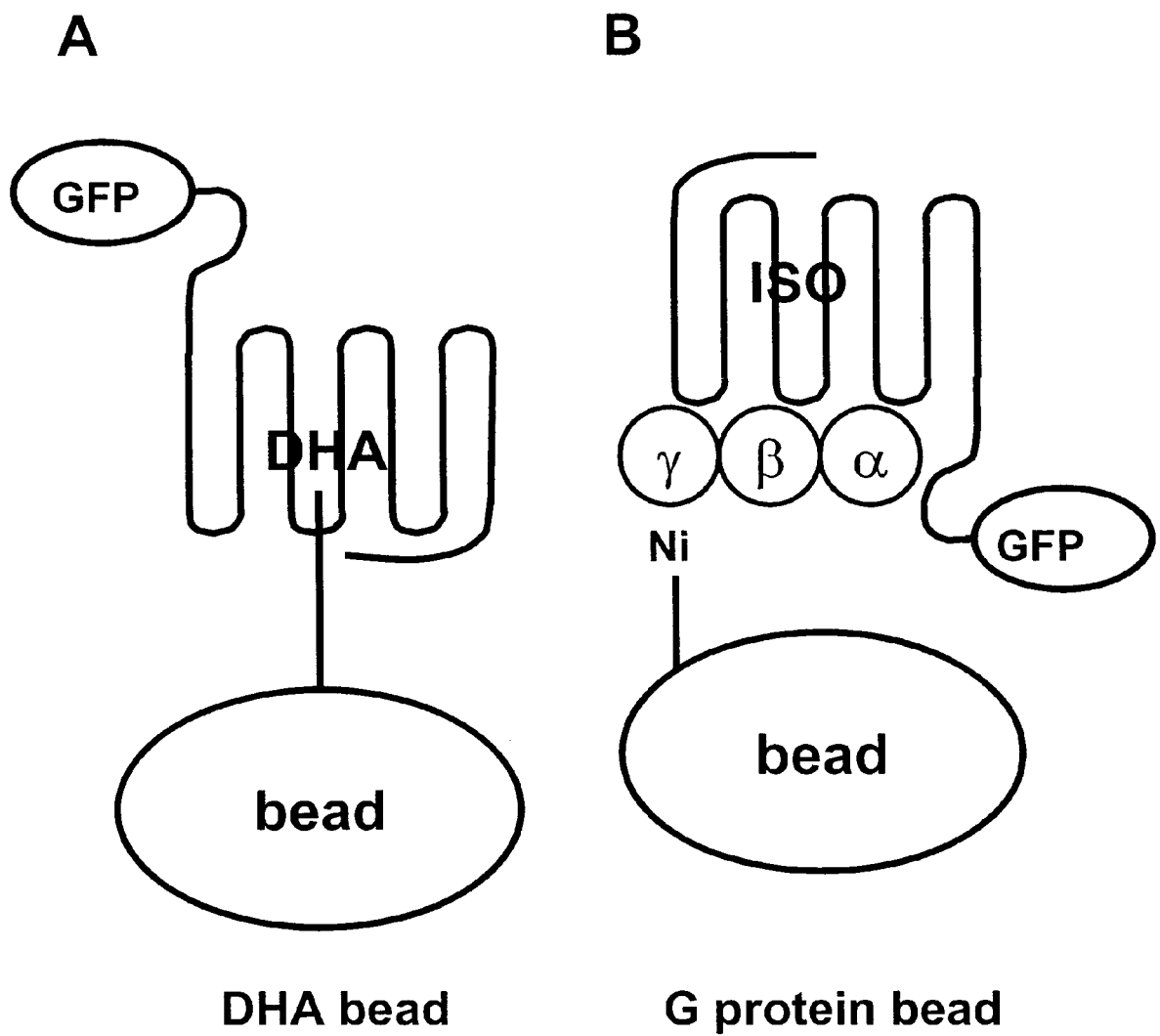
FIG. 2 illustrates schematic diagrams of the two positive receptor-bead interactions used in this invention.

The receptor-GFP fusion protein is depicted in FIG. 2 as a snakeview receptor with an oval GFP on its C-terminus. The DHA beads will bind to the β2AR-GFP unless a ligand has occupied the binding site previously. In FIG. 2B, Ni beads were first converted to G protein beads by incubation with hexahistidine-tagged G protein heterotrimers, as described in "Experimental Procedures". The β2AR-GFP will bind these G protein beads only when occupied by an agonist, here shown as isoproterenol, ISO.

Figure 3:
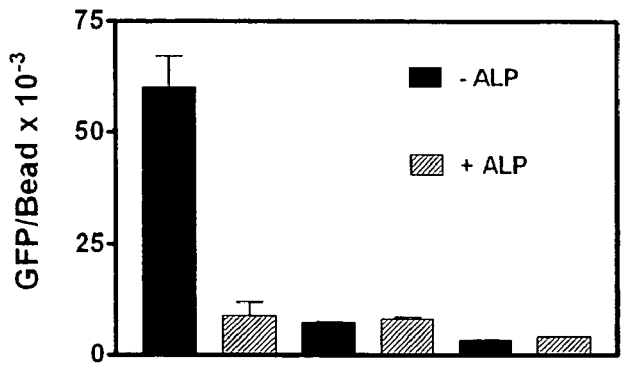
FIG. 3 illustrates the characterization of the DHA bead binding assay. Binding assays were conducted as described in "Experimental Procedures".
Figure 3:
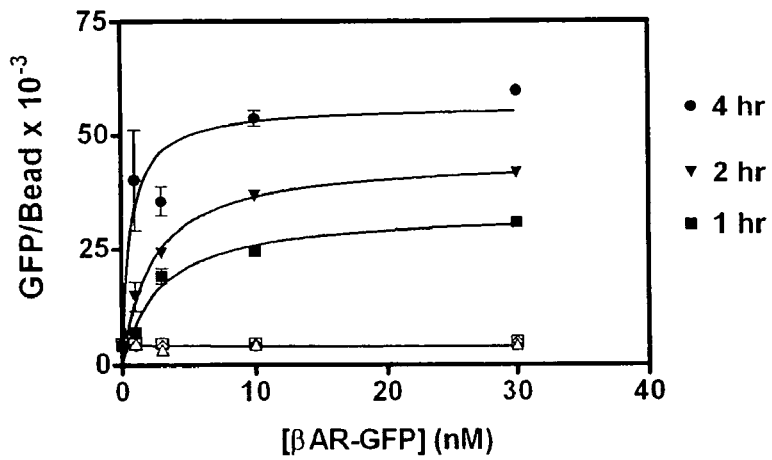
Figure 3:
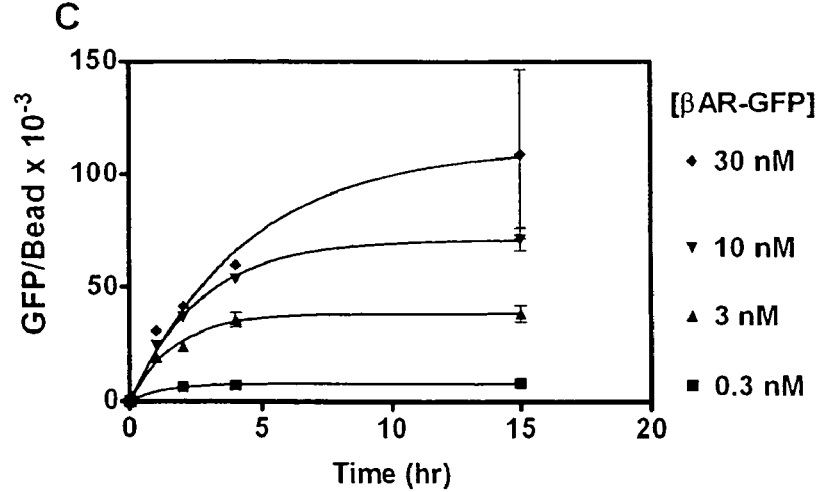

Membranes from U937 cells that were expressing β2AR-GFP were isolated and frozen, then aliquots of the membranes were thawed and solublilized (see "Experimental Procedures") to produce soluble β2AR-GFP in a background of other membrane proteins. Binding assays were conducted (see "Experimental Procedures") to test the specificity of the proposed interaction (FIG. 3A). In the presence of 50 nM β2AR-GFP, ~60,000 GFP molecules were bound per bead, while when the receptor was blocked with 1 mM alprenolol, only 10,000 GFP molecules were bound per bead. Specific binding is the difference between these two bars, or 50,000 β2AR-GFP/bead. When a fusion protein consisting of the formyl peptide receptor and GFP (FPR-GFP) was used instead of β2AR-GFP, the binding was low in both the absence and presence of alprenolol, as expected. Underivatized beads, less hydrophobic, bound even less 'background' fluorescence than the derivatized beads, as expected.

We then tested this interaction as a function of time of incubation of β2AR-GFP with the DHA beads, using 0.3–30 nM β2AR-GFP (FIG. 3B). One, two, and four hours of binding resulted in binding curves that gave a $K_d$=3.4+/−0.4 nM, which agrees with values obtained from membrane preparations (12) and dodecyl maltoside-solubilized preparations (13). As the reaction was time-dependent, we chose 2 hours as a standard time. With 100,000 β2AR-GFP molecules on the surface of 24,000 beads in 10 µl, only 0.4 nM β2AR-GFP is on the beads, compared to the tens of nanomolar β2AR-GFP in solution. Analysis of the kinetic data of β2AR-GFP binding to DHA beads (FIG. 3C) resulted in values for the forward binding rate constant, $k_f$=2.9±1×10$^3$ M$^{-1}$ sec$^{-1}$, and for the dissociation rate constant, k'=8.6±4× 10$^{-6}$ sec$^{-1}$. We note that $k_f$ is ~two orders of magnitude lower than reported for the binding of similar size antibody Fab fragments to epitopes on cells at 4° C. (14). The active (−) stereoisomer of alprenolol was used in constructing the present DHA beads, in contrast to the racemic mixture used in the original affinity medium (11). The elution of 40–60% of the receptors from the original affinity medium may have resulted from receptors that were bound to the more weakly binding (+) stereoisomer.

ARG Ternary Complex Assembly on G Protein Beads—The agonist-receptor-G protein assembly (ARG assembly, FIG. 2B) assay was based on earlier work (10). Here, assemblies were formed in 10 µl volumes to maximize concentrations of A, R, and G protein coated beads, then diluted for immediate flow cytometric determination of the bead fluorescence. In FIG. 4A, we demonstrate that this ARG assembly requires a cognate set of agonist, receptor, and G protein coated beads. The binding of 40 nM β2AR-GFP to G protein beads in the presence of saturating isoproterenol (1 mM) gave a total fluorescence of 80,000 β2AR-GFP/bead. When 0.1 mM GTPγS, a non-hyrolyzable GTP analog, was added in this assembly, the fluorescence was reduced to a background of about 10,000 β2AR-GFP/bead, which demonstrates that a G protein alpha subunit is necessary for specific fluorescence. Specific binding was defined as the difference between these two values, and is referred to as ARG/bead. In the absence of the agonist isoproterenol, only background binding was observed, demonstrating the necessity for a correct ligand for the assembly. When GFP was fused to the formyl peptide receptor, background fluorescence was again obtained, demonstrating the necessity of the correct receptor for specific fluorescence. Finally, G protein beads were assembled with αi3 subunits instead of the cognate αs subunits, and these beads also gave background fluorescence. (The control assembly with cognate FPR-GFP showed specific binding, indicating active G protein beads, data not shown). Thus, the cognate agonist, receptor, and G protein were all necessary to obtain the specific fluorescence, or ARG assembly.

We then varied the concentration of β2AR-GFP in the presence of two selected agonists, at saturating concentration, in the standard ARG assembly assay, as shown in FIG. 4B. It can be seen that the GFP/bead increases linearly with the concentration of β2AR-GFP for both agonists, with the full agonist, isoproterenol, showing the greatest slope. These data are consistent with a low affinity between agonist-bound β2AR-GFP and the G beads: a $K_d$ of 0.2–0.4 µM has been found for the interaction of agonist-bound formyl peptide receptor and Gαi3, for example (10) and would be consistent with the present data (see also FIG. 4E). The full agonists epinephrine and norepinephrine were indistinguishable from isoproterenol, and the partial agonist dobutamine gave a line with ⅔ the slope of salbutamol (data not shown). These data suggested the presence of ligand specific conformations of binary AR complexes, with full agonists giving a maximal slope, and partial agonists giving a lower slope.

The amount of G protein applied to the beads, before washing and introduction to the ARG assembly assay, was varied next. Polyacrylamide gel electrophoresis showed that for the standard application, 1 pmol G protein/24,000 beads, over 80% of the applied protein bound to the beads and stayed on when the beads were resuspended (data not shown). In FIG. 4C it is shown that the amount of ARG assembly on the beads was a saturable function of the G protein applied to the beads. We believe that this represents saturation of the surface of the beads with G protein that is in the correct orientation to allow binding of the subsequently added partners, not an $EC_{50}$ for ARG formation, which will be discussed later. Our standard assembly assay protocol thus results in 75% saturation of the surface of the G beads, using 1 pmol of G protein heterotrimers per assay.

The time of assembly was varied with saturating amounts of agonists in FIG. 4D, and as with the DHA bead binding, ARG assembly continued increasing past three hours for isoproterenol and salbutamol, while for the weak partial agonist dobutamine, ARG assembly was maximal by 1 hour. The amount of ARG formed with isoproterenol was always greater than that formed with salbutamol, which was always greater than that formed with dobutamine. To compare results between experiments, the time of assembly was standardized to two hours. Thus, our standard assembly assay was 75% saturated with respect to G protein coverage on the bead, was linear with respect to β2AR-GFP past 60 nM β2AR-GFP, depended on the specific agonist used for assembly, and would increase with time past the standard two hours if allowed to do so for isoproterenol and salbutamol.

Competition between G protein on the G beads and soluble G protein was used to estimate the affinity of agonist-bound β2AR-GFP for G protein in FIG. 4E. The large amount of soluble G protein used in this experiment precluded multiple determinations, but the data are consistent with $K_d$=0.09–0.11 µM, similar to the 0.3–1 µM $K_d$ of the agonist-bound formyl peptide receptor and Gαi3β1γ2 (10).

Standard ARG assemblies were made, then diluted for kinetic determination of bead fluorescence by flow cytometry, as shown in FIG. 4F. The open squares represent a sample in which the bead fluorescence was followed uninterrupted for two minutes, to determine the dissociation due to dilution alone, and it is clear that there was only minimal loss of ARG over this time frame. The closed squares show the bead fluorescence when 0.1 mM GTPγS was added manually to a parallel assembly at about 25 seconds, and data collection was resumed at about 30 seconds to follow the disassembly of the ARG. A substantial loss of fluorescence occurred in the first five seconds after GTPγS addition, followed by a gradual loss for the rest of the data collection. The plus symbols represent the fluorescence of an assembly that had been conducted in the presence of GTPγS, and constitute background fluorescence for the experiment.

Determinations of $K_d$ for LR Dissociation and $EC_{50}$ for ARG Formation—LR formation on DHA beads was competed by the addition of selected ligands, which allowed us to measure the $K_d$ values as detailed in "Experimental Procedures". (Since the beads act as a sensor, with [bound receptor]<<[free receptor]<[L], the $IC_{50}$ values equal $K_d$ values to within experimental error for all the agonists.) FIG. 5A shows the competition curves for these determinations, which are consistent with a single population of noninteracting binding sites, as expected. The $K_d$ values are compared to previously reported $K_d$ values obtained with membrane preparations (Reference 15) in Table 1 (FIG. 16). The $K_d$ for alprenolol in dodecylmaltoside solution has been reported to be 2.9 nM (13); in a separate experiment in which the concentration of receptor was reduced to 3 nM, we obtained a $K_d$ of 1.8 nM. The $K_d$ values for the rest of the ligands agreed with the previously reported $K_d$ values obtained with membrane preparations to within a factor of three.

ARG assembly on G beads was measured as a function of the concentration of selected agonists, and FIG. 5B displays these results. The curves were consistent with the assembly acting as a simple dose-response with respect to the concentration of each ligand. $EC_{50}$ values obtained from these data, or potencies of the agonists, are reported in Table 1. While precise potencies depend on the specific G protein heterotrimers in a given preparation, the rank order of potency for these ligands agrees with membrane data (12). We noticed also the appearance of partial agonism, in which the curves for salbutamol and dobutamine each climbed to ARG/bead levels that were thirty percent and ten percent, respectively, of the level reached by the full agonist isoproterenol. While precise efficacies depend on the specific G protein heterotrimers in a preparation, the rank order of efficacy of these ligands agrees with membrane data (12).

Kinetics of ARG Activation by GTPγS—Ternary complexes were assembled as above, using the full agonist isoproterenol and the partial agonists salbutamol and dobutamine. These were analyzed by flow cytometry as described in the legend to FIG. 6. The rate of disassembly of each ternary complex was followed after addition of GTPγS. All three ligands gave the same kinetic rate for this process, 0.09 sec$^{-1}$, within experimental error. Mechanisically, this rate-determining step of ARG disassembly is therefore independent of the affinity of the ligand. Based on previous results with the formyl peptide receptor (10), it most likely arises from the dissociation of AR from Gα:GTPγS rather than dissociation of Gα from Gβγ.

Figure 7:
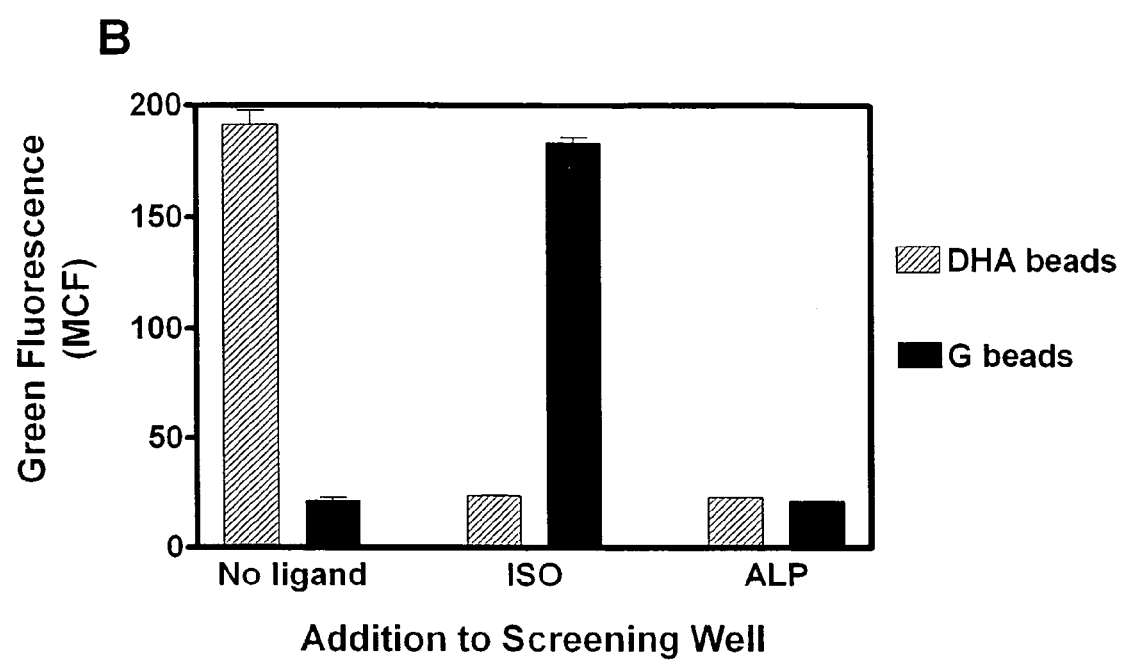
FIG. 7 illustrates simultaneous determination of agonist, antagonist, and inactive compounds using duplex flow cytometry. G protein beads colored with Texas Red™ (G-TR) and DHA beads (DHA) were mixed with 20 nM β2AR-GFP in the absence of ligand, the presence of 1 mM ISO, or the presence of 1 mM ALP. The cytometer determined the green fluorescence of the uncolored beads separately from the green fluorescence of the red-colored beads for each well. Data from the uncolored DHA beads are represented as striped bars; data from the colored G protein beads in the same wells are represented as filled bars.

Simultaneous Determination of Agonist and Antagonist—Results with the DHA beads and the G protein beads suggested that one could obtain data from a single 10 μl mixture of both beads in one well, sharing the same receptor and ligand, which would determine whether the ligand was an agonist, an antagonist, or inactive. To this end, a sample of Ni beads was reacted with activated Texas Red™ (see "Experimental Procedures"), then coated with G proteins using the standard protocol. We verified that labeling the beads did not affect their behavior (data not shown). These labeled beads allowed us to observe molecular assemblies in duplex form, with DHA beads incubated in the same well as the Texas Red™ colored G protein beads. In this case, the flow cytometer separated the green fluorescence of the red beads from the green fluorescence of the colorless beads. The results for DHA beads in duplex form were similar to the results in standard form (data not shown), and the results for the Texas Red™ colored G protein beads in duplex form were the same as G protein beads incubated in separate wells. This duplex data is shown in the form in which the data would be obtained in a screen for active ligands (FIG. 7). The inactive compound allows β2AR-GFP binding to DHA beads, but not ARG formation; the agonist prevents β2AR-GFP binding to DHA beads and allows ARG formation; and an antagonist blocks β2AR-GFP binding to DHA beads and does not promote ARG formation.

DISCUSSION

Solubilization of GPCRs and Cytometric Display—Both the FPR-GFP and β2AR-GFP have now been successfully displayed in soublized form on particles for flow cytometric analysis. While three different constructs of the FPR have been detected (both by GFP and fluorescent ligands), the most general approach to GPCR display is likely to be based on GFP fusion proteins. While solubilization has proven to be a key element in characterizing GPCR assemblies (7–9), the retention of GPCR binding activity has proven elusive and largely a matter of trial and error. Particle display, an analog of the methods used in routine protein purification, leads to the possibility of a general solubilization approach, in which different detergents are screened to solubilize receptor-GFP fusion proteins, and the retention of activity is assessed using the criterion of specific assembly on the particles by flow cytometry.

Ligand Beads—To display the β2AR ligand, DHA, we used an affinity chromatography support (11). The β2-adrenergic receptor-GFP construct bound saturably to DHA beads with $K_d$=3.4 nM, which agrees with data from membrane preparations (12) and solubilized preparations (13). The binding of β2AR-GFP to the DHA beads was specific for the cognate receptor, was blocked with cognate ligand, and was insensitive to GTPγS. β2AR-GFP binding to DHA beads was slower than the binding of antibody Fab fragments of comparable size to a cell epitope. This may have been because a Fab fragment binds its epitope in a lock-and-key manner, while a receptor binds its ligand with induced conformational changes. The rank order of potency of selected β2-adrenergic agonists was the same as reported previously (15). The derived $K_d$ values were within a factor of three of those shown earlier, showing that the receptor preserves its natural ligand interaction. The $K_d$ value for alprenolol in competition was 1.8 nM, similar to the $K_d$ for DHA on the bead of 3.5 nM.

G Protein Beads—To display G proteins, we used beads bearing chelated nickel (10) which bound purified hexahistidine-tagged G protein heterotrimers (Gαsβ1γ2) and recognized β2AR. The assembly specificity appears to have been governed by the α subunit, while the β1γ2 may not have been the optimal choice (16). The $K_d$ for ARG assembly was determined to be about 0.1 μM G protein by competition with free G heterotrimer in the presence of saturating isoproterenol. The time of assembly, far longer than assembly in a cell, was not unexpected based on receptors and G protein diluted many times compared to their state in membranes. It is noteworthy that, taken together, ligand beads and G protein beads with GPCR-GFPs provide essentially the same level of detail normally available through GPCR radioligand binding analysis.

Partial Agonists and Their Assays—The physiological response to an adrenergic ligand depends on the types and levels of expression of receptor, G protein subunits, adenylate cyclase isozymes, and cyclic nucleotide-dependent enzymes in various tissues, plus the adrenergic tone of the organism. Our results are analogous to classical studies of radioligand binding to β2AR in membranes (3), which showed two distinct binding states for agonists, one of low affinity (AR) and one of high affinity (ARG). The efficacy of an agonist was defined by its closest measureable output, adenylyl cyclase activity, compared to that of the full agonist isoproterenol: a partial agonist meant an agonist with less than 100% efficacy. In membrane binding assays, isoproterenol induced a high amount of ARG (80% ARG form) and adenylyl cyclase activity (defined as 100% efficacy). The percent ARG form was found to correlate with efficacy: partial agonists ranged from a low of 58% ARG form with 8% efficacy (soterenol), to 93% ARG form with 110% efficacy (hydroxybenzylisoproterenol) (3). Our present approach with solubilized components provides a more direct measurement of ARG assembly, and can be compared to the efficacy obtained earlier (3). Using 20 nM β2AR-GFP, maximal concentrations of the partial agonist salbutamol produced 30% as much ARG assembly as did the full agonist ISO in our assay, which is in good agreement with the previously determined 20% efficacy. Dobutamine was not used in the earlier work. Our results with the chosen ligands mirror membrane data in three ways: binding affinities correlate well; EC$_{50}$ values for ARG formation, which contain different G proteins in different studies, show the same rank order of potency; and partial agonists, which could be masked by different levels of R to G protein, display the same rank order of efficacy.

Mechanism of Partial Agonism. Under conditions of agonist saturation, receptors exist either as AR or ARG complexes, and the ternary complex steps are represented simplistically as equation 1. Efficacy is then the overall rate of activation of G protein, and depends upon both the rate of assembly of ARG and the rate of activation with saturating GTP. In our hands, the kinetics of ARG assembly depend on the nature of the agonist used, while the kinetics of GTPγS-induced disassembly of AR from ARG do not. Our data do not directly address the rate of G protein activation to the adenylyl cyclase stimulatory conformation. The assembly data suggest that AR complexes formed by partial agonists have a lower affinity for G than AR complexes formed by full agonists: the approach to ternary complex equilibrium is faster for the partial agonist dobutamine than for isoproterenol, and there is a lower amount of ternary complex formed. Our data is consistent with evidence for agonist-induced conformational states in the β2AR (13; 17). Our results may be comparable to membrane systems, as it is difficult to imagine that the underlying rate constants would change between membrane and soluble systems while conserving affinity, potency, and efficacy.

Our results agree with a previous study of the muscarinic acetylcholine receptor, which showed indirectly that the reduced efficacy of a partial agonist was the result of a decrease in affinity of the agonist-receptor complex for G protein (18). Our results do not directly address another previous study of the β2AR, which showed indirectly that there were different rates of heterotrimer activation for partial agonists compared to full agonists That study used the long splice variant of αs, compared to the short splice variant used here (19).

While likely to reflect insufficient G protein activation, partial agonism in cells could be masked by spare receptors (20) that allow saturation of G protein activation without full receptor occupancy. Thus, molecular tests for partial agonists are physiologically significant. Partial β2-adrenoreceptor agonists have been useful in the treatment of asthma, where there is substantial evidence that use of high-dose formulations of full agonists, taken with inhalers to relax airway smooth muscle, resulted in epidemics of mortality (21). Intrinsic efficacies of agonists have been difficult to measure because both the concentration dependency and the maximal effect of an agonist depends on the density of receptors in tissues (20). The high density of adrenoreceptors in airway smooth muscle results in maximal relaxation despite salbutamol's partial agonism, while the lower receptor density in nontarget tissues limits cardiac and metabolic side effects (22). A second possible benefit of partial agonists is that they induce less desensitization than full agonists, thus allowing a patient to use the inhaler many times without diminished effect (23; 24).

The ARG assembly assay, at high doses of ligands, is able to predict partial as well as full agonists, since it is performed under conditions of receptor excess in which the G protein beads serve essentially as sensors. The components of the assay cost less than two cents except for the β2AR-GFP, for which the fetal calf serum costs about five cents per assay, and purified G proteins. The receptor-GFP construct retains all physiological binding properties that we have measured.

Discrimination of Agonists and Antagonists—Multiplexing of flow cytometric data gives multiple determinations from one sample well, thus having each constituent determination performed under identical conditions. We used both types of beads described herein together in a duplex (the simplest form of multiplex) assay to simultaneously determine whether a test compound was an agonist, antagonist, or neither. It is noteworthy that a partial agonist could also be determined, if a full agonist response were already in the data set, or by a dose-response analysis of ARG assembly in a secondary screen. Our data only use a single G protein heterotrimer, but different heterotrimers could be put onto beads with different addresses, as a suspension array (25), enabling one to scan various classes of G proteins simultaneously for interaction. This has been done recently for the 5-hydroxytryptamine receptor, using a more complex antibody capture procedure (26). Multiplexed analysis using HyperCyt™, an automated system capable of sampling up to 100 samples of about one microliter from multiwell plates per minute (27), provides the potential for simultaneously discriminating agonists and antagonists for high throughput flow cytometric drug discovery. HyperCyt™ could also make possible high throughput screening of detergents giving solubilization of active GPCR-GFPs, and could be applied to numerous other GPCR or other molecular assemblies.

REFERENCES

1. Bockaert, J. and Pin, J. P. (1999) *EMBO J.* 18, 1723–1729
2. Wise, A., Gearing, K., and Rees, S. (2002) *Drug Discov. Today* 7, 235–246
3. Kent, R. S., De Lean, A., and Lefkowitz, R. J. (1980) *Mol. Pharmacol.* 17, 14–23
4. DeLean, A., Stadel, J. M., and Lefkowitz, R. J. (1980) *Journal of Biological Chemistry* 255, 7108–7117
5. Neer, E. J. (1995) *Cell* 80, 249–257
6. Christopoulos, A. and Kenakin, T. (2002) *Pharmacol. Rev.* 54, 323–374
7. Bennett, T. A., Key, T. A., Gurevich, V. V., Neubig, R., Prossnitz, E. R., and Sklar, L. A. (2001) *J. Biol. Chem.* 276, 22453–22460
8. Bennett, T. A., Foutz, T. D., Gurevich, V. V., Sklar, L. A., and Prossnitz, E. R. (2001) *J. Biol. Chem.* 276, 49195–49203
9. Key, T. A., Bennett, T. A., Foutz, T. D., Gurevich, V. V., Sklar, L. A., and Prossnitz, E. R. (2001) *J. Biol. Chem.* 276, 49204–49212
10. Simons, P. C., Shi, M., Foutz, T., Cimino, D. F., Lewis, J., Buranda, T., Lim, W. K., Neubig, R. R., McIntire, W. E., Garrison, J., Prossnitz, E., and Sklar, L. A. (2003) *Mol. Pharmacol.* 64, 1227–1238
11. Caron, M. G., Srinivasan, Y., Pitha, J., Kociolek, K., and Lefkowitz, R. J. (1979) *J. Biol. Chem.* 254, 2923–2927
12. Mukherjee, C., Caron, M. G., Mullikin, D., and Lefkowitz, R. J. (1976) *Mol. Pharmacol.* 12, 16–31
13. Gether, U., Lin, S., and Kobilka, B. K. (1995) *J. Biol. Chem.* 270, 28268–28275
14. Nolan, J. P., Chambers, J. D., and Sklar, L. A. (1998) Cytometric Approaches to the Study of Receptors. In Robinson, J. P. and Babcock, G. F., editors. *Phagocyte Function: A Guide for Research and Clinical Evaluation*, Wiley-Liss, Inc., 15. Green, S. A., Cole, G., Jacinto, M., Innis, M., and Liggett, S. B. (1993) *J. Biol. Chem.* 268, 23116–23121
16. Robillard, L., Ethier, N., Lachance, M., and Hebert, T. E. (2000) *Cell Signal.* 12, 673–682
17. Ghanouni, P., Gryczynski, Z., Steenhuis, J. J., Lee, T. W., Farrens, D. L., Lakowicz, J. R., and Kobilka, B. K. (2001) *J. Biol. Chem.* 276, 24433–24436
18. Tota, M. R. and Schimerlik, M. I. (1990) *Mol. Pharmacol.* 37, 996–1004
19. Krumins, A. M. and Barber, R. (1997) *Mol. Pharmacol.* 52, 144–154
20. Kenakin, T. (2002) *Nat. Rev. Drug Discov.* 1, 103–110
21. Barrett, T. E. and Strom, B. L. (1995) *Am. J. Respir. Crit Care Med.* 151, 574–577
22. Bremner, P., Siebers, R., Crane, J., Beasley, R., and Burgess, C. (1996) *Chest* 109, 957–962
23. Clark, R. B., Knoll, B. J., and Barber, R. (1999) *Trends Pharmacol. Sci.* 20, 279–286
24. January, B., Seibold, A., Whaley, B., Hipkin, R. W., Lin, D., Schonbrunn, A., Barber, R., and Clark, R. B. (1997) *J. Biol. Chem.* 272, 23871–23879
25. Nolan, J. P. and Sklar, L. A. (1998) *Nat. Biotechnol.* 16, 633–638
26. Cussac, D., Newman-Tancredi, A., Duqueyroix, D., Pasteau, V., and Millan, M. J. (2002) *Mol. Pharmacol.* 62, 578–589
27. Waller, A., Simons, P., Prossnitz, E. R., Edwards, B. S., and Sklar, L. A. (2003) *Comb. Chem. High Throughput. Screen.* 6, 389–397
28. U'Prichard, D.C., Bylund, D. B., and Snyder, S. H. (1978) *J. Biol. Chem.* 253, 5090–5102
29. Bylund, D. B. (1978) *Brain Res.* 152, 391–395
30. Staehelin, M., Simons, P., Jaeggi, K., and Wigger, N. (1983) *J. Biol. Chem.* 258, 3496–3502
31. Leysen, J. E., Gommeren, W., Eens, A., de Chaffoy, d. C., Stoof, J. C., and Janssen, P. A. (1988) *J. Pharmacol. Exp. Ther.* 247, 661–670

FOOTNOTE

[1]The abbreviations used are: GPCR, G protein-coupled receptor; β2AR, β2-adrenergic receptor; β2AR-GFP, β2-adrenergic receptor-green fluorescent protein fusion protein; FPR-GFP, formyl peptide receptor-green fluorescent protein fusion protein; GTPγS, guanosine 5'-3-O-(thio)triphosphate; ARG, agonist-receptor-G-protein ternary complex; ALP, alprenolol; DHA, dihydroalprenolol; ISO, isoproterenol; Epi, epinephrine; NE, norepinephrine; SAL, salbutamol; DOB, dobutamine.

What is claimed is:

1. A method comprising evaluating the relative G protein receptor agonism, antagonism or inactivity of a compound for a G protein coupled receptor (GPCR) in a single sample by a flow cytometric process comprising the steps of (a) providing a sample suspension containing a detectable GPCR, a set of G protein beads which will form a ternary complex with said detectable GPCR in the presence of an agonist or partial agonist, and a set of ligand beads which will bind to said detectable GPCR, said set of G-protein beads comprising epitope-recognizing beads having an epitope bearing heterotrimeric G protein bound thereto and wherein at least one of said set of G protein beads and said set of ligand beads are detectable colored beads; (b) mixing said sample suspension with said compound; and (c) detecting the formation or absence of formation of a complex between said compound and said detectable GPCR, wherein a GPCR antagonist prevents binding of said detectable GPCR to said G protein beads by preventing ternary complex formation and prevents binding of said detectable GPCR to said ligand bead; a GPCR agonist allows binding of said detectable GPCR to said G protein beads by forming a ternary complex but prevents binding of said detectable GPCR to said ligand bead; and an inactive compound prevents binding of said detectable GPCR to said G protein beads by not promoting ternary complex formation but allows binding of said detectable GPCR to said ligand bead.

2. A method of claim 1, wherein the G protein coupled receptor is a β2-adrenergic receptor containing a fluorescent moiety.

3. A method of claim 2, wherein the fluorescent moiety is a fluorescent protein fused to said G protein coupled receptor.

4. A method of claim 2, wherein the detectable β2-adrenergic receptor containing a fluorescent moiety is a β2AR-Green Fluorescent Protein (GFP) fusion protein.

5. The method of claim 1 wherein said G protein beads are modified with a fluorescent moiety.

6. The method of claim 5 wherein said fluorescent moiety is a sulforhodamine 101 fluorescent moiety.

7. The method according to claim 1 wherein said ligand beads are modified with a fluorescent moiety.

8. The method according to claim 1 wherein said G protein beads and said ligand beads are modified with a fluorescent moiety.

* * * * *